US009994823B2

(12) United States Patent
Yoon et al.

(10) Patent No.: US 9,994,823 B2
(45) Date of Patent: Jun. 12, 2018

(54) PURIFICATION OF CELL MIXTURES USING MOLECULAR BEACONS TARGETING CELL SPECIFIC RNA

(71) Applicants: Emory University, Atlanta, GA (US); Georgia Tech Research Corporation, Atlanta, GA (US)

(72) Inventors: Young Sup Yoon, Atlanta, GA (US); Gang Bao, Mableton, GA (US); Kiwon Ban, Dectaur, GA (US); Brian Wile, Grayson, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 0 days. days.

(21) Appl. No.: 15/273,164

(22) Filed: Sep. 22, 2016

(65) Prior Publication Data
US 2017/0002326 A1    Jan. 5, 2017

Related U.S. Application Data

(62) Division of application No. 14/211,430, filed on Mar. 14, 2014, now Pat. No. 9,493,742.

(60) Provisional application No. 61/787,364, filed on Mar. 15, 2013.

(51) Int. Cl.
*C12N 5/077* (2010.01)
*C12Q 1/68* (2018.01)
(52) U.S. Cl.
CPC ......... *C12N 5/0657* (2013.01); *C12Q 1/6881* (2013.01); *C12Q 1/6888* (2013.01); *C12N 2501/115* (2013.01); *C12N 2501/155* (2013.01); *C12N 2501/16* (2013.01); *C12N 2501/999* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 6,692,965 | B1 | 2/2004 | Shekdar |
| 7,220,582 | B2 | 5/2007 | Epstein |
| 7,727,762 | B2 | 6/2010 | Fukuda |
| 8,039,259 | B2 | 10/2011 | Riemen |
| 8,153,427 | B2 | 4/2012 | Nistor |
| 8,158,421 | B2 | 4/2012 | Passier |
| 8,252,583 | B2 | 8/2012 | Fukuda |
| 8,293,529 | B2 | 10/2012 | Koshimizu |
| 9,493,742 | B2 | 11/2016 | Yoon |
| 2010/0212040 | A1 | 8/2010 | Shekdar |

FOREIGN PATENT DOCUMENTS

EP    1546327    1/2012

OTHER PUBLICATIONS

Ban et al. Current Strategies and Challenges for Purification of Cardiomyocytes Derived from Human Pluripotent Stem Cells, Theranostics 2017, 7(7):2067-2077.
Ban et al. "Abstract 16384: Isoproteronol Facilitated Cardiomyocyte Generation From Human Pluripotent Stem Cells" Circulation, 2011; 124: A16384.
Ban et al. "Purification of Cardiomyocytes From Differentiating Pluripotent Stem Cells UsingMolecular Beacons That Target Cardiomyocyte-Specific mRNA" Circulation, 2013; 128: 1897-1909.
Ban et al. "Non-genetic Purification of Ventricular Cardiomyocytes from Differentiating Embryonic Stem Cells through Molecular Beacons Targeting IRX-4" Stem Cell Reports, 2015; 5: 1239-1249.
Berstein et al. "Stem cell therapy for cardiac disease, Pediatric Research" 2012, 71; 491-499.
Braam et al. "Cardiomyocytes from human pluripotent stem cells in regenerative medicine and drug discovery" Trends Pharmacol Sci., 2009; 30(10): 536-545.
Bu et al. "Human ISL 1 heart progenitors generate diverse multi potent cardiovascular cell lineages" Nature, 2009; 460:113-117.
Dubois et al. "SIRPA is a specific cell-surface marker for isolating cardiomyocytes derived from human pluripotent stem cells" Nature Biotechnology, 2011; 29(11): 1011.
Elliott et al. "NKX2-5eGFP/w hESCs for isolation of human cardiac progenitors and cardiomyocytes" Nature Methods, 2011; 8(12): 1039.
Hattori et al. "Nongenetic method for purifying stem cell-derived cardiomyocytes" Nature Methods, 2010; 7(1): 61.
Huber et al. "Identification and selection of cardiomyocytes during human embryonic stem cell differentiation" FASEB J., 2007; 21(10): 2551-2563.
Jones et al. "Molecular beacons can assess changes in expression and 3'-polyadenylation of human eNOS mRNA" Am J Physiol Cell Physiol., 2009; 296: C498-504.
Kattman et al. "Stage-Specific Optimization of Activin/Nodal and BMP Signaling Promotes Cardiac Differentiation of Mouse and Human Pluripotent Stem Cell Lines" Cell Stem Cell., 2011; 8(2): 228-240.
King et al. "High-Throughput Tracking of Pluripotent Human Embryonic Stem Cells with Dual Fluorescence Resonance Energy Transfer Molecular Beacons" Stem Cells and Development, 2011; 20(3): 475.
Larsson et al. "Sorting Live Stem Cells Based on Sox2 mRNA Expression" PLoS ONE, 2012; 7(11): e49874.
NCBI Gene ID: 4619, MYH1, myosin, heavy chain 1, skeletal muscle, adult [*Homo sapiens* (human)], updated May 12, 2016, printed as pp. 1/7-7/7 on May 27, 2016.
NCBI Gene ID: 4624, MYH6, myosin, heavy chain 6, cardiac muscle, alpha [*Homo sapiens* (human), updated May 22, 2016, printed as pp. 1/11-11/11 on May 27, 2016.
NCBI Gene ID: 4625, MYH7, myosin, heavy chain 7, cardiac muscle, beta [*Homo sapiens* (human)], updated May 15, 2016, printed as pp. 1/11-11/11 on May 27, 2016.
Nitin et al. NLS peptide conjugated molecular beacons for visualizing nuclear RNA in living cells Bioconjug Chem., 2008;19:2205-2211.
Rhee et al. "Simultaneous detection of mRNA and protein stem cell markers in live cells" BMC Biotechnology, 2009; 9: 30.
Santangelo et al. "Nanostructured Probes for RNA Detection in Living Cells" Annals of Biomedical Engineering, 2006; 34(1): 39-50.

(Continued)

*Primary Examiner* — Jennifer Dunston
(74) *Attorney, Agent, or Firm* — Emory Patent Group

(57) ABSTRACT

This disclosure is in the area of research and therapeutics. In certain embodiments, it provides methods to assist in the purification of cell mixtures, e.g., cardiomyocytes, using molecular beacons targeting cell-type specific RNA, e.g. mRNA.

11 Claims, 23 Drawing Sheets

(56) References Cited

OTHER PUBLICATIONS

Seligman et al. "A method for isolating pluripotent/multipotent stem cells from blood by using the pluripotent and germ-line DAZL gene as a marker" Stem Cells Dev., 2009;18(9): 1263-1271.

Shiba et al. "Human ES-cell-derived cardiomyocytes electrically couple and suppress arrhythmias in injured hearts" Nature, 2012; 489(7415): 322-325.

Tyagi et al. "Molecular beacons: probes that fluoresce upon hybridization" Nat Biotechnol, 1996; 14(3): 303-308.

Uosaki et al. "Efficient and scalable purification of cardiomyocytes from human embryonic and induced pluripotent stem cells by VCAM1 surface expression" PLoS One, 2011; 6(8): e23657.

Van Hoof "Identification of Cell Surface Proteins for Antibody-Based Selection of Human Embryonic Stem Cell-Derived Cardiomyocytes" Journal of Proteome Research, 2010; 9: 1610-1618.

Yang et al. "Human cardiovascular progenitor cells develop from a KDR+ embryonic-stem-cell-derived population" Nature, 2008; 453: 524-528.

Zwi et al. "Cardiomyocyte differentiation of human induced pluripotent stem cells" Circulation, 2009; 120(15): 1513-1523.

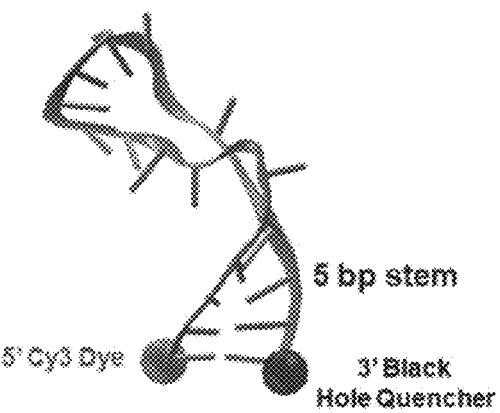
FIG. 1A
FIG. 1B
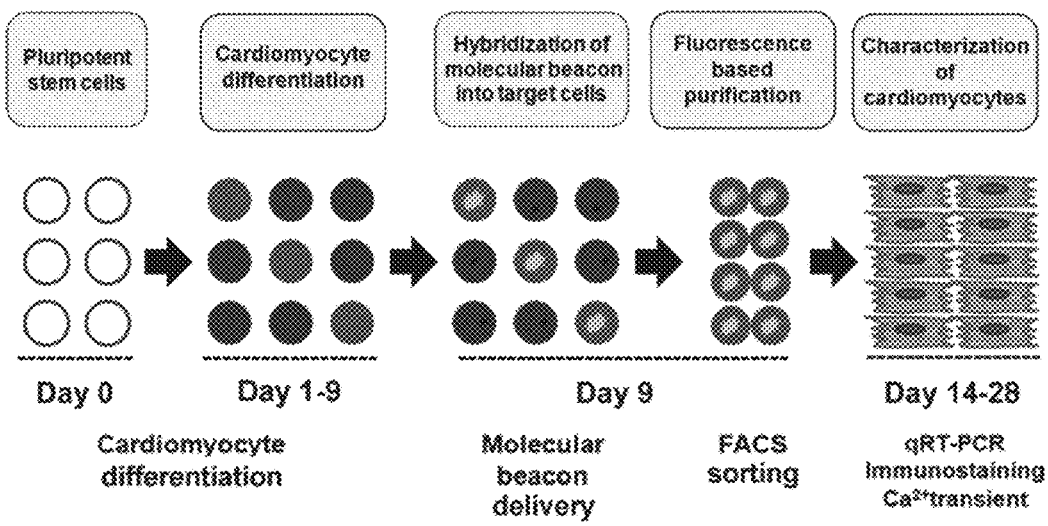
FIG. 2

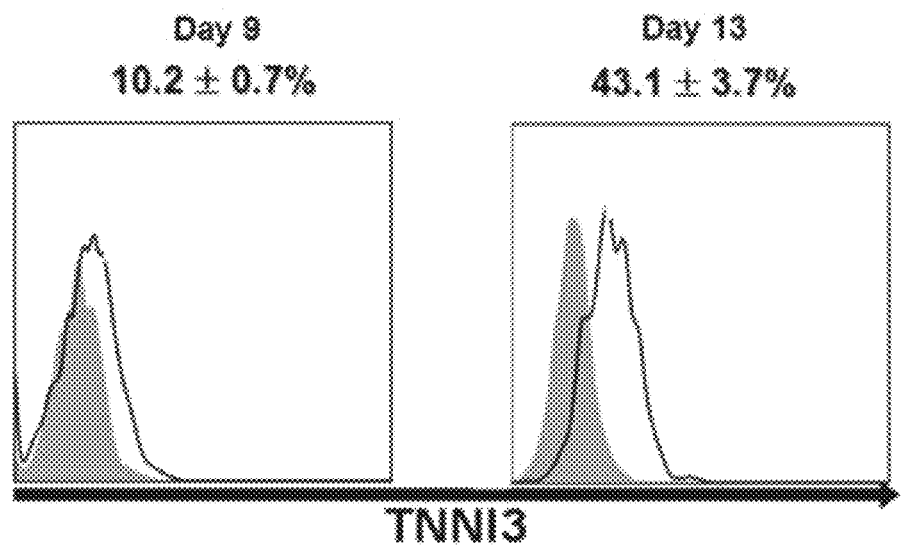
FIG. 5B
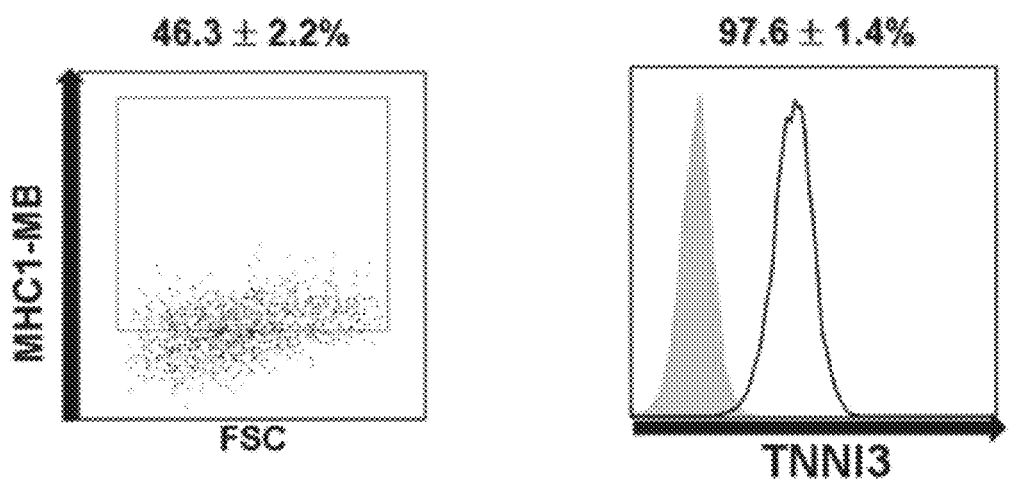
FIG. 5C
FIG. 5D

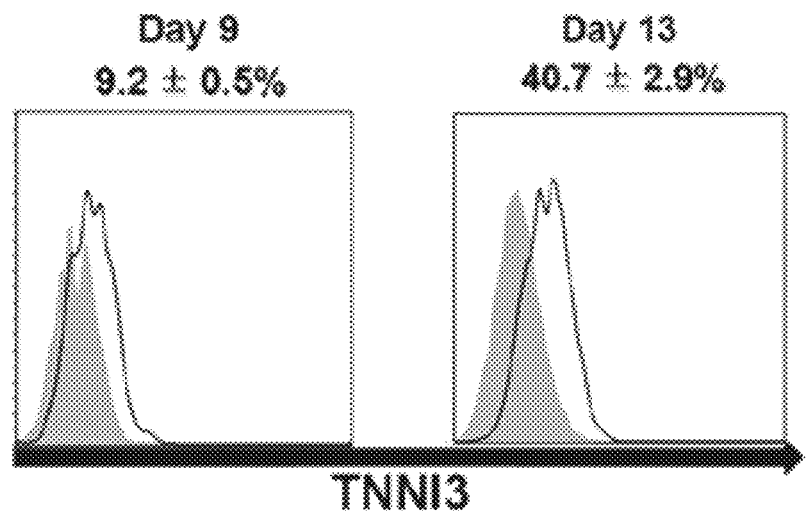
FIG. 6B
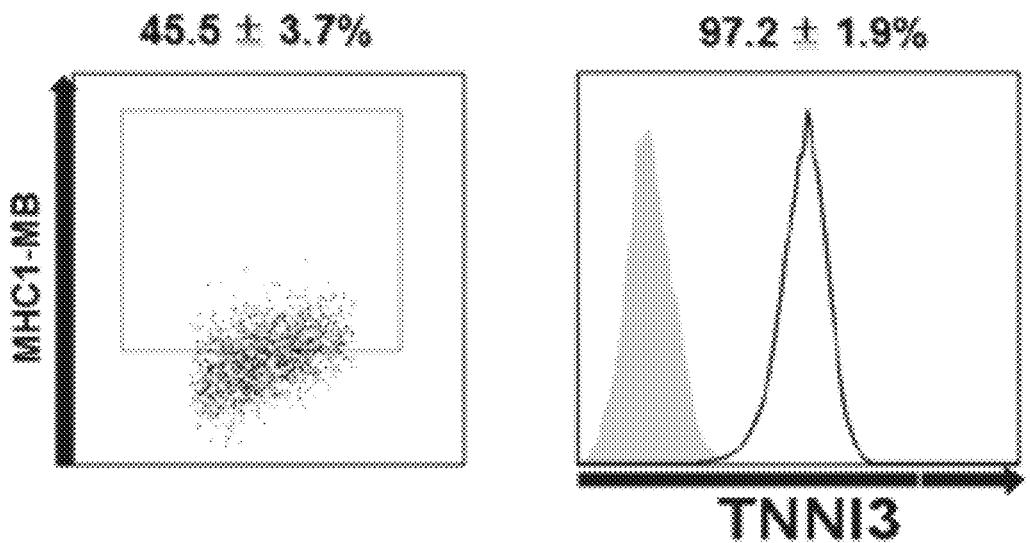
FIG. 6C
FIG. 6D

SEQUENCE LISTING

```
<160> NUMBER OF SEQ ID NOS: 24

<210> SEQ ID NO 1
<211> LENGTH: 27
<212> TYPE: DNA
<213> ORGANISM: Artificial
<220> FEATURE:
<223> OTHER INFORMATION: synthetic

<400> SEQUENCE: 1
ccctgacgta aactttatgc ttcaggg                                              27

<210> SEQ ID NO 2
<211> LENGTH: 15
<212> TYPE: DNA
<213> ORGANISM: Artificial
<220> FEATURE:
<223> OTHER INFORMATION: synthetic

<400> SEQUENCE: 2
cgtaaacttt atgct                                                          15

<210> SEQ ID NO 3
<211> LENGTH: 24
<212> TYPE: DNA
<213> ORGANISM: Artificial
<220> FEATURE:
<223> OTHER INFORMATION: synthetic

<400> SEQUENCE: 3
cctccatctt cttcttcacg gagg                                                24

<210> SEQ ID NO 4
<211> LENGTH: 14
<212> TYPE: DNA
<213> ORGANISM: Artificial
<220> FEATURE:
<223> OTHER INFORMATION: synthetic

<400> SEQUENCE: 4
atcttcttct tcac                                                           14

<210> SEQ ID NO 5
<211> LENGTH: 6
<212> TYPE: DNA
<213> ORGANISM: Artificial
<220> FEATURE:
<223> OTHER INFORMATION: synthetic

<400> SEQUENCE: 5
```

```
ccctga                                                              6

<210> SEQ ID NO 6
<211> LENGTH: 6
<212> TYPE: DNA
<213> ORGANISM: Artificial
<220> FEATURE:
<223> OTHER INFORMATION: synthetic

<400> SEQUENCE: 6 tcaggg                                                              6

<210> SEQ ID NO 7
<211> LENGTH: 5
<212> TYPE: DNA
<213> ORGANISM: Artificial
<220> FEATURE:
<223> OTHER INFORMATION: synthetic

<400> SEQUENCE: 7 cctcc                                                               5

<210> SEQ ID NO 8
<211> LENGTH: 5
<212> TYPE: DNA
<213> ORGANISM: Artificial
<220> FEATURE:
<223> OTHER INFORMATION: synthetic

<400> SEQUENCE: 8 ggagg                                                               5

<210> SEQ ID NO 9
<211> LENGTH: 23
<212> TYPE: DNA
<213> ORGANISM: Artificial
<220> FEATURE:
<223> OTHER INFORMATION: synthetic

<400> SEQUENCE: 9
cccaagatcc ccgatggaga gag                                          23

<210> SEQ ID NO 10
<211> LENGTH: 21
<212> TYPE: DNA
<213> ORGANISM: Artificial
<220> FEATURE:
<223> OTHER INFORMATION: synthetic

<400> SEQUENCE: 10
agaaccgcct ggctgaagag a                                            21

<210> SEQ ID NO 11
<211> LENGTH: 20
<212> TYPE: DNA
<213> ORGANISM: Artificial
<220> FEATURE:
<223> OTHER INFORMATION: synthetic

<400> SEQUENCE: 11
gaacaggagg aaggctgagg                                              20

<210> SEQ ID NO 12
<211> LENGTH: 19
<212> TYPE: DNA
```

<213> ORGANISM: Artificial
<220> FEATURE:
<223> OTHER INFORMATION: synthetic

<400> SEQUENCE: 12
gtgaagaaga agatggagg      19

<210> SEQ ID NO 13
<211> LENGTH: 23
<212> TYPE: DNA
<213> ORGANISM: Artificial
<220> FEATURE:
<223> OTHER INFORMATION: synthetic

<400> SEQUENCE: 13
aagagccggg acattggtgc caa      23

<210> SEQ ID NO 14
<211> LENGTH: 29
<212> TYPE: DNA
<213> ORGANISM: Artificial
<220> FEATURE:
<223> OTHER INFORMATION: synthetic

<400> SEQUENCE: 14
taccctctct ccatcgggga tcttgggta      29

<210> SEQ ID NO 15
<211> LENGTH: 29
<212> TYPE: DNA
<213> ORGANISM: Artificial
<220> FEATURE:
<223> OTHER INFORMATION: synthetic

<400> SEQUENCE: 15
ccctctcttc agccaggcgg ttctgaggg      29

<210> SEQ ID NO 16
<211> LENGTH: 28
<212> TYPE: DNA
<213> ORGANISM: Artificial
<220> FEATURE:
<223> OTHER INFORMATION: synthetic

<400> SEQUENCE: 16
atcctcagcc ttcctcctgt tcgaggat      28

<210> SEQ ID NO 17
<211> LENGTH: 28
<212> TYPE: DNA
<213> ORGANISM: Artificial
<220> FEATURE:
<223> OTHER INFORMATION: synthetic

<400> SEQUENCE: 17
ttggcaccaa tgtcccggct cttgccaa      28

<210> SEQ ID NO 18
<211> LENGTH: 33
<212> TYPE: DNA
<213> ORGANISM: Artificial
<220> FEATURE:
<223> OTHER INFORMATION: synthetic

<400> SEQUENCE: 18
cacctagttt tgttatatta gcctccctag gtg      33

```
<210> SEQ ID NO 19
<211> LENGTH: 28
<212> TYPE: DNA
<213> ORGANISM: Artificial
<220> FEATURE:
<223> OTHER INFORMATION: synthetic

<400> SEQUENCE: 19
caggcagaga gtagaaagca gatgcctg                                            28

<210> SEQ ID NO 20
<211> LENGTH: 29
<212> TYPE: DNA
<213> ORGANISM: Artificial
<220> FEATURE:
<223> OTHER INFORMATION: synthetic

<400> SEQUENCE: 20
acgacgcgac aagcgcaccg atacgtcgt                                           29

<210> SEQ ID NO 21
<211> LENGTH: 22
<212> TYPE: DNA
<213> ORGANISM: Artificial
<220> FEATURE:
<223> OTHER INFORMATION: synthetic

<400> SEQUENCE: 21
agggaggcta atataacaaa ac                                                  22

<210> SEQ ID NO 22
<211> LENGTH: 23
<212> TYPE: DNA
<213> ORGANISM: Artificial
<220> FEATURE:
<223> OTHER INFORMATION: synthetic

<400> SEQUENCE: 22
ccctgaagca taaagtttac gtc                                                 23

<210> SEQ ID NO 23
<211> LENGTH: 23
<212> TYPE: DNA
<213> ORGANISM: Artificial
<220> FEATURE:
<223> OTHER INFORMATION: synthetic

<400> SEQUENCE: 23
aggcatctgc tttctactct ctg                                                 23

<210> SEQ ID NO 24
<211> LENGTH: 20
<212> TYPE: DNA
<213> ORGANISM: Artificial
<220> FEATURE:
<223> OTHER INFORMATION: synthetic

<400> SEQUENCE: 24
gtatcggtgc gcttgtcgcg                                                     20
```

PURIFICATION OF CELL MIXTURES USING MOLECULAR BEACONS TARGETING CELL SPECIFIC RNA

CROSS REFERENCE TO RELATED APPLICATIONS

This Application is a division of U.S. application Ser. No. 14/211,430 filed Mar. 14, 2014, which claims priority to U.S. Provisional Application No. 61/787,364 filed Mar. 15, 2013. The entirety of each of these applications is hereby incorporated by reference for all purposes.

STATEMENT REGARDING FEDERALLY FUNDED RESEARCH

This invention was made with government support under Grant Number HHSN-268201000043C awarded by the National Institutes of Health. The government has certain rights in the invention.

INCORPORATION BY REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 12147USDIV_2016-09-22_ST25.txt. The text file is 5 KB, was created on Sep. 22, 2016, and is being submitted electronically via EFS-Web.

FIELD

This disclosure is in the area of research and therapeutics. In certain embodiments, it provides methods to assist in the purification of cell mixtures, e.g., cardiomyocytes, using molecular beacons targeting cell-type specific RNA, e.g. mRNA.

BACKGROUND

Heart disease is the leading cause of death globally, killing 17.3 million people worldwide. It is also the leading cause of death among men and women in the United States accounting for more than half of the deaths reported in the US in 2009. Estimates from the CDC, suggest that heart failure alone costs the country $34.4 billion annually in medication, health care, and loss in productivity.

Heart failure occurs when a loss of cardiac muscle tissue impairs heart function leading to an inability to sufficiently pump oxygenated blood to other parts of the body. Cardiac tissue can be damaged by myocardial infarction or a heart attack, when the blood supply to the heart is lost resulting in the damage or death of impacted tissue. Unfortunately, these conditions cannot be reversed. However, cardiac regenerative medicine offers promising therapies that can improve heart function and health.

Human pluripotent stems cells can now be differentiated into cardiomyocytes, which can be transplanted or grafted into patients following cardiac damage. Recent reports have demonstrated certain methods for the inducing the differentiation of human induced pluripotent stem cells and human embryonic stem cells into cardiomyocytes. Another method that has garnered attention recently is induced pluripotent stem cell (iPSC) technology. iPSC technology differentiates a pluripotent stem cell from a non-pluripotent stem cell, by inducing the expression of certain genes.

Protocols for cardiomyocyte differentiation generally yield a heterogeneous assortment of cardiomyocytes, undifferentiated cells and non-cardiomyocytes. Obtaining enriching or purifying cardiomyocyte preparations still remains challenging, diminishing the clinical utility of this technology. While the existing methods provide a level of cardiomyocyte purity suitable for research purposes, none of these are suitable for clinical applications. It is known that transplanting a mixed population of cardiovascular cells into patients can lead to an adverse outcome such as teratoma formation or other abnormal growths.

Tyagi et al. report molecular beacons as probes that fluoresce upon hybridization. See Nature Biotechnology, 1996, 14(3):303-8.

Braam et al. report cardiomyocytes from human pluripotent stem cells in regenerative medicine and drug discovery. See Trends in Pharmacological Science, 2009, 30, 536-545.

Seligman et al. reports a method for isolating pluripotent/multipotent stem cells from blood by using the pluripotent and germ-line DAZL gene as a marker. Stem Cells and Development, 2009, 18(9): 1263-1271. See also U.S. Pat. No. 6,692,965

King et al. report high-throughput tracking of pluripotent human embryonic stem cells with dual fluorescence resonance energy transfer molecular beacons. See Stem Cells Dev, 2011, 20(3): 475-484.

Larsson et al. report sorting live stem cells based on Sox2 mRNA expression. See PLoS ONE, 2012, 7(11): e49874.

Elliott et al reports NKX2-5eGFP/w hESCs for isolation of human cardiac progenitors and cardiomyocytes. See Nature Methods, 2011, 8 1037-1040.

Uosaki et al. report purification of cardiomyocytes from human embryonic and induced pluripotent stem cells by VCAM1 surface expression. See PLoS ONE, 2011, 6:e23657. Dubois et al. report SIRPA is a specific cell-surface marker for isolating cardiomyocytes derived from human pluripotent stem cells. See Nature Biotechnology, 2011, 29:1011-1018.

Yang et al. report human cardiovascular progenitor cells develop from a KDR+ embryonic-stem-cell-derived population. See Nature, 2008, 453:524-528.

Kattman et al. report stage-specific optimization of activin/nodal and bmp signaling promotes cardiac differentiation of mouse and human pluripotent stem cell lines. See Cell Stem Cell, 2011, 8:228-240.

Bu et al. report human ISL1 heart progenitors generate diverse multipotent cardiovascular cell lineages. See Nature, 2009, 460:113-117.

Huber et al. report identification and selection of cardiomyocytes during human embryonic stem cell differentiation. See Faseb Journal, 2007, 21:2551-2563.

Zwi et al. report cardiomyocyte differentiation of human induced pluripotent stem cells. Circulation, 2009, 120:1513-1523.

Shiba et al. report human es-cell-derived cardiomyocytes electrically couple and suppress arrhythmias in injured hearts. Nature, 2012, 489(7415):322-5

U.S. Pat. No. 8,039,259 reports buffering solutions for electroporation.

References cited herein are not an admission of prior art.

SUMMARY

In certain embodiments, the disclosure relates to methods for purifying cell mixtures comprising, a) mixing a molecular beacon, e.g., a nucleobase polymer with a double stranded segment, such as in a hairpin, wherein one strand of the double stranded segment is conjugated to a fluorescent dye and the other strand is conjugated a quencher, wherein the florescent dye and quencher are configured such that the fluorescent dye is quench while the nucleobase polymer is double stranded, wherein the nucleobase polymer comprises a segment that hybridizes to a target nucleic acid (e.g. RNA, mRNA, microRNA) with a cell mixture, under conditions such that the nucleobase polymer hybridizes to the nucleic acid in the target cell of the mixture, and does not bind all of the cells in the mixture, under conditions such that the fluorescent dye is no longer quenched by the quencher providing a fluorescent cell; and b) separating the fluorescent cell, e.g., molecular beacon bound fluorescent cardiomyocytes, by fluorescence activated cells sorting providing a purified composition of fluorescent cells, e.g., cardiomyocytes and a composition of non-fluorescent cells removed of target cells.

In certain embodiments, the target nucleic acid is a unique sequence of RNA with wholly or partial single stranded secondary structure, e.g., within hairpin loops, bulges, internal loops, and tails.

In certain embodiments, the method further comprises c) replicating and/or further purifying the fluorescent cells to provide a substantial homogenous mixture of cells of a specific type. In certain embodiments, the method further contemplates negative selection and replicating and/or further purifying the non-fluorescent cells to provide a substantial homogenous mixture of cells of a specific type.

In certain embodiments, the disclosure contemplates that the target RNA is a mRNA or transcription factor RNA of a human stem cell-derived cardiomyocytes to provide purified compositions of human cardiac cells.

In certain embodiments, the disclosure contemplates methods disclosed herein for the target RNA associated with neuronal cells or pancreatic β-cells, and for isolation of other cell types from pluripotent stem cells or induced pluripotent stem cells.

In certain embodiments, the double stranded nucleic acid hybridizes to the target RNA in a cell of the mixture such that it hybridizes to less than 90, 80, 70, 60, 50, 40, 30, 25, 20, 15, 10, 5, 4, 3, 2, 1, or 0.5% of the total cells in the mixture.

In certain embodiments, the disclosure relates to using methods disclosed herein to provide a substantial homogenous mixture of cells of a specific type that is greater than greater than 50, 60, 70, 80, 90, or 91% of the total cells.

In certain embodiments, the disclosure relates to using methods disclosed herein to provide ventricular type cardiomyocytes of greater than 50, 60, 70, 80, 90, or 91% of the total cells.

In further embodiments, the disclosure contemplates compositions and methods of generating purified composition of cardiomyocytes or cardiomyocyte precursor cells, e.g. ventricular or atrial cardiomyocytes or cardiomyocyte precursor cells, prior to mixing with molecular beacons for purification. In certain embodiments, contemplated cell mixtures include enriched cardiomyocytes generated from embryonic stem cells, e.g., derived from the inner cell mass of a blastocyst, an early-stage embryo, umbilical cord cells, cord blood, induced pluripotent stem cells of a human, bone marrow, peripheral blood.

In further embodiments, the disclosure contemplates compositions and methods of generating purified composition of ventricular cardiomyocytes comprising mixing embryo bodies with ascorbic acid under conditions that mixtures of cardiomyocytes are formed and subsequently purifying the mixtures of cardiomyocytes by mixing with molecular beacons using methods disclosed herein.

In further embodiments, the disclosure contemplates prior to after separating the fluorescent cells exposing the purified composition of fluorescent cells or replicated florescent cells to a second fluorescent molecule, e.g. fluorescently tagged antibody or second molecular beacon, providing a cell conjugated with a second fluorescent molecule and separating the cell conjugated with a second fluorescent molecule by fluorescence activated cell sorting.

In certain embodiments, the cells mixtures are samples from a human subject. In certain embodiments, the cells mixtures are peripheral blood cells that have been enriched in $CD31^+$ and/or $CD34^+$ cells. In certain embodiments, the cells mixtures are peripheral blood cells wherein the subject was prior to sampling, administered a monoclonal antibody against the protein CD20, such as rituximab, providing a peripheral blood cell mixture in which B cells have been reduced.

In certain embodiments, the nucleobase polymers comprises or 15-40 nucleobases or 20-30 nucleobases with a fluorophore conjugated to the 5' end and a quencher at the 3' end, with 4-7 bps at the 5' end which are complementary to the bps at the 3' end. This self-complementary configuration induces the oligonucleotides to form a stem-loop (hairpin) structure so that the fluorophore and the quencher are within close proximity (<7, 10, or 15 nm) and fluorescence is quenched. Hybridization of the molecular beacons (MBs) with the target mRNA opens the hairpin structure and physically separates the fluorophore from the quencher, allowing a fluorescence signal to be emitted upon excitation.

In certain embodiments, the disclosure relates to molecular beacons that target human Iroquois homeobox protein 4 (IRX4), e.g., NCBI Reference Sequences: NM_001278632.1, NM_001278633.1, NM_001278634.1, NM_001278635.1, or NM_016358.2.

In certain embodiments, the disclosure relates to a molecular beacon comprising nucleic acid that targets IRX4 having (SEQ ID NO: 1) CCCTGACGTAAACTTTATGCT TCAGGG or (SEQ ID NO:2) CGTAAACTTTATGCT of SEQ ID NO: 1, or variants thereof with greater than 50, 60, 70, 80, 85, 90, or 95% sequence identity thereto. In certain embodiments, the disclosure contemplates a molecular beacon hairpin nucleobase polymer, nucleic acid, probe conjugated or linked to a fluorescent molecule and quencher having a loop sequence, e.g., (SEQ ID NO:2) CGTAAACTTTATGCT of SEQ ID NO: 1, of between 8 and 25 nucleobases, or 10 to 20 nucleobases, or 11 to 17 nucleobases that hybridize to a target cell sequence, and herein the hairpin comprises a reverse complement, or palindrome sequence, e.g., the (SEQ ID NO: 5) CCCTGA and (SEQ ID NO: 6) TCAGGG of SEQ ID NO: 1 having 6 nucleobase pairs, or 3 to 20 nucleobase pairs, or 4 to 10 nucleobase pairs, or 4 to 7 nucleobase pairs, wherein the loop sequence and palindrome sequence are configured such they will emit a fluorescence signal when hybridized to target mRNAs.

In certain embodiments, the disclosure relates to a molecular beacon comprising (SEQ ID NO: 3) CCTC-CATCTTCTTCTTCACGGAGG or (SEQ ID NO:4) ATCT-TCTTCTTCAC of SEQ ID NO: 3 or variants thereof with greater than 50, 60, 70, 80, 85, 90, or 95% sequence identity thereto. In certain embodiments, the disclosure contemplates a molecular beacon hairpin nucleobase polymer, nucleic acid, probe conjugated or linked to a fluorescent molecule and quencher having a loop sequence, e.g., (SEQ ID NO:4)

ATCTTCTTCTTCAC of SEQ ID NO: 3, of between 8 and 20 nucleobases, or 10 to 17 nucleobases, or 11 to 15 nucleobases that hybridize to a target cell sequence, and herein the hairpin comprises a reverse complement, or palindrome sequence, e.g., the (SEQ ID NO: 7) CCTCC and (SEQ ID NO: 8) GGAGG of SEQ ID NO: 3 having 5 nucleobase pairs, of 3 to 20 nucleobase pairs, or 4 to 10 nucleobase pairs, or 4 to 7 nucleobase pairs, wherein the loop sequence and palindrome sequence are configured such they will emit a fluorescence signal when hybridized to target mRNAs.

In certain embodiments, the disclosure contemplates mixing the cell mixtures and nucleic acids by electroporation wherein electric pulses are employed to increase the permeability of the cell membrane and allow uptake of the nucleic acid molecules with buffering solutions that stabilize the cells in the electric field.

In certain embodiments, the buffer solution includes at least one saccharide or salt thereof, e.g., sodium succinate, mannitol, and sodium lactobionate and/or the solution 4-6 mM KCl, 10-20 mM $MgCl_2$, 5-25 mM HEPES, 50-160 mM $Na_2HPO_4/NaH_2PO_4$ (at a pH of about 7-8).

In certain embodiments, this disclosure relates to the purification of pluripotent stem cell (PSC) derived cardiomyocytes from a heterogeneous mixture of differentiating cells using molecular beacons. Molecular beacons target a gene specifically expressed in cardiomyocytes and allow recognition of this targeting typically through fluorescence. This disclosure provides a method for purifying cardiomyocytes that comprises, a) introducing of a molecular beacon that targets cardiomyocyte specific mRNA to a mixture of differentiating pluripotent cells under conditions where the beacon hybridizes to the cardiomyocyte specific mRNA, thus providing beacon-bound fluorescent cardiomyocytes, and b) purifying the beacon-bound fluorescent cardiomyocytes thus providing a purified population of cardiomyocytes. In some embodiments, the method further includes c) generating a cell line expressing said mRNA of interest by growing the purified population of cardiomyocytes.

In certain aspects, the disclosure relates to a method for the differentiation of pluripotent stem cells into a cardiomyocyte population that comprises a) the expansion of undifferentiated PSCs by culturing cells in a monolayer in MTESR® media, b) induction of mesodermal differentiation through application of bone morphogenetic protein 4 (BMP4), Activin A, and fibroblast growth factor 2 (FGF2) to hPSCs, c) induction of cardiac lineage differentiation by the supplementation with conditioned media, and d) continuous treatment with β-adrenergic receptor agonist isoproterenol to generate spontaneous beating cardiomyocytes.

In certain embodiments, the molecular beacon includes a nucleic acid sequence complementary to a cardiomyocyte specific mRNA and a fluorescent probe. In other embodiments, the molecular beacon includes an antisense oligonucleotide to a cardiomyocyte specific mRNA. In certain embodiments this antisense oligonucleotide is complementary to myosin heavy chain (MHC1), myosin heavy chain 2 (MHC2), troponin T 1 (TNT1), troponin T 2 (TNT2), troponin T 3 (TNT3) or any cardiomyocyte specific RNA sequence.

In some embodiments, the beacon contains a fluorescent emitter configured at one end and a quencher configured on the other, wherein in the absence of complementary sequences the probe folds forming a hairpin structure, causing the fluorophore to be quenched and not emit fluorescence upon excitation, and wherein in the presence of complementary mRNA target, the emitter fluoresces upon excitation.

In certain embodiments, the fluorescent emitter is Cy3 fluorophore. In certain embodiments and the quencher is a BLACK HOLE QUENCHER® 2 (BHQ). In some embodiments, the emitter is on the 5' end of the beacon and the quencher is on the 3' end of the beacon.

In certain aspects the pluripotent cells are mammalian cells and in more specific embodiments, are human cells.

In other embodiments an enriched population of cardiomyocytes derived from pluripotent stem cells is provided, which is generated by a method that comprises, a) introducing a molecular beacon that targets cardiomyocyte specific mRNA to a mixture of differentiating pluripotent cells under conditions wherein the beacon hybridizes to the cardiomyocyte specific mRNA providing probe bound fluorescent cardiomyocytes, b) purifying the beacon bound fluorescent cardiomyocytes by fluorescence activated cells sorting, thus providing a purified population of cardiomyocytes, wherein the cardiomyocytes in the purified population are present in greater than 70%, 80%, 90%, 95%, or 98% purity of the population of cells.

In certain aspects this disclosure relates to a purified composition of cardiomyocytes, purified by a method that comprises, a) introducing a molecular beacon that targets cardiomyocyte specific mRNA to a mixture of differentiating pluripotent cells under conditions the beacon hybridizes to the cardiomyocyte specific mRNA providing beacon bound fluorescent cardiomyocytes, b) purifying the beacon bound fluorescent cardiomyocytes by fluorescence activated cell sorting thus providing a purified population of cardiomyocytes, wherein the purified composition of cardiomyocytes have more than 50% of cells staining positive for ACTN2, TNNT2, and TNNI3 by immunochemistry and exhibit cardiomyocyte morphology. In certain embodiments, at least 60%, or at least 70%, or at least 80%, or at least 90% or at least 95% or at least 98% stain positive.

In other embodiments the purified composition of cardiomyocytes has more than 50% of cells, or, at least 60%, or at least 70%, or at least 80%, or at least 90% or at least 95% or at least 98% of cells exhibiting expression of cardiomyocyte specific genes comprising, TNNT2, MYH6, MYH7, and MYL2. In certain embodiments the purified composition of cardiomyocytes have more than 50% of cells exhibiting a decrease expression of genes comprising, genes specific to smooth muscle cells (CALPONIN), fibroblast (THY1), skeletal myocyte (MYOD), neural lineages (NEUROD) and endothelial cells (PECAM1). In other embodiments the purified composition of cardiomyocytes has more than 50% of cells that exhibit spontaneous contraction and rhythmic calcium oscillation. In certain embodiments, at least 60%, or at least 70%, or at least 80%, or at least 90% or at least 95% or at least 98% exhibit such contraction and oscillation.

In certain embodiments, this disclosure relates to a kit comprising a molecular beacon that targets cardiomyocyte specific RNA, wherein the molecular beacon is an antisense oligonucleotide comprising a fluorescent emitter at one end, and quencher configured at the other, wherein the absence of the cell specific mRNA, the probe does not fluoresce, wherein the presence of complementary cell specific mRNA the probe is configured to fluoresce, wherein the antisense oligonucleotide is complementary to myosin heavy chain 1 (MHC1), myosin heavy chain 2 (MHC2), troponin T 1 (TNT1), troponin T 2 (TNT2), troponin T 3 (TNT3) or any cardiomyocyte specific mRNA sequence.

In certain embodiments, this disclosure relates to identifying a cardioactive agent comprising contacting a cardiomyocyte population with a test agent, wherein the cardiomyocyte population is produced herein by methods comprising, a) expanding undifferentiated PSCs by culturing cells in a monolayer under in MTESR® media, b) inducing mesodermal differentiation through application of bone morphogenetic protein 4 (BMP4), Activin A, and fibroblast growth factor 2 (FGF2) to PSCs, c) inducing cardiac lineage differentiation by the supplementation with conditioned media, and d) the continuous treatment with β-adrenergic receptor agonist isoproterenol to generate spontaneous beating cardiomyocytes; e) introducing a molecular beacon that targets cardiomyocyte specific mRNA to a mixture of differentiating pluripotent cells under conditions the molecular hybridizes to the cardiomyocyte specific mRNA providing probe bound fluorescent cardiomyocytes, f) purifying the probe bound fluorescent cardiomyocytes by fluorescence activated cells sorting (FACS) thus providing a purified population of cardiomyocytes, g) generating a cell line expressing said mRNA of interest by growing purified composition of cardiomyocytes wherein determining if the test agent modulates an activity or function of cardiomyocytes within the population identifies the test agent as a cardioactive agent.

In other embodiments this disclosure relates to generating a purified cardiomyocyte population for research purposes to be used as a model system for studying cardiac cells. In certain aspects the disclosure relates to isolating cardiac cells for experimental protocols that require the increased number or function of cardiomyocytes comprising a) introducing a molecular beacon that targets cardiomyocyte specific mRNA to a mixture of differentiating pluripotent cells under conditions the molecular hybridizes to the cardiomyocyte specific mRNA providing probe bound fluorescent cardiomyocytes, b) purifying the probe bound fluorescent cardiomyocytes by fluorescence activated cells sorting (FACS) thus providing a purified population of cardiomyocytes, c) generating a cell line expressing said mRNA of interest by growing purified composition of cardiomyocytes.

In certain embodiments, this disclosure relates to the treatment of a subject suffering from the damage or death of cardiac cells wherein the said subject is in need of an increased number or function of cardiomyocytes, wherein the treatment comprises transplanting or grafting a cardiomyocyte population into the said subject, wherein the cardiomyocyte population is produced by a method comprising a) differentiation of pluripotent stem cells into beating cardiomyocytes, b) the introduction of a molecular beacon that targets cardiomyocyte specific mRNA to a mixture of differentiating pluripotent cells under conditions the probe hybridizes to the cardiomyocyte specific mRNA providing probe bound fluorescent cardiomyocytes, c) purifying the probe bound fluorescent cardiomyocytes by fluorescence activated cell sorting thus providing a purified population of cardiomyocytes, d) generating a cell line expressing said mRNA of interest by growing purified composition of cardiomyocytes wherein the molecular beacon is an antisense oligonucleotide complementary to myosin heavy chain 1 (MHC1), myosin heavy chain 2 (MHC2), troponin T 1 (TNT1), troponin T 2 (TNT2), troponin T 3 (TNT3) or any cardiomyocyte specific mRNA sequence, wherein the molecular beacon comprises a fluorescent emitter at one end, and quencher configured at the other, wherein the molecular beacon hybridizes to target sequence in the presence of the complementary cardiomyocyte specific mRNA, and emits a fluorescent signal upon excitation, wherein the absence of complementary cardiomyocyte specific mRNA sequence the molecular beacon forms a stem loop quenching fluorescent signal.

BRIEF DESCRIPTION OF THE FIGURES

FIG. 1A illustrates the structure of cardiomyocyte-specific molecular beacons (MBs). A, Molecular dynamics model of an MB in the closed/unbound conformation. The close proximity of the 5' Cy3 dye and the 3' BLACK HOLE QUENCHER® allows for direct and FRET (Förster resonance energy transfer) quenching.

FIG. 1B illustrates a molecular dynamics model of an MB in the open/bound conformation. The distance between the 5' Cy3 dye and the 3' BLACK HOLE QUENCHER® increases greatly to prevent dye quenching. MHC1 MB indicates an MB that targeted myosin heavy chain 6/7 mRNA.

FIG. 2 illustrates a strategy to enrich human pluripotent stem cell-derived cardiomyocytes using molecular beacons that target cardiomyocyte-specific mRNA. FACS indicates fluorescence-activated cell sorting; and qRT-PCR, quantitative reverse-transcriptase polymerase chain reaction. The proximity of the 5' Cy3 dye and the 3' BHQ is small enough to allow FRET quenching.

FIG. 5B shows percent expression of TNNI3 at days 9 and 13 determined by flow cytometry during hESC differentiation into cardiomyocytes; n=3.

FIG. 5C shows flow cytometry results of MHC1-MB-positive cells in hESC differentiation culture at day 13; n=6. FSC indicates forward scatter; and MHC1-MB, an MB that targeted myosin heavy chain 6/7 mRNA.

FIG. 5D shows flow cytometry results showing TNNI3 expression of FACS-sorted MHC1-MB-positive cells.

FIG. 6B shows percent expression of TNNI3 at days 9 and 13 during hiPSC differentiation into cardiomyocytes determined by flow cytometry; n=3.

FIG. 6C shows flow cytometric analysis of MHC1-MB signals in hiPSC differentiation culture at day 13; n=6. MHC1-MB indicates an MB that targeted myosin heavy chain 6/7 mRNA.

FIG. 6D shows flow cytometric results showing TNNI3 expression of FACS-sorted hiPSCs at day 13 of differentiation after applying MHC1-MB. Numbers represent percentages of MB-positive cells (C, D). n=3.

DETAILED DESCRIPTION

Figure 3A:
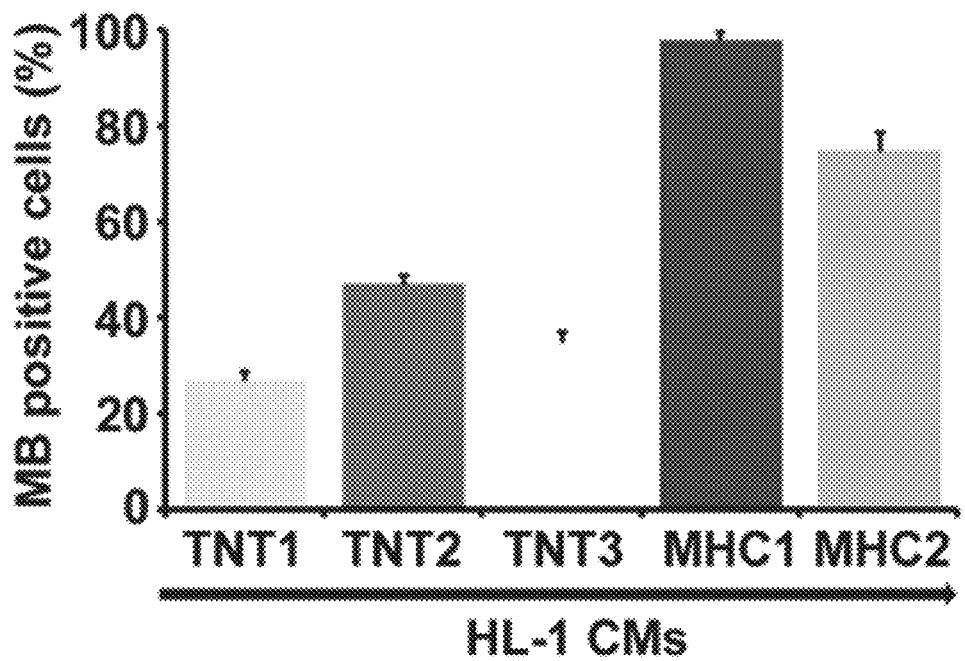
FIG. 3A shows data on the characterization of cardiomyocyte-specific molecular beacons (MBs). Flow cytometry results of 5 different MBs designed to detect cardiac troponin T or myosin heavy chain 6/7 mRNAs on HL-1 cardiomyocytes. An MB that targeted myosin heavy chain 6/7 mRNA, MHC1-MB, showed the highest detection rate. n=3.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs.

All references, publications, or information available on electronic databases are hereby incorporated by reference in their entirety.

It must be noted that, as used in the specification and the appended claims, the singular forms "a," "an," and "the" include plural referents unless the context clearly dictates otherwise. Thus, for example, reference to "a support" includes a plurality of supports.

The term "fluorescence-activated cell sorting" refers to a method of sorting a mixture of cells into two or more areas, typically one cell at a time, based upon the fluorescent characteristics of each cell, a respectively applied electrical charge, and separation by movement through an electrostatic field. Typically, a vibrating mechanism causes a stream of cells to break into individual droplets. Just prior to droplet formation, cells in a fluid pass through an area for measuring fluorescence of the cell. An electrical charging mechanism is configured at the point where the stream breaks into droplets. Based on the fluorescence intensity measurement, a respective electrical charge is imposed on the droplet as it breaks from the stream. The charged droplets then move through an electrostatic deflection system that diverts droplets into areas based upon their relative charge. In some systems, the charge is applied directly to the stream, and the droplet breaking off retains charge of the same sign as the stream. The stream is then returned to neutral after the droplet breaks off. In other systems, a charge is provided on a conduit inducing an opposite charge on the droplet.

The term "nucleobase polymer" refers to a polymer comprising nitrogen containing aromatic or heterocyclic bases that bind to naturally occurring nucleic acids through hydrogen bonding otherwise known as base pairing. A typical nucleobase polymer is a nucleic acid, RNA, DNA, combination, or chemically modified form thereof. A nucleic acid may be single or double stranded or both, e.g., they may contain overhangs. Nucleobase polymers may contain wholly or partially naturally occurring or synthetically modified bases and backbones. In certain embodiments, a nucleobase polymer need not be entirely complementary, e.g., may contain one or more insertions, deletions, or be in a hairpin structure provided that there is sufficient selective binding. Cytosine may be unmethylated or methylated, e.g., 5-methylcytosine.

In certain embodiments, a nucleobase polymer disclosed herein comprises monomers of phosphodiester, phosphorothioate, methylphosphonate, phosphorodiamidate, piperazine phosphorodiamidate, ribose, 2'-O-methyl ribose, 2'-O-methoxyethyl ribose, 2'-fluororibose, deoxyribose, 1-(hydroxymethyl)-2,5-dioxabicyclo[2.2.1]heptan-7-ol, P-(2-(hydroxymethyl)morpholino)-N,N-dimethylphosphonamidate, morpholin-2-ylmethanol, (2-(hydroxymethyl) morpholino) (piperazin-1-yl)phosphinate, or peptide nucleic acids or combinations thereof.

In certain embodiments, the nucleobase polymers are 8 to 25 base oligomers that mimic DNA or RNA. Many nucleobase polymers differ from native RNA or DNA in the chemical structure that links the four common bases. For example, a RNA may be modified wholly or partially to contain phosphorothioates instead of phosphodiester linkages. Nucleobase polymers that contain phosphorothioates may hybridize to RNA.

In certain embodiments, nucleobase polymers are contemplated to comprise peptide nucleic acids (PNAs). One example of a peptide nucleic acid is one that has 2-aminoethyl glycine linkages or similar analoges in place of the regular phosphodiester backbone. Other examples include d-lysPNA, argPNA, alternating units of 2-aminocyclopentanoic acid and pyrrolidine-2-carboxylic acid (pyrPNA). See Nielson, Chem & Biodiversity, 2010, 7:786.

In certain embodiments, nucleobase polymers are contemplated to comprise non-natural nucleobases such as, but not limited to, pseudoisocytosine as a substitute for cytosine, diaminopurine as a substitute for adenine, bicyclic thymine analogue (7Cl-bT), thiouracil, or combinations thereof.

In certain embodiments, nucleobase polymers are contemplated to comprise phosphorodiamidate morpholino oligomers (PMO). In certain embodiments, the nucleobase polymer comprises monomers of (2-(hydroxymethyl)morpholino)(piperazin-1-yl)phosphinate.

Purification of Pluripotent Stem Cell-Derived Cardiomyocytes Using Molecular Beacons In certain embodiments this disclosure relates to methods of transplanting or grafting purified stem cell derived cardiomyocytes into a host that require the increased number or function of healthy cardiomyocytes. In other embodiments this disclosure relates to the transplanting or grafting of stem cell derived cardiomyocytes into a host that suffer from loss or damage of cardiac tissue. In other aspects, this disclosure relates to the transplanting or grafting of purified stem cell derived cardiomyocytes into patients that suffer from heart disease including but not limited to heart failure, heart attack, coronary artery disease, cardiomyopathy, restrictive cardiomyopathy, or hypertrophic cardiomyopathy. In other aspects, this disclosure relates to a method that provides the purification of stem cell derived cardiomyocytes for research that requires the increased number of function of purified cardiomyocytes.

In certain aspects, this disclosure relates to a very efficient and specific method for purifying cardiomyocytes from differentiating mouse and human pluripotent stem cells by directly targeting mRNA of cardiomyocyte-specific genes using a molecular beacon followed by fluorescent activated cell sorting. The method provided herein purifies cardiomyocytes to a yield of greater than 50%, such as at least 60%, at least 65%, at last 70%, at least 75%, at least 80%, at least 85%, at least 90%, at least 95%, at least 96%, at least 97%, at least 98% or at least 99% purity of cardiomyocytes from differentiating PSCs.

The molecular beacon method has distinct advantages for isolating enriched populations of hPSC-derived cardiomyocytes. By enabling detection of specific sequences in the genes that are exclusively expressed in cardiomyocytes, the molecular beacon-based cell isolation technique minimizes the potential of contamination by other cells, which is a main concern in the current isolation method. Elliott et al., Nkx2-5egfp/w hESCs for isolation of human cardiac progenitors and cardiomyocytes, Nature Methods, 2011, 8:1037-1040; Dubois et al., SIRPA is a specific cell-surface marker for isolating cardiomyocytes derived from human pluripotent stem cells, Nature Biotechnology, 2011, 29:1011-1018; Kamp et al., Recognizing heart cells in a crowd, Nature Methods, 2011, 8:1013-1016; and Mummery et al., Sorting cardiomyocytes: A simple solution after all? Nature Methods, 2010, 7:40-42. Since molecular beacons can bind intracellular mRNA through delivery techniques there is no need to find a surface protein specifically expressed on the target cell. Heyduk et al., Molecular beacons for detecting DNA binding proteins, Nature Biotechnology, 2002, 20:171-176; Rhee et al., Target accessibility and signal specificity in live-cell detection of BMP-4 mRNA using molecular beacons, Nucleic Acids Research 2008; 36:e30; Van Hoof et al., Identification of cell surface proteins for antibody-based selection of human embryonic stem cell-derived cardiomyocytes, Journal of Proteome Research, 2010, 9:1610-1618, and Kelly et al., Cell-surface markers for the isolation of pancreatic cell types derived from human embryonic stem cells, Nature Biotechnology, 2011, 29:750-756. Thus, this approach can be more broadly applied to other cell types regardless of the availability of specific surface proteins or antibodies. This is a desirable method for cell purification, as one of the main hurdles to using hPSCs in regenerative medicine is the lack of proper purification methods. Kelly et al., Cell-surface markers for the isolation of pancreatic cell types derived from human embryonic stem cells, Nature Biotechnology, 2011, 29:750-756.

In some embodiments, this technique may be more widely applied to neuronal cells or islet cells that are indispensable for cell-based therapy but lack known surface markers, and will allow homogenous cell populations to be used for drug discovery and disease modeling which have long awaited purified human primary cells. Another benefit of the molecular beacon-based isolation is its applicability to cells from other species as shown for mESCs, facilitating research with purified cells derived from mouse or rat PSCs. In terms of the side effects profile, as molecular beacons usually degrade within an hour, cell viability or cell fate change is not a serious concern.

Methods

The disclosure provides methods for purifying pluripotent stem cell-derived cardiomyocytes using molecular beacons that are designed to target cardiomyocyte specific-mRNA. In certain aspects, this disclosure provides a method of generating purified composition of cardiomyocytes that can be used as a clinical therapy for patients with cardiac damage or as a research tool. Accordingly this disclosure describes a method of a) introducing a molecular beacon that targets cardiomyocyte specific mRNA to a mixture of differentiating pluripotent cells under conditions the molecular hybridizes to the cardiomyocyte specific mRNA providing probe bound fluorescent cardiomyocytes, b) purifying the probe bound fluorescent cardiomyocytes by fluorescence activated cells sorting (FACS) thus providing a purified population of cardiomyocytes, c) generating a cell line expressing said mRNA of interest by growing purified composition of cardiomyocytes.

In certain embodiments, the disclosure provides a method for the differentiation of pluripotent stem cells into a cardiomyocyte population that comprises a) expanding undifferentiated pluripotent stem cells by culturing cells in a monolayer in MTESR® media, b) inducing mesodermal differentiation through application of bone morphogenetic protein 4 (BMP4), Activin A, and fibroblast growth factor 2 (FGF2) to hPSCs, c) inducing of cardiac lineage differentiation by the supplementation with conditioned media, and d) continuous treatment with β-adrenergic receptor agonist isoproterenol to generate spontaneous beating cardiomyocytes. In other embodiments, this disclosure provides a method of differentiating pluripotent stem cells into cardiomyocytes that can be used for differentiation of mammalian induced pluripotent stem cells or embryonic stem cells into cardiomyocytes.

In certain aspects, this disclosure provides a method for selecting cardiomyocyte specific mRNA as potential targets of the molecular beacon wherein, known structural cardiac genes were selected comprising, myosin heavy chain 1 (MHC1), myosin heavy chain 2 (MHC2), troponin T 1 (TNT1), troponin T 2 (TNT2), troponin T 3 (TNT3) wherein, reverse transcriptase (qRT-PCR) analysis was performed on extracted mRNA to determine if target mRNA would be detectable by molecular beacons. Detection of each cardiomyocyte specific mRNA was depicted in FIG. 5. In other embodiments, this disclosure provides a method that selects the MHC-1 gene as the optimal cardiomyocyte specific mRNA target.

In certain embodiments this disclosure provides a method of synthesizing the molecular beacons that target the cardiomyocyte specific mRNA comprising designing an oligonucleotide sequence of that is complementary to the specific target mRNA, wherein the complementary target sequence is flanked by an additional sequence on each side of the oligonucleotide that base pair with each other. In other embodiments, this disclosure provides a method for designing the molecular beacon wherein the oligonucleotide is configured with a fluorophore on one end, and a fluorescent quencher on the opposite end of the oligonucleotide. This disclosure provides a method for designing the molecular beacon wherein, the oligonucleotide is configured with a Cy3 fluorophore on the 5' end and a BLACK HOLE QUENCHER® 2 (BHQ) on the 3'.

In certain embodiments, this disclosure provides a method of introducing the molecular beacons into the mixed population of cardiomyocytes and differentiating pluripotent stem cells that comprises Streptolysin O, LIPOFECTAMINE®2000, LULLABY®, NUCLEOFECTION®, electroporation, and microinjection. In other aspects, this disclosure provides methods for the delivery of the molecular beacons into the differentiating cells by NUCLEOFECTION®.

Certain aspects of this disclosure provides a method wherein, upon the introduction of the molecular beacons to a mixture of cardiomyocytes and pluripotent stem cells, the beacon hybridizes to the complementary mRNA target sequence within cardiomyocytes, wherein upon excitation these hybridized molecular beacons emit a fluorescent signal. In other aspects, this disclosure provides a method where in the absence of a complementary cardiomyocyte mRNA the molecular beacon forms a stem loop, quenching the fluorescent signal of the fluorophore.

In other embodiments, this disclosure provides a method for isolating cardiomyocytes from a mixed population of differentiating cells where molecular beacons that have hybridized to target mRNA sequences emit a fluorescent signal, allowing for the isolation and purification of these cardiomyocytes using fluorescence activated cell sorting, hence a purified composition of cardiomyocytes.

In certain embodiments, this disclosure provides a method for verifying the purity of the isolated cardiomyocyte population wherein more than 50% of the cells stain positive for cardiomyocyte markers ACTN2, TNNT2, and TNNI3 by immunohistochemistry and also exhibit cardiomyocyte morphology. In other embodiments, this disclosure provides a method for confirming the homogeneity of the purified cardiomyocyte population by examining the expression level of specific genes, wherein more than 50% of the cells exhibit an increased expression of cardiomyocyte specific genes, TNNT2, MYH6, MYH7, MYL2, and a marked decrease in the expression of genes specific for smooth muscle cells (CALPONIN), fibroblast (THY1), skeletal myocyte (MYOD), neural lineages (NEUROD), and EC (PECAM1). In yet other aspects, this disclosure provides a method for validating the purity of the isolated cardiomyocyte composition wherein more than 50% of the cells exhibit spontaneous beating and rhythmic calcium oscillation. The embodiments of this disclosure provides a method that purified pluripotent stem cell derived cardiomyocytes exhibit a purity of cardiomyocytes greater than 70%, 80%, 90%, 95% or 98% homogeneity.

In other aspects, this disclosure provides a method of generating a purified composition of cardiomyocytes that can be used in the identification of a cardioactive agent comprising a) introducing a molecular beacon that targets cardiomyocyte specific mRNA to a mixture of differentiating pluripotent cells under conditions the molecular hybridizes to the cardiomyocyte specific mRNA providing probe bound fluorescent cardiomyocytes, b) purifying the probe bound fluorescent cardiomyocytes by fluorescence activated cells sorting (FACS) thus providing a purified population of cardiomyocytes, c) generating a cell line expressing said mRNA of interest by growing purified composition of cardiomyocytes d) contacting the purified cardiomyocyte population with a test agent; and e) determining if the test agent modulates an activity or function of purified cardiomyocytes within the population thus identifying the test agent as a cardioactive agent.

In other embodiments this disclosure provides a method for generating a purified cardiomyocte population for research purposes to be used as a model system for studying cardiac cells. This disclosure provides a method of isolating cardiac cells for experimental protocols that require the increased number or function of cardiomyocytes comprising a) introducing a molecular beacon that targets cardiomyocyte specific mRNA to a mixture of differentiating pluripotent cells under conditions the molecular hybridizes to the cardiomyocyte specific mRNA providing probe bound fluorescent cardiomyocytes, b) purifying the probe bound fluorescent cardiomyocytes by fluorescence activated cells sorting (FACS) thus providing a purified population of cardiomyocytes, c) generating a cell line expressing said mRNA of interest by growing purified composition of cardiomyocytes.

In other embodiments this disclosure provides a method for generating a purified cardiomyocte population for patients that suffer damage or death of cardiac cells. This disclosure provides a method of isolating cardiac cells to assist in the treatment of patients in need of increased numbers or function of cardiomyocytes comprising a) introducing a molecular beacon that targets cardiomyocyte specific mRNA to a mixture of differentiating pluripotent cells under conditions the molecular hybridizes to the cardiomyocyte specific mRNA providing probe bound fluorescent cardiomyocytes, b) purifying the probe bound fluorescent cardiomyocytes by fluorescence activated cells sorting (FACS) thus providing a purified population of cardiomyocytes, c) generating a cell line expressing said mRNA of interest by growing purified composition of cardiomyocytes d) administering, transplanting or grafting the purified composition of cardiomyocytes generated by said purification method into patients.

Molecular Beacons

Generally, the MB includes a nucleic acid that binds to a cardiomyocyte-specific mRNA, and includes at least one fluorophore and at least one quencher. In some embodiments, the nucleic acid binds to at least a portion of a cardiomyocyte specific mRNA. In some embodiments, the cardiomyocyte-specific mRNA is selected from the group consisting of: myosin heavy chain 1 (MHC1), myosin heavy chain 2 (MHC2), troponin T 1 (TNT1), troponin T 2 (TNT2), troponin T 3 (TNT3) wherein, reverse transcriptase (qRT-PCR) confirms that genes will be detectable by the molecular beacon. In other embodiments, the nucleic acid binds to at least a portion of an mRNA selected from the group comprising of genes encoding myosin heavy chain 1 (MHC1), myosin heavy chain 2 (MHC2), troponin T 1 (TNT1), troponin T 2 (TNT2), troponin T 3 (TNT3), ACTN2, and TNNI3. In still further embodiments, the nucleic acid binds to at least a portion of an mRNA selected from MYH6, MYH7, and MYL2. In specific embodiments, the nucleic acid binds to at least MHC1. In some embodiments, the nucleic acid includes at least 5, or at least 10, or at least 15, or at least 20, or at least 25, or at least 30, or at least 35 or at least 40 base pairs that bind to a cardiomyocyte-specific mRNA.

In certain embodiments the complementary cardiomyocyte-specific mRNA sequence is flanked by a stem loop sequence that base pairs in the absence of a target sequence. This flanking stem loop nucleic acid sequence can be at 4, or at least 5, or at least 6 base pairs long.

In some embodiments, the molecular beacon includes at least one fluorophore. In other embodiments, the MB includes at least two fluorophores. In such embodiments, the two or more fluorophores can be in close proximity, and in some embodiments excitation of one fluorophore can lead to excitation of a second or further fluorophores. Examples of fluorophores include but are not limited to Cy2, Cy3, Cy3B, Cy3.5, Cy5, Cy5.5, Cy7, FAM, 6-FAM, Fluorescein, JOE, TET, HEX, TRITC, TEXAS RED®, X-Rhodamine, Lissamine Rhodamine B, Allophycocyanin (APC), BODIPY-FL, FluorX, TruRed, PerCP, Red 613, R-Phycoerythrin (PE), NBD, Lucifer Yellow, Pacific Orange, Pacific Blue, Cascade Blue, Methoxycoumarin, Aminocoumarin, and Hydroxycoumarin. In some embodiments the fluorophore is attached to the MB adjacent to the stem loop sequence.

In some embodiments, the molecular beacon includes at least one quencher. In some embodiments, the quencher is a non-fluorescent quencher including but not limited to a BLACK HOLE QUENCHER® (BHQ), Eclipse Dark Quencher (DQ), IOWA Black (IWB), DABCYL, and TAMRA. In certain embodiments, the quencher is at least 14 nucleic acids away from the fluorophores. In some embodiments the quencher is attached to the MB adjacent to the stem loop sequence.

Cardiomyocyte Specific mRNAs

In some embodiments, this disclosure provides cardiomyocyte specific mRNA that can be targeted by molecular beacons, and used in the purification of stem cell derived cardiomyocytes. In certain embodiments cardiomyocyte specific mRNA targets can be selected and confirmed by using reverse transcriptase (qRT-PCR) to ensure that genes will be detectable by the molecular beacon. In certain embodiments, a MB hybridizes to a portion of the cardiomyocyte specific mRNA, and upon excitation fluoresces, marking cardiomyocytes with this specific mRNA for selection and further purification. The cardiomyocyte specific mRNA are genes that are highly expressed in cardiomyocytes in comparison to expression levels of these genes in other cell types. In some embodiments, the cardiomyocyte-specific mRNA is selected from a group comprising myosin heavy chain 1 (MHC1), myosin heavy chain 2 (MHC2), troponin T 1 (TNT1), troponin T 2 (TNT2), troponin T 3 (TNT3) ACTN2, TNNT2, and TNNI3, MYH6, MYH7, Myosin light chain 2 (MYL 2), Myosin light chain 2a (MYL 2a), Myosin light chain polypeptide 4 (MYL 4), α-Tropomyosin I, α-Actin (ACTC), Colligin, HSP17, HSP90, Lactate dehydrogenase, α-Enolase 1 (ENO1), Voltage-dependent anion channel 1 (VDAC-1), RAB-7, Protein phosphatase 1, regulatory (inhibitor) subunit (PPP1 R), RSU-1, Makorin I, CGI 146 protein, Crystallin aB, Exostose 2 (EXT2), Elongation factor eiF 4A, Protein phosphatase 1, catalytic subunit—beta isoform (PPP1 CB), and Glutamic oxaloacetic transaminase (GOT1).

Methods of Use

In certain aspects, this disclosure provides a method for generating a purified composition of cardiomyocytes for patients that suffer damage or death of cardiac tissue. This discolor provides a method of isolating cardiac cells to assist in the treatment of patients suffering from heart disease including but not limited to heart failure, heart attack, coronary artery disease, cardiomyopathy, restrictive cardiomyopathy, or hypertrophic cardiomyopathy, wherein the patient is in need of an increased number or function of cardiomyocytes comprising a) introducing a molecular beacon that targets cardiomyocyte specific mRNA to a mixture of differentiating pluripotent cells under conditions the molecular hybridizes to the cardiomyocyte specific mRNA providing probe bound fluorescent cardiomyocytes, b) purifying the probe bound fluorescent cardiomyocytes by fluorescence activated cells sorting (FACS) thus providing a purified population of cardiomyocytes, c) generating a cell line expressing said mRNA of interest by growing purified composition of cardiomyocytes d) administering, transplanting or grafting the purified composition of cardiomyocytes generated by said purification method into patients.

In certain embodiments this disclosure provides a method for producing a purified composition of cardiac cells for research purposes to be used as a model system for studying cardiomyocytes. This disclosure provides a method of isolating cardiac cells for experimental protocols that require the increased number or function of cardiomyocytes comprising a) introducing a molecular beacon that targets cardiomyocyte specific mRNA to a mixture of differentiating pluripotent cells under conditions the molecular hybridizes to the cardiomyocyte specific mRNA providing probe bound fluorescent cardiomyocytes, b) purifying the probe bound fluorescent cardiomyocytes by fluorescence activated cells sorting (FACS) thus providing a purified population of cardiomyocytes, c) generating a cell line expressing said mRNA of interest by growing purified composition of cardiomyocytes.

In other embodiments, this disclosure provides a method that can be used for research purposes to examine the function and activity of the purified cardiomyocyte composition within a host. In certain embodiments this method comprises a) introducing a molecular beacon that targets cardiomyocyte specific mRNA to a mixture of differentiating pluripotent cells under conditions the molecular hybridizes to the cardiomyocyte specific mRNA providing probe bound fluorescent cardiomyocytes, b) purifying the probe bound fluorescent cardiomyocytes by fluorescence activated cells sorting (FACS) thus providing a purified population of cardiomyocytes, c) generating a cell line expressing said mRNA of interest by growing purified composition of cardiomyocytes d) transplanting or grafting the purified cardiomyocyte population into the desired mammalian host and examining cardiomyocyte function within the host.

Kits

The disclosure provides kits for carrying out any of the methods described herein. Kits of the disclosure may comprise at least one molecular beacon specific for cardiomyocyte specific mRNA, and may further include instructions for carrying out a method described herein. Kits may also comprise oligonucleotides for the corresponding cardiomyocyte specific target gene for qRT-PCR analysis to ensure that said gene will be detectable by molecular beacons provided therein.

In certain embodiment, the disclosure provides kits for purifying pluripotent stem cell derived cardiomyocytes from a mixed population of differentiating pluripotent cells including at least one molecular beacon that targets a cardiomyocyte specific mRNA, where the molecular beacon is from a group consisting of myosin heavy chain 1 (MHC1), myosin heavy chain 2 (MHC2), troponin T 1 (TNT1), troponin T 2 (TNT2), troponin T 3 (TNT3) or any cardiomyocyte specific mRNA sequence and instructions for carrying out a method for the purification of pluripotent stem cell derived cardiomyocytes described herein.

In some other aspect, the disclosure provides kits for purifying pluripotent stem cell derived cardiomyocytes from a mixed population of differentiating pluripotent cells including at least one reagent specific for MHC-1; and instructions for carrying out a method for the purification of stem cell derived cardiomyocytes described herein.

In a further aspect, the disclosure provides kits for purifying pluripotent stem cell derived cardiomyocytes from a mixed population of differentiating pluripotent cells including at least one reagent specific for MHC-1, at least one reagent specific for MHC-2, at least one reagent specific for TNT1, at least one reagent specific for TNT2, one reagent specific for TNT3 and instructions for carrying out a method for the purification of pluripotent stem cell derived cardiomyocytes described herein.

In further examples of kits, the reagent specific for the cardiomyocyte specific mRNA can be oligonucleotides that are specific for the said mRNA target. In further examples of kits, the reagent specific for the cardiomyocyte specific mRNA can be a molecular beacon. In further examples of kits the reagent specific for the cardiomyocyte specific mRNA can be a fluorescent probes.

More commonly, kits of the disclosure comprise at least one molecular beacon that targets a cardiomyocyte specific mRNA, where the reagent is particular to the cardiomyocyte specific mRNA. In some embodiments, kits comprise at least 2, at least 3, at least 4, or at least 5, reagents specific for a molecular beacon or a cardiomyocyte specific mRNA target. In some embodiments, the reagent is specific for a cardiomyocyte mRNA target. In certain embodiments, the reagents are specific for myosin heavy chain 1 (MHC1), myosin heavy chain 2 (MHC2), troponin T 1 (TNT1), troponin T 2 (TNT2), troponin T 3 (TNT3).

Kits comprising a single reagent specific for a molecular beacon or cardiomyocyte specific mRNA target will generally have the reagent enclosed in a container (e.g., a vial, ampoule, or other suitable storage container). Likewise, kits including more than one reagent may also have the reagents in containers (separately or in a mixture).

In some embodiments, the cardiomyocyte mRNA-specific reagent(s) will be labeled with a detectable marker (such as a fluorescent dye), or be modified to facilitate detection. In other embodiments, the cardiomyocyte mRNA or molecular beacon-specific reagent will not be directly labeled or modified.

The instructions relating to the use of the kit for carrying out the disclosure generally describe how the contents of the kit are used to carry out the methods of the disclosure. Instructions may include information as sample requirements (e.g., form, pre-assay processing, and size), steps to design molecular beacons, steps to introduce molecular beacons, steps to isolate cardiomyocytes with bound molecular beacons, steps n for assaying efficiency of purification, steps for validating purity, and interpretation of results.

Instructions supplied in the kits of the disclosure are typically written instructions on a label or package insert (e.g., a paper sheet included in the kit), but machine-readable instructions (e.g., instructions carried on a magnetic or optical storage disk) are also acceptable. In certain embodiments, machine-readable instructions comprise software for a programmable digital computer for comparing the measured values obtained using the reagents included in the kit.

Systems for Detecting and Sorting Cardiomyocytes with Molecular Beacon Bound mRNA In certain embodiments, the methods may be implemented by computers, systems, or stored on a computer-readable storage medium as instructions for detecting cardiomyocytes with molecular beacon bound mRNA.

In some embodiments, the disclosure relates to a system. The system may include a computer having a processor configured to perform the methods of the disclosure. The system may also include or may communicate with a laser, electronic detection apparatus, fluorescent camera, or other device that can measure light or a change in current of an electrode or system configured to subject a sample to testing device.

In some embodiments, the system may include a computer having a processor configured to perform the methods of the disclosure. In certain embodiments, the method contemplates recording measurements on a computer readable medium as data. In certain embodiments the disclosure, contemplates reporting purification results to a medical professional, researcher or a representative thereof. In certain embodiments, the disclosure contemplates transferring recorded data over the internet from a lab to a computer in a medical or research facility.

In some embodiments, the method further comprises outputting quantification results. In some embodiments, the method may further comprise recording the detected changes on a computer-readable medium through a visual device such as a camera or video recorder. In certain embodiments, the disclosure contemplates calculating fluorescent intensity.

In some embodiments, the yield and purity of cardiomyocytes may be outputted from a visual device through fluorescence. In some embodiments, the outputting may include displaying, printing, storing, and/or transmitting the measured fluorescence levels. In some embodiments, the measured fluorescence may be transmitted to another system, server and/or storage device for the printing, displaying and/or storing.

The methods of the disclosure are not limited to the steps described herein. The steps may be individually modified or omitted, as well as additional steps may be added.

Unless stated otherwise as apparent from the following discussion, it will be appreciated that terms such as "detecting," "receiving," "quantifying," "generating," "registering," "determining," "obtaining," "processing," "computing," "deriving," "estimating," "calculating" "inferring" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

It is to be further understood that, because some components and method steps may be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

The following Examples are provided to illustrate the disclosure, but are not intended to limit the scope of the disclosure in any way.

Examples

Purification of Cardiomyocytes from Differentiating Pluripotent Stem Cells Using Molecular Beacons that Target Cardiomyocyte-Specific mRNA Although methods for generating cardiomyocytes from pluripotent stem cells have been reported, current methods produce heterogeneous mixtures of cardiomyocytes and noncardiomyocyte cells. Here, pluripotent stem cell-derived cardiomyocytes are purified by cardiomyocyte-specific molecular beacons (MBs). MBs are nucleic acid probes that emit a fluorescence signal when hybridized to target mRNAs. MBs targeting mRNAs of either cardiac troponin T or myosin heavy chain 6/7 were generated. Among MBs, an MB that targeted myosin heavy chain 6/7 mRNA (MHC1-MB) identified up to 99% of HL-1 cardiomyocytes, a mouse cardiomyocyte cell line, but <3% of 4 noncardiomyocyte cell types in flow cytometry analysis, which indicates that MHC1-MB is specific for identifying cardiomyocytes. MHC1-MB was delivered into cardiomyogenically differentiated pluripotent stem cells through NUCLEOFECTION®. The detection rate of cardiomyocytes was similar to the percentages of cardiac troponin T- or cardiac troponin I-positive cardiomyocytes, which supports the specificity of MBs. MHC1-MB-positive cells were sorted by fluorescence-activated cell sorter from mouse and human pluripotent stem cell differentiating cultures, and about 97% cells expressed cardiac troponin T or cardiac troponin I as determined by flow cytometry. These MB-based sorted cells maintained their cardiomyocyte characteristics, which was verified by spontaneous beating, electrophysiological studies, and expression of cardiac proteins. When transplanted in a myocardial infarction model, MB-based purified cardiomyocytes improved cardiac function and demonstrated significant engraftment for 4 weeks without forming tumors.

A strategy was developed to purify cardiomyocytes from differentiating PSCs by targeting genes that are specifically expressed in cardiomyocytes. Molecular beacons (MBs) hybridized to cardiomyocyte-specific mRNAs enable isolation of cardiomyocytes from a mixed population. This method can be applied for both basic research and clinical applications. FIG. 1A shows MBs that are dual-labeled antisense oligonucleotide nanoscale probes with a fluorophore at one end and a quencher at the other end. MBs are designed to form a stem-loop (hairpin) structure in the absence of a complementary target so that fluorescence of the fluorophore is quenched; however, hybridization with the target mRNA opens the hairpin and separates the reporter from the quencher, which allows emission of a fluorescence signal (FIG. 1B). MB technology has been tested in a variety of cell types to detect mRNA at various levels of expression and has been demonstrated to not alter the expression level of target genes. MBs may be used for detecting mouse embryonic stem cells (mESCs) by simultaneous targeting of intracellular Oct4 (octamer-binding transcription factor 4) mRNA and surface markers.

Protocols have been developed to differentiate mouse and human PSCs into cardiomyocytes and devised a strategy to isolate cardiomyocytes by applying MBs that target cardiomyocyte-specific mRNAs, followed by FACS (FIG. 2). One can purifying cardiomyocytes at high efficiency and specificity from hPSC differentiation cultures with this clinically compatible purification system. These purified cardiomyocytes are functional in vitro and in vivo.

Five MBs were synthesized by MWG Operon using standard resin-based synthesis methods with HPLC purification (Table 1).

TABLE 1

List of Molecular Beacons and Parameters

| Beacon Name | Target Sequence | Beacon Sequence |
|---|---|---|
| TNT1 | CCCAAGATCCCCGATGGAGAGAG (SEQ ID NO. 9) | TACCCTCTCTCCATCGG GGATCTTGGGTA (SEQ ID NO. 14) |
| TNT2 | AGAACCGCCTGGCTGAAGAGA (SEQ ID NO. 10) | CCCTCTCTTCAGCCAGG CGGTTCTGAGGG (SEQ ID NO. 15) |
| TNT3 | GAACAGGAGGAAGGCTGAGG (SEQ ID NO. 11) | ATCCTCAGCCTTCCTC CTGTTCGAGGAT (SEQ ID NO. 16) |
| MHC1 | GTGAAGAAGAAGATGGAGG (SEQ ID NO. 12) | CCTCCATCTTCTTCTT CACGGAGG (SEQ ID NO. 3) |
| MHC2 | AAGAGCCGGGACATTGGTGCCAA (SEQ ID NO. 13) | TTGGCACCAATGTCC CGGCTCTTGCCAA (SEQ ID NO. 17) |

In silico description of the molecular beacons synthesized for study. The duplex melting temperature describes a measure of the predicted affinity between the sequence-specific beacon loop and the target sequence. MHC1 indicates myosin heavy chain 1; MHC2, myosin heavy chain 2; TNT1, troponin T 1; TNT2, troponin T 2; and TNT3, troponin T 3. In Beacon Sequence, italic letters indicate stem sequences.

An efficient method for purifying cardiomyocytes from differentiating mouse and human PSCs by directly targeting the mRNA of cardiomyocyte-specific genes is provided herein. Using a MB that targeted the mRNA of MYH6 and MYH7 followed by FACS, one is able to enrich a population made up of >97% cardiomyocytes from differentiating PSCs. Their identity as cardiomyocytes was verified by a series of experiments that included flow cytometry, immunocytochemistry, and qRT-PCR. Importantly, these purified cardiomyocytes displayed spontaneous beating on further culture and demonstrated stable action potentials and Ca2+ oscillation in electrophysiological studies. When injected into infarcted heart, MB-purified cardiomyocytes were integrated and survived robustly for 4 weeks in post-MI hearts, showing improved cardiac function without forming tumors. On the other hand, mice injected with unpurified cardiomyocytes developed teratomas. These results support the idea that MB-based isolated cardiomyocytes are pure and functionally intact cardiomyocytes and that cardiomyocyte purification is important for cell therapy.

Despite continuous improvements in current cardiomyocyte differentiation protocols, the resulting differentiated cell populations still contain a percentage of noncardiomyocytes. Hence, one of the major challenges is to develop stable isolation techniques that allow scalable purification of cardiomyocytes. Recently, studies using FACS-based cardiomyocyte purification have attracted attention. In the first, a mitochondrial dye, TMRM, was suggested to be useful for cardiomyocyte selection, enriching up 99% of cardiomyocytes as determined by the expression of Acnt2 (α-sarcomeric actinin) in immunocytochemistry. This approach was based on findings that cardiomyocytes have high mitochondrial content and can be purified via fluorescent dyes that label mitochondria. However, other subsequent studies demonstrated that TMRM not only failed to identify immature cardiomyocytes early in differentiation culture but also detected noncardiogenic cells or undifferentiated hESCs, because these cells take up significant amounts of TMRM. In addition, independent studies reported the identification of surface marker proteins, SIRPA and VCAM-1, and suggested their utility for isolating cardiomyocytes from differentiating hPSCs. To identify a candidate protein, a panel of 370 known commercially available antibodies were screened. SIRPA was identified as a specific marker for cardiomyocytes differentiating from hPSCs. Subsequently, isolation via FACS with an antibody against SIRPA enriched cardiac precursors and cardiomyocytes from hPSCs, yielding up to 98% TNNT2+ cells. However, SIRPA+ cells expressed significant amounts of smooth muscle marker genes such as ACTA2 and CNN1 and an endothelial cell gene, CD34, which brings into question the utility of SIRPA as a sole marker for cardiomyocyte isolation. There are variations in the yield of cardiogenic marker expression (NKX2-5) after further culture of sorted SIRPA+ cells, reaching as low as 2.8% cardiomyocytes depending on the isolation time and duration of culture. Furthermore, NKX2-5+ cells did not express SIRPA, which raised concerns about specificity and sensitivity of SIRPA. Thus, VCAM1, through a transcriptome analysis and used it as an additional marker to isolate cardiomyocytes. However, FACS with both SIRPA and VCAM1 antibodies was only able to enrich cardiomyocytes that ranged from 55% to 95% in purity. Moreover, because both proteins are known to be expressed in other cell types, the possibility of contamination with noncardiomyocyte cells even after purification with SIRPA and VCAM1 may be an issue.

The MB-based cardiomyocyte purification strategy has a number of unique advantages. First, by directly targeting specific intracellular mRNA, there is no need to make extensive efforts to identify surface proteins for cell isolation with the corresponding antibodies. Second, MB-based cell purification minimizes contamination of other cells by using MBs designed to hybridize with unique sequences in the mRNAs of interest specifically expressed in the target cell type. Although significant efforts have been made to identify SIRPA and VCAM1 as cell-surface markers for cardiomyocytes, both SIRPA and VCAM1 are expressed in other organs such as brain and lung, which raises questions about the utility of these surface markers in a range of differentiation systems. Another advantage of the MB-based purification method is its application to any species. It allows expansion of the research scope with any desired cells. Because SIRPA is not highly expressed in the mouse, its usage is limited to human cells. In contrast, the MB-based method allows isolation of virtually any cell because of the unlimited accessibility of MBs to intracellular mRNA. Therefore, in addition to cardiomyocytes, the MB-based sorting technique described here can be broadly applied to the isolation of other cell types, such as neural-lineage cells or islet cells, which are elements in regenerative medicine but do not have specific surface proteins identified to date.

The present cell transplantation study provides an important insight into the need for purified cardiomyocytes for cardiac cell therapy. An unexpectedly high rate of tumors developed in mice that received unpurified mESC-derived cardiomyocytes. Although unpurified, these cells were differentiated into the cardiac lineage, and about 50% of cells were cardiomyocytes. To date, a few studies have reported syngeneic or allogeneic transplantation of unpurified mESC-derived cardiomyocytes into infarcted heart, and all demonstrated tumor formation in hearts. The present disclosure demonstrated that purified cardiomyocytes do not form tumors, and this purification process is a prerequisite for cardiac cell therapy with PSCs. Similar cardiac cell therapy studies were conducted with hPSC-derived cardiomyocytes, and many of them showed functional improvement with no tumor formation, albeit using nonpurified cells.

To ensure that MBs were safe and effective to use in target cells, several experiments were performed to determine cell viability and functionality immediately and several days after delivery of MBs. MBs were minimally disruptive, because the results did not differ significantly between hPSC cardiomyocytes and control cells in the assays performed. MBs usually degrade within an hour, so cell viability or cell fate change is not a serious concern. In addition, to confirm their specificity, extensive testing was performed to ensure that the MB signal was a robust indicator of cardiomyocytes based on the binding of the probe to MYH6/7. The MBs were tested in solution with synthetic target oligonucleotides that varied from the ideal sequences by 6 bp, the closest that a BLAST search through the human transcriptome predicted. None of the MBs used in the present study increased their fluorescence by >50% even when incubated with excess target sequence.

The purified hPSC-derived cardiomyocytes sorted via MBs will be enormously useful for clinical applications and preclinical studies. A major obstacle to the use of cells differentiated from hPSCs for clinical applications is potential tumorigenicity or aberrant tissue formation after cell transplantation. By eliminating unwanted cells, this technology will advance the use of hPSC-derived cardiomyocytes. This purification technique in combination with cardiomyocytes generated from patient-specific hiPSCs will be of great value for drug screening and disease modeling, as well as cell therapy.

Cardiomyocyte-Specific MB Generation

To determine optimal candidate genes detectable by MBs, quantitative RT-PCR (qRT-PCR) analysis was performed on known cardiac-specific genes using mRNAs extracted from freshly isolated mouse adult cardiomyocytes, human neonatal heart tissues, and human fetal heart tissues. The representative cardiac structural genes cardiac troponin T (TNNT2, also known as cTNT) and myosin heavy chain (MYH6/7, also known as α/βMHC) were most highly expressed in all of these samples and thus were determined to be targets for MBs. On the basis of the qRT-PCR results, 5 MBs were designed (Table 1) that targeted unique sites in TNNT2 or MYH6/7 mRNA in both mouse and human using design rules and BLAST (Basic Local Alignment Search Tool; National Library of Medicine, Bethesda, Md.) searches to ensure uniqueness. These MBs were synthesized with a Cy3 fluorophore or a FAM fluorophore at the 5' end and a BLACK HOLE QUENCHER® 2 or a BLACK HOLE QUENCHER® 1 at the 3' end as specified in Table 1. The beacon fluorescence signal was quantified when hybridized to perfectly complementary and mismatched targets by incubating 500 nmol/L MBs with targets of increasing concentrations (100-500 nmol/L). The MB signal was recorded with a microplate reader and normalized by the signal in wells with an MB only. All MBs displayed a linear response to increasing concentrations of complementary target and a low response to mismatched targets.

To determine the most efficient transfection method to deliver MBs into living cells, the following techniques were compared: Streptolysin O, LIPOFECTAMINE® 2000, LULLABY®, 34 NUCLEOFECTION®, electroporation, and microinjection. To quantify delivery efficiency, a nonspecific MB was fabricated that has a nonspecific sequence with FAM dyes conjugated to both the 5' and 3' ends, which allows the probe to fluoresce regardless of its open or closed conformation. The nonspecific MB were delivered into various cell lines, including an immortalized mouse cardiomyocyte cell line [HL-1 cardiomyocytes24] smooth muscle cells, mouse embryonic fibroblasts, and mESCs. Flow cytometry analysis demonstrated that regardless of the cell type, NUCLEOFECTION® consistently delivered MBs into >95% of the cells, showing the highest delivery efficiency.

The sensitivity of MBs designed to target cardiomyocyte-specific mRNAs was determined. As a positive control, HL-1 cardiomyocytes were used. The cardiomyocyte identity of HL-1 cardiomyocytes were confirmed by flow cytometry showing that 97.2% of cells expressed Tnnt2. Each of the candidate MBs targeting TNNT2 or MYH mRNA was delivered into HL-1 cardiomyocytes by NUCLEOFECTION®, and efficacy was analyzed by flow cytometry. Among the 5 MBs (TNT1, TNT2, TNT3, MHC1, and MHC2) examined, the MB designated as MHC1-MB yielded the highest rate of MB-signal-positive cells (98.9%; FIG. 3A).

Figure 3B:
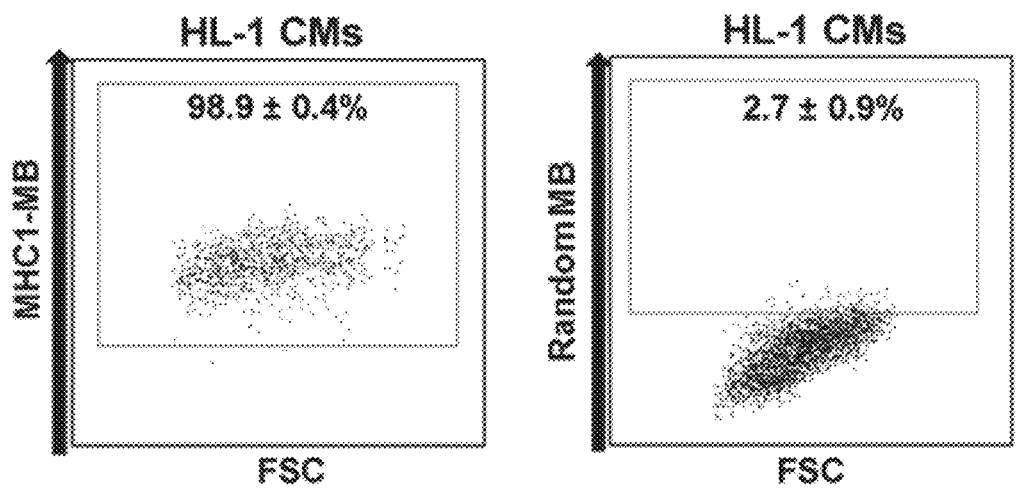
FIG. 3B shows flow cytometry analysis of HL-1 cardiomyocytes treated with random vs MHC1-MBs. Numbers represent percentages of MB-positive cells. n=3. CMs indicates cardiomyocytes; FSC, forward scatter; MHC, myosin heavy chain; and TNT, troponin T.

To determine the specificity of MHC1-MB, a random-sequence MB (random beacon) that has a 16-base target sequence that does not match any sequence in the mouse or human genome was delivered as a negative control and displayed negligible fluorescence in HL-1 cardiomyocytes (FIG. 3B), thus ruling out the possibility that the fluorescence signal from MHC1-MB was caused by nonspecific interactions or probe degradation by endonucleases. To further verify the specificity of the MHC1-MB, MHC1-MB was delivered into smooth muscle cells, mouse aortic endothelial cells, mouse cardiac fibroblasts, and mESCs, which are the cell types most likely to contaminate in cardiomyogenically differentiated PSC cultures. Flow cytometry analysis showed that <3% of these cells displayed a detectable fluorescence signal. These results suggest high sensitivity of the MHC1-MB for cardiomyocyte-lineage cells.

Purification of mESC-Derived Cardiomyocytes

Figure 4A:
FIG. 4A shows data on the purification of cardiomyocytes from differentiating mouse embryonic stem cells (mESCs) with cardiomyocyte-specific molecular beacons (MBs). Schematic of the protocol used for differentiating mESCs to the cardiac lineage. EB indicates embryoid body; and ES, embryonic stem cell.
Figure 4B:
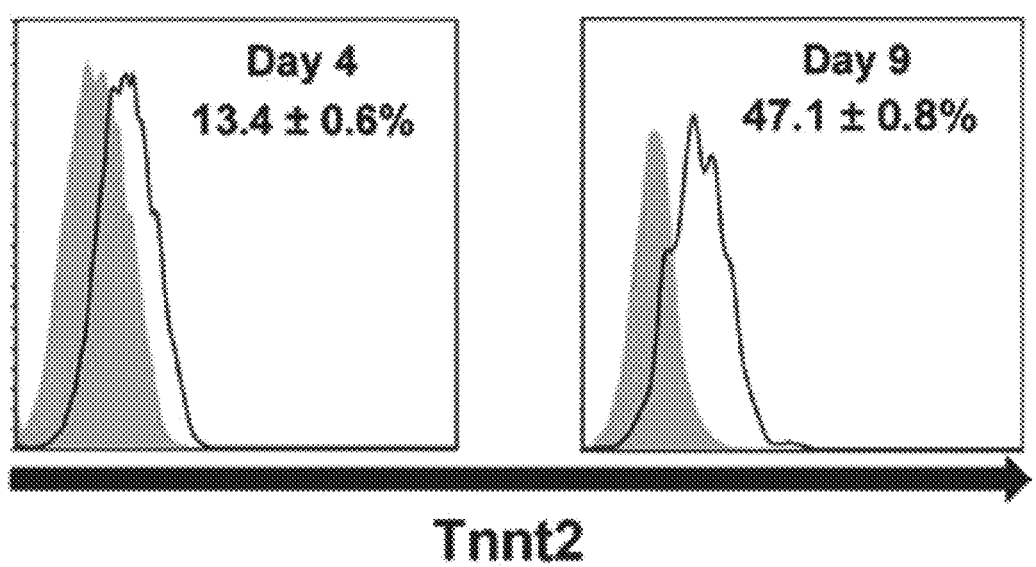
FIG. 4B shows percent expression of Tnnt2 at days 4 and 9 during mESC differentiation into cardiomyocytes; n=3.
Figure 4C:
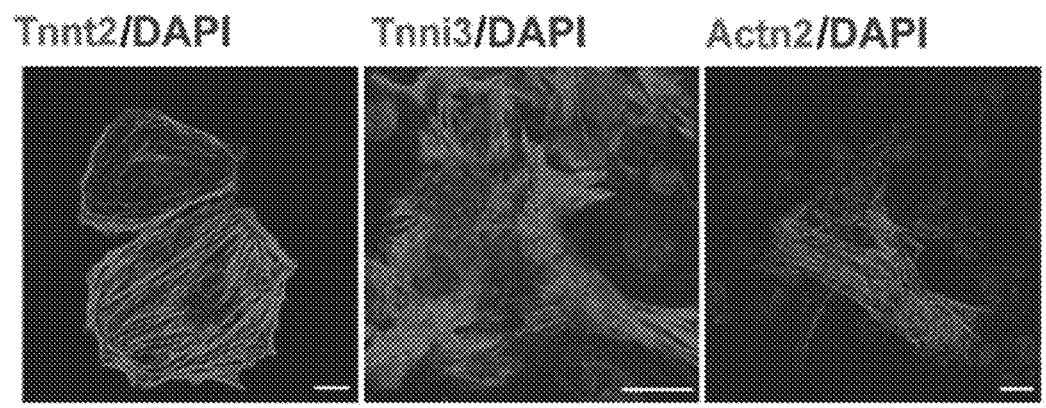
FIG. 4C shows immunocytochemistry results of mESC-derived cardiomyocytes at day 9 for Tnnt2, Tnnt3, and Actn2. Scale bars, 20 μm.
Figure 4D:
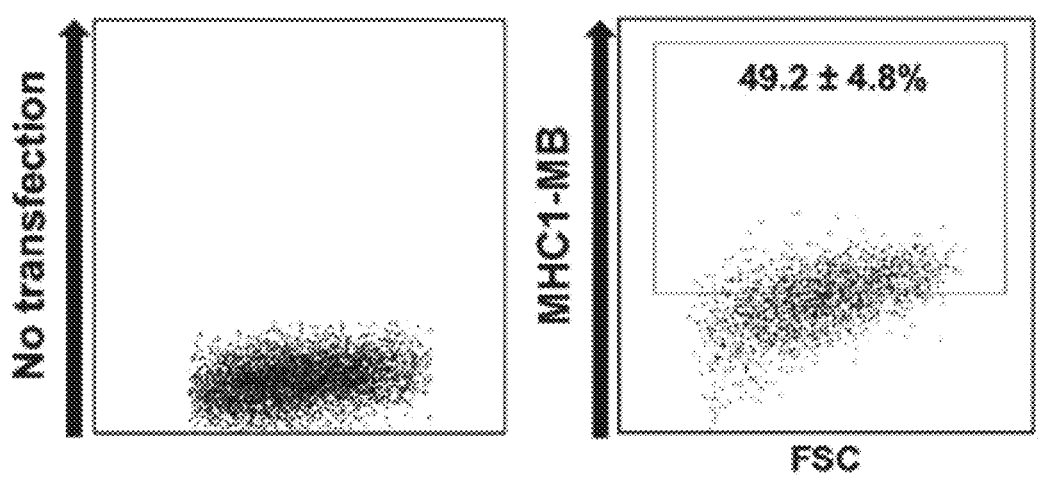
FIG. 4D shows flow cytometry analyses of MHC1-MB (an MB that targeted myosin heavy chain 6/7 mRNA) signals in mESC differentiation culture at day 9; n=6. FSC indicates forward scatter.
Figure 4E:
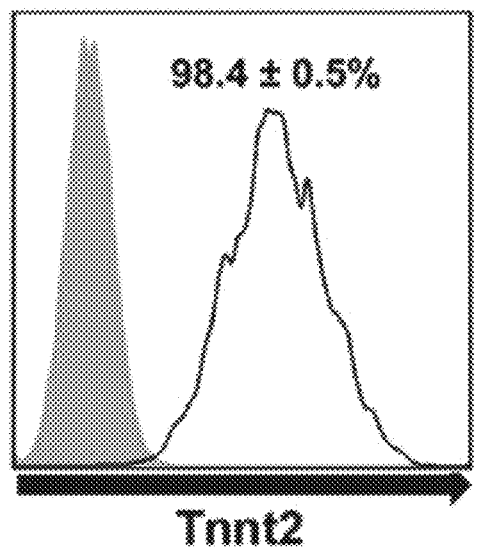
FIG. 4E shows flow cytometry analysis of Tnnt2 expression in mESCs sorted with MHC1-MB and fluorescence activated cell sorting (FACS) at differentiation day 9; n=3. Numbers represent percentages of MB-positive cells (D, E).
Figure 4F:
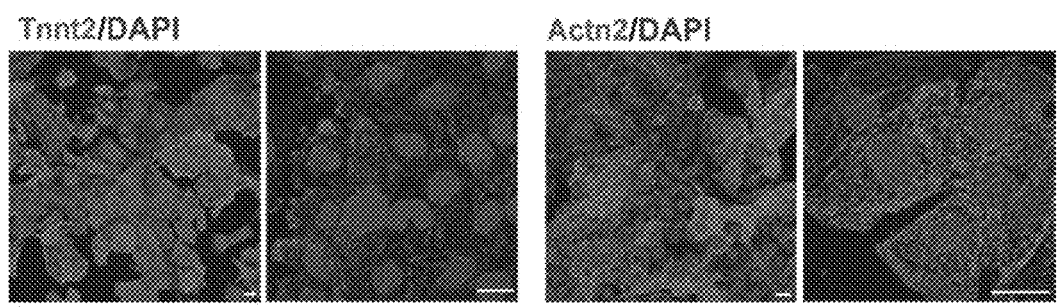
FIG. 4F shows FACS-sorted MHC1-MB-positive cells exhibited Tnnt2 and Actn2 in immunocytochemistry. Scale bars, 20 μm.
Figure 4G:
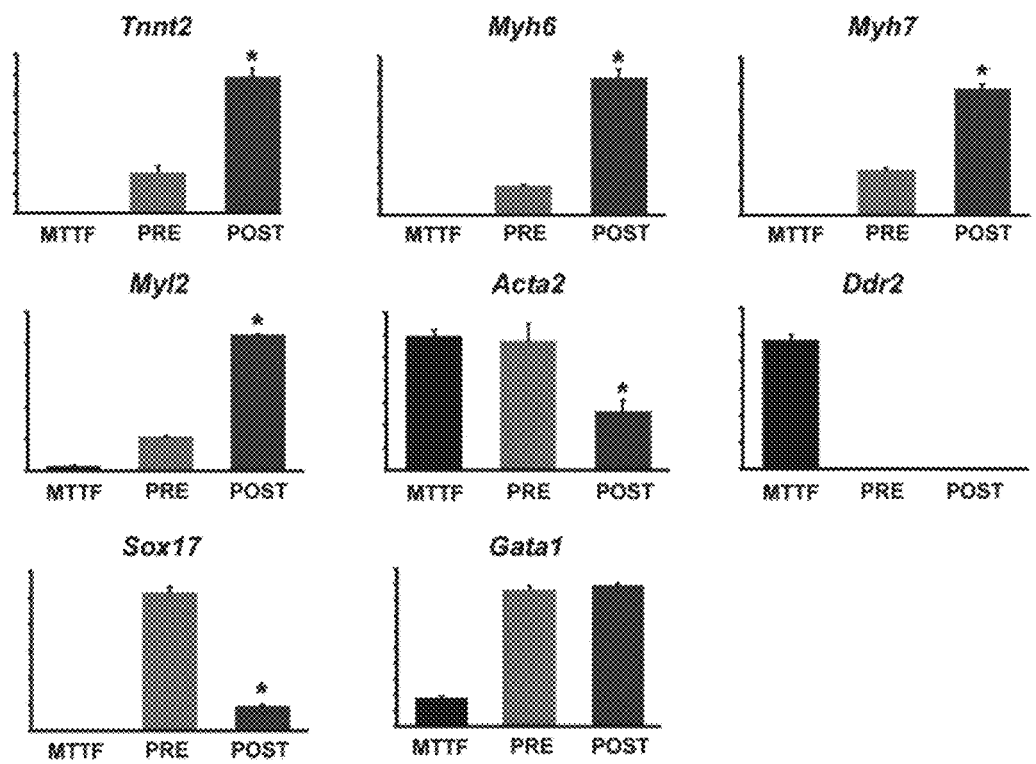
FIG. 4G shows quantitative reverse-transcriptase polymerase chain reaction analyses showing difference in gene expression levels between mouse tail tip fibroblasts (MTTF) and presorted (PRE) and postsorted (POST) mESCs. The cardiomyocyte genes Tnnt2, Myh6, Myh7, and Myl2 were significantly enriched in postsorted cells with MHC1-MB, and noncardiac lineage genes (Acta2, Ddr2, Gata1, and Sox17) were substantially reduced compared with presorted cells. The y axis represents relative mRNA expression of target genes to GAPDH. A.U. indicates arbitrary units. *P<0.05 compared with presorted group; n=3.

Whether this MB could be useful for isolating cardiomyocytes from differentiating mouse PSCs was investigated. An embryoid body-mediated system was established to efficiently differentiate mESCs into cardiomyocytes (FIG. 4A). In brief, undifferentiated mouse ESCs (J1) maintained on STO feeder cells were enzymatically detached to form embryoid bodies, which were cultured for 5 days and plated on a fibronectin-coated dish for cardiomyocyte differentiation. After 3 to 4 days of differentiation in the presence of ascorbic acid (50 µg/mL), spontaneously beating clumps began to appear. Flow cytometry analysis demonstrated that the percentage of Tnnt2-positive cells was 13.4% and 47.1% at days 4 and 9, respectively (FIG. 4B). Immunostaining further demonstrated that cells dissociated from beating clumps displayed Tnnt2, Tnni3, and Actn2 (or α-sarcomeric actinin), which confirmed their cardiomyocyte nature (FIG. 4C). The results with mouse iPSCs were similar. After establishing the differentiation system, attempts were made to isolate cardiomyocytes from differentiating mESCs using MBs. The differentiating mESCs at day 9 were subjected to NUCLEOFECTION® with MHC1-MB and subjected to FACS. The percentage of cells positive for fluorescence signal from MHC1-MB was 49.2±4.8% (FIG. 4D). There was significant agreement between the detection rate of cardiomyocytes with antibody-based (47.1% Tnnt2-positive cells) and MB-based (49.2% MHC1-MB-positive cells) flow cytometry results, which supports the specificity of MHC1-MB. Fluorescent microscopic imaging also confirmed these results. Next, cells were sorted by FACS with MHC1-MB, and 98.4% of the sorted MHC1-MB-positive cells exhibited Tnnt2 in flow cytometry (FIG. 4E). Immunocytochemistry verified that virtually all sorted MHC1-MB-positive cells expressed Tnnt2 and Actn2 (FIG. 4F). qRT-PCR analyses demonstrated that these sorted cells expressed 2- to 6-fold higher levels of Tnnt2, Myh6, Myh7, and Myl2 than the presorted cells (FIG. 4G). Genes representing other lineages were either expressed at negligible levels (Acta2, Ddr2, Gata1, and Sox17) or were undetectable (Pecam1, MyoD, and NeuroD) in the sorted cells (FIG. 4G). Importantly, these sorted cells showed spontaneous contraction over 2 weeks, which suggests that these MB-based purified cardiomyocytes were functional.

Purification of hESC-Derived Cardiomyocytes

Figure 5A:
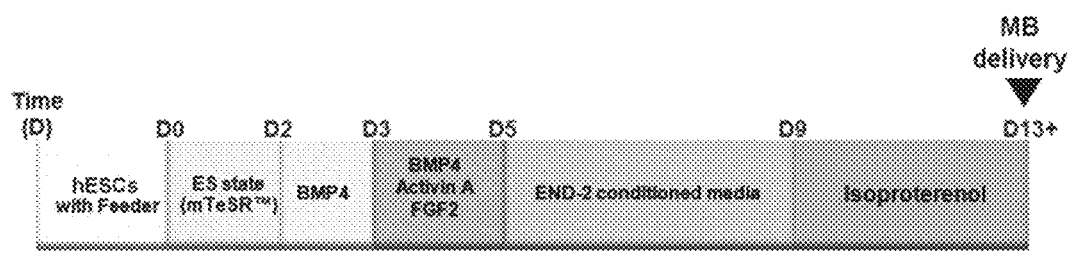
FIG. 5A shows data on purification of cardiomyocytes from differentiating human embryonic stem cells (hESCs) by cell sorting via molecular beacon (MB) and fluorescence-activated cell sorting (FACS). Schematic of the protocol to differentiate human pluripotent stem cells (hPSCs) to the cardiac lineage. BMP4 indicates bone morphogenetic protein 4; END-2, mouse endoderm-like cells; ES, embryonic stem cell; and FGF2, basic fibroblast growth factor.
Figure 5E:
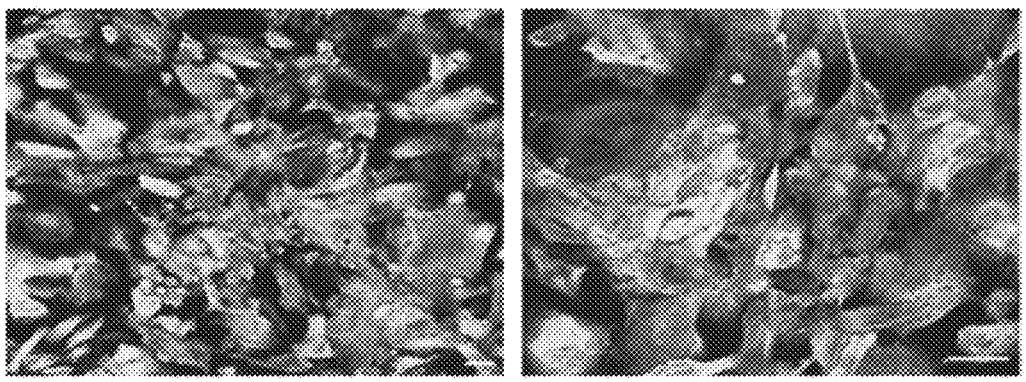
FIG. 5E shows immunocytochemistry for TNNI3 and TNNT2 on MHC1-MB-positive cells sorted from hESC cultures. Scale bars, 20 μm.
Figure 5E:
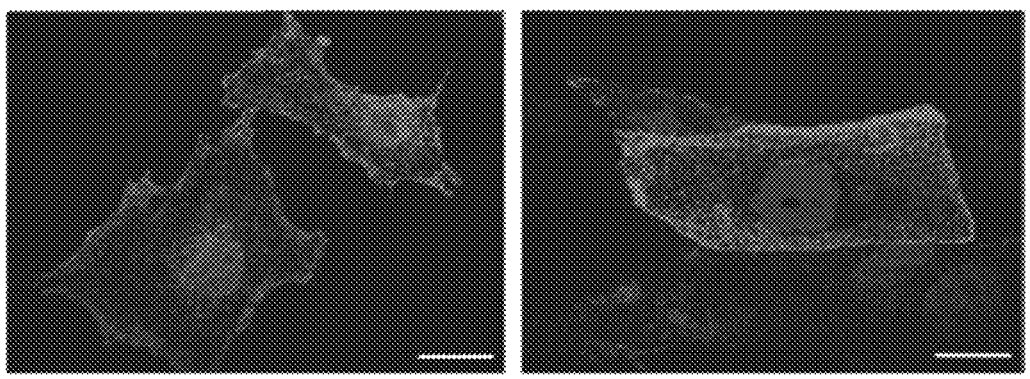

The utility of MB-based cell sorting for hPSC-derived cardiomyocytes was investigated. A 4-step protocol was developed for differentiating hPSCs into cardiomyocytes (FIG. 5A). In phase 1, undifferentiated hESCs (H1) were directly transferred onto Matrigel-coated plates and cultured as a monolayer under MTESR® media (Stemcell Technologies, Vancouver, Canada) for cell expansion. Next, to induce mesodermal differentiation, several combinations of mesodermal inducers were tested and compared by qRT-PCR with mesodermal markers including T (or Brachyury) and KDR. A combination of bone morphogenetic protein 4 (BMP4; 10 ng/mL), activin A (3 ng/mL), and basic fibroblast growth factor (FGF2; 5 ng/mL) was the most efficient for mesodermal differentiation. To induce cardiac lineage differentiation in phase 3, different methods were tested. Supplementation with conditioned media produced by the mouse endodermal cell line END-2 induced the highest expression of cardiac lineage markers such as NKX2-5, TNNT2, MYH6, and MYH-7. Finally, in phase 4, continuous treatment with a β-adrenergic receptor agonist, isoproterenol, for as few as 4 days efficiently generated spontaneously beating cardiomyocytes.

Figure 5F:
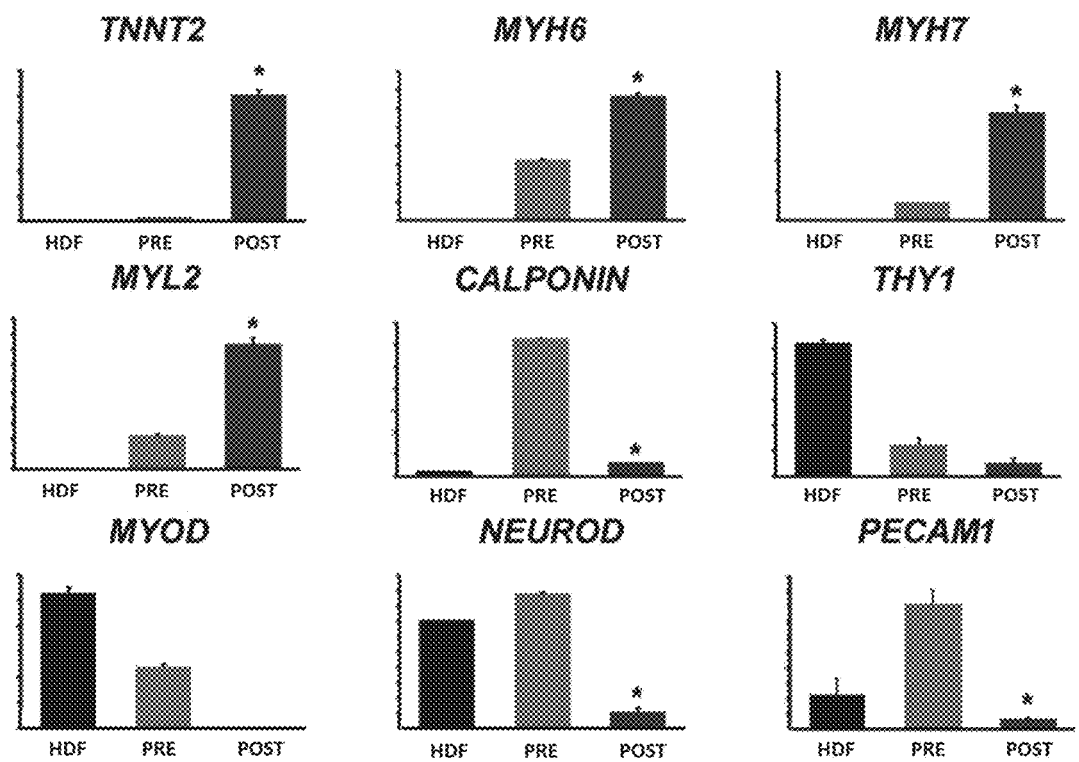
FIG. 5F shows mRNA expression levels of cardiac and noncardiac genes measured by quantitative reverse-transcriptase polymerase chain reaction. Comparisons were made for human dermal fibroblast (HDF), presorted hESCs at day 13 (PRE), and post-FACS-sorted cells at day 13 (POST) using MHC1-MB. Cardiomyocyte genes (TNNT2, MYH6, MYH7, and MYL2) were significantly higher in sorted hESCs than in presorted hESCs and HDF. Expression of the noncardiac lineage genes (PECAM1, CALPONIN, THY1, MYOD, and NEUROD) was significantly lower in sorted cells than in others. The y axis represents relative mRNA expression of target genes to GAPDH. A.U. indicates arbitrary units. *P<0.05 compared with presorted group; n=3.
Figure 5G:
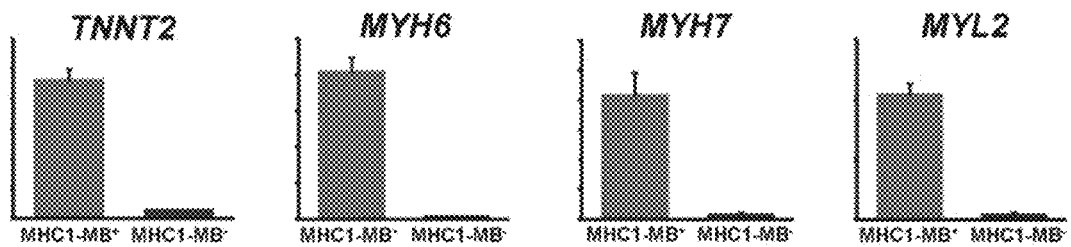
FIG. 5G shows mRNA expression levels of cardiac genes from both MHC1-MB-positive and -negative cells measured by quantitative reverse-transcriptase polymerase chain reaction.

Flow cytometry analysis demonstrated that the percentage of TNNI3-positive cells was 10.2% and 43.1% at days 9 and 13, respectively (FIG. 5B). The MHC1-MB were delivered to the cardiomyogenically differentiated hESCs at day 13 in phase 4. Flow cytometry analysis showed that the percentage of cells positive for MHC1-MB signal was 46.3% (FIG. 5C). These MHC1-MB-treated cells were sorted by FACS, and 97.6±1.4% of the sorted MHC1-MB-positive cells exhibited TNNI3 expression in flow cytometry analysis (FIG. 5D). Almost all cells showed cardiomyocyte-like morphology and stained positive for TNNT2 and TNNI3 by immunocytochemistry (FIG. 5E). qRT-PCR analyses showed a significant increase in expression of cardiomyocyte-specific genes (TNNT2, MYH6, MYH7, and MYL2) and a decrease in expression of genes specific for smooth muscle cells (calponin), fibroblasts (THY1), skeletal myocytes (MYOD), neural lineage cells (NEUROD), and endothelial cells (PECAM1 [platelet/endothelial cell adhesion molecule 1]), which suggests enrichment of cardiomyocytes and elimination of other lineage cells by cell sorting with the MB (FIGS. 5F and 5G).

Figure 5H:
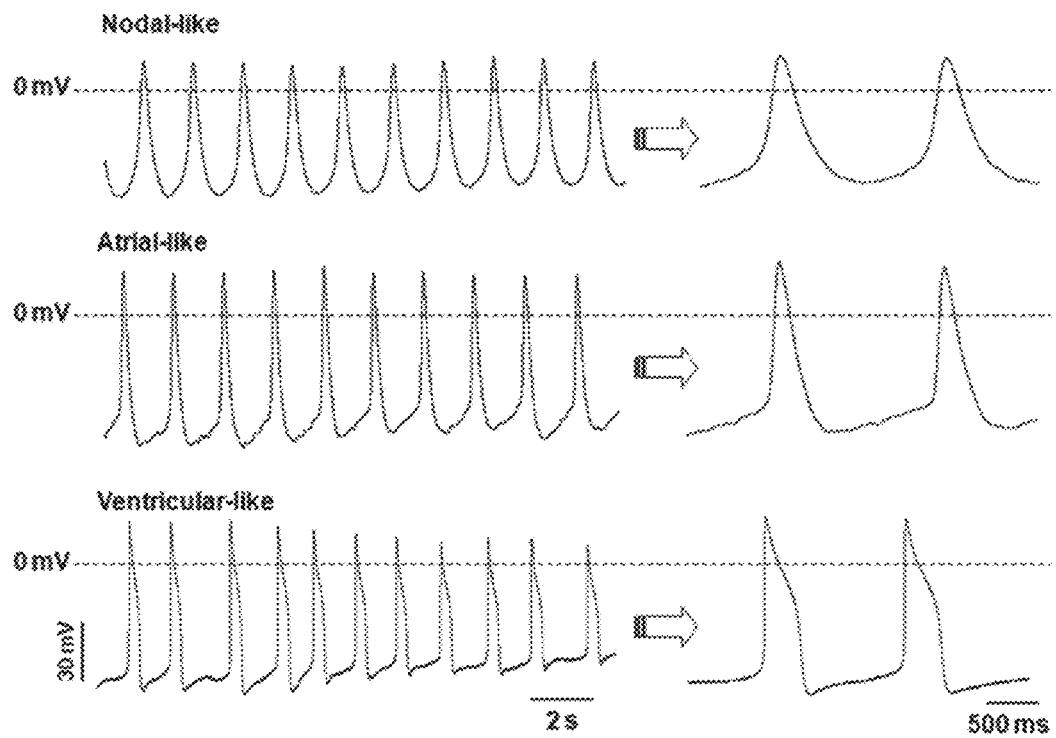
FIG. 5H shows action potentials of MHC1-MB-positive cardiomyocytes. Shown are representative configurations of nodal (top), atrial (middle), and ventricular (bottom) action potentials. hESCs at day 13 of differentiation after applying MHC1-MB. Numbers represent percentages of MB-positive cells (C, D). n=3.

Stable action potentials were recorded from cardiomyocytes that were purified via MHC1-MB and cultured for 7 to 14 days after FACS. Three major types of action potentials were observed: Nodal-like (6 of 46), atrial-like (11 of 46), and ventricular-like (29 of 46) action potentials (FIG. 5H). These results indicate that cells purified via a cardiomyocyte-specific MB are electrophysiologically intact, functional cardiomyocytes and can maintain these characteristics in culture.

Purification of Cardiomyocytes from hiPSCs

Figure 6A:
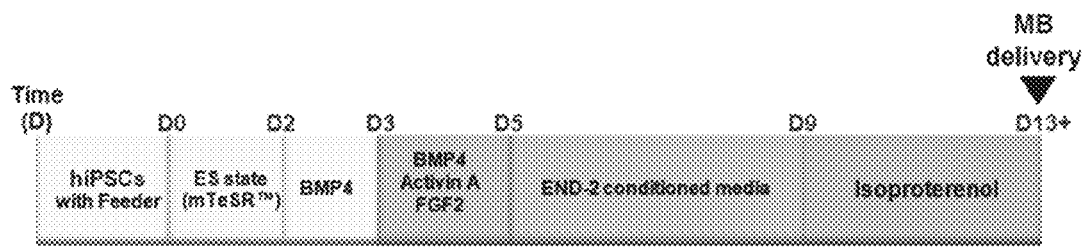
FIG. 6A shows data on the purification of cardiomyocytes from differentiating human induced pluripotent stem cells (hiPSCs) by cell sorting via molecular beacon (MB) and fluorescence-activated cell sorting (FACS). Schematic of the protocol to differentiate hiPSCs to the cardiac lineage. BMP4 indicates bone morphogenetic protein 4; END-2, mouse endoderm-like cells; ES, embryonic stem cells; and FGF2, basic fibroblast growth factor.
Figure 6E:
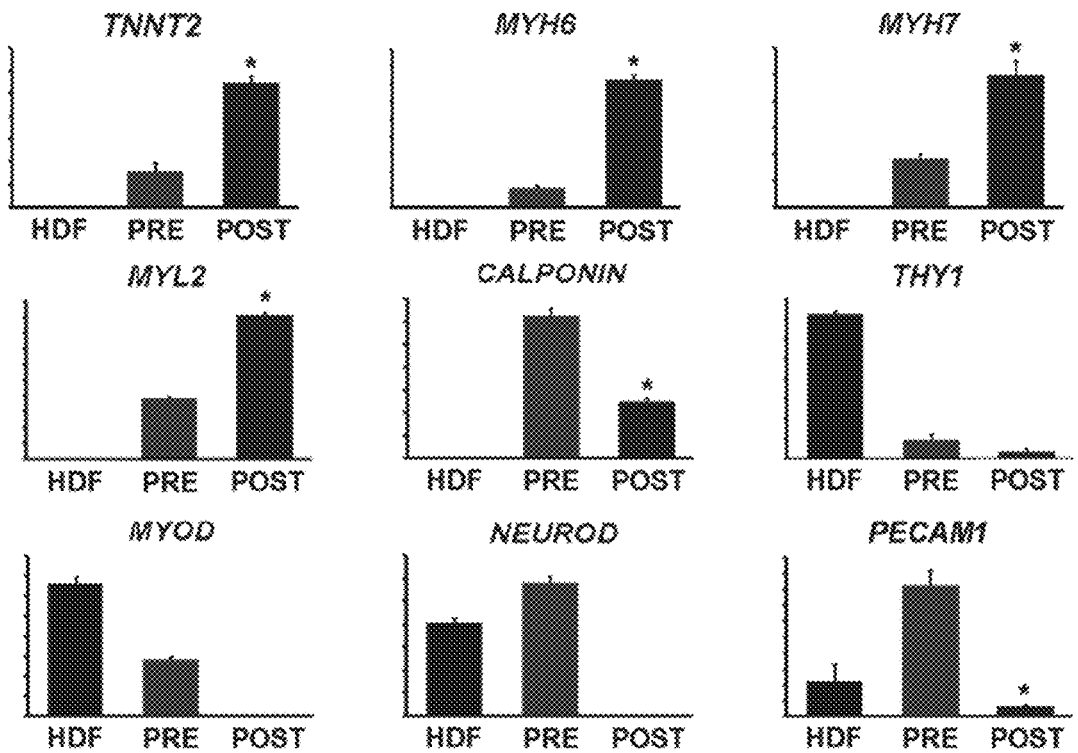
FIG. 6E shows mRNA expression levels of cardiac and noncardiac genes measured by quantitative reverse-transcriptase polymerase chain reaction. Comparisons were made among human dermal fibroblast (HDF), presorted hiPSCs at day 13 (PRE), and MB-based FACS-sorted hiPSCs at day 13 (POST). The y axis represents relative mRNA expression of target genes to GAPDH. A.U. indicates arbitrary units. *P<0.05 compared to presorted group; n=3.
Figure 6F:
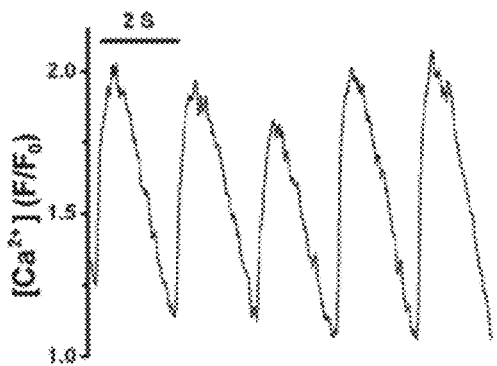
FIG. 6F shows time course of [Ca]2+I, measured at line-scan region in cell pictured and paced at 0.5 Hz by field stimulation. [Ca]2+ is plotted as fluorescence intensity normalized to baseline (F/F0).

The utility of MHC1-MB for isolating cardiomyocytes from differentiating hiPSCs (BJ1) was examined. The differentiation system for cardiomyocytes from hESCs was successfully applied to hiPSCs, yielding 40.7% of TNNI3-positive cardiomyocytes at day 13 (FIGS. 6A and 6B). MHC1-MB was delivered into the differentiating hiPSCs at day 13, and the percentage of cells positive for MHC1-MB as analyzed by flow cytometry was 45.5% (FIG. 6C). FACS based on MB signal resulted in enrichment of TNNI3-positive cells to 97.2±1.9% (FIG. 6D). Almost all the sorted cells stained positive for TNNI3 or TNNT2 in immunostaining. qRT-PCR again showed an approximately 3- to 7-fold increase in cardiomyocyte-specific gene expression and a substantial reduction or negligible levels of other lineage gene expression (FIG. 6E). The sorted MHC1-MB-positive cardiomyocytes showed spontaneous contraction and rhythmic calcium oscillations (FIG. 6F). These data suggest that the MHC1-MB-based purified cardiomyocytes were functional cardiomyocytes. Taken together, the results indicate that MBs that target cardiomyocyte-specific mRNA in live cells allow isolation of functional cardiomyocytes from differentiating mouse and human PSCs with high specificity and efficiency.

Figure 7A:
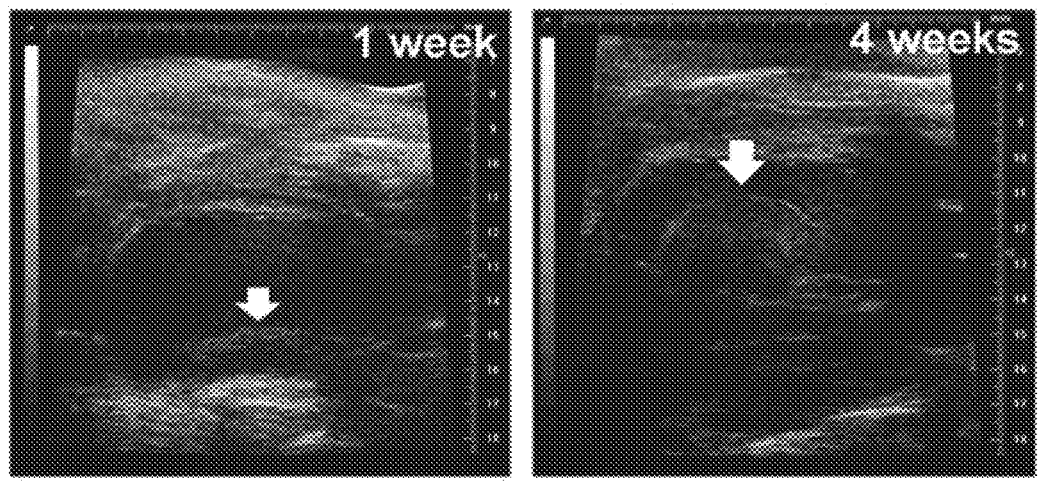
FIG. 7A shows data on the transplantation of unpurified and purified cardio-myocytes into a mouse model of acute myocardial infarction. Serial echocardiography demonstrated a growing left ventricular mass at 1 week (left) and 4 weeks (right) in mice that received unpurified mouse embryonic stem cells (mESC)-derived cardiomyocytes.
Figure 7B:
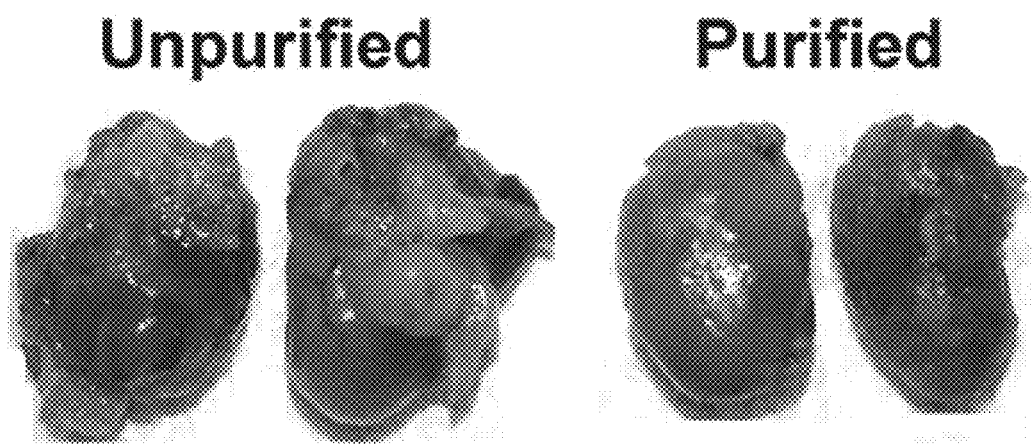
FIG. 7B shows images of excised hearts previously injected with unpurified or purified mESCderived cardiomyocytes.
Figure 7C:
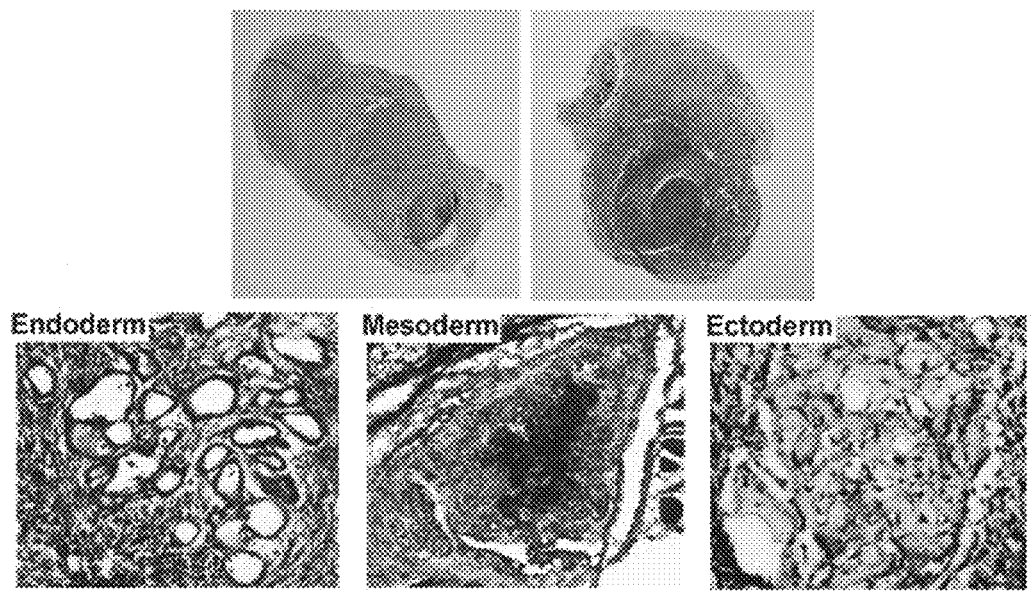
FIG. 7C shows hematoxylin-and-eosin staining of whole cardiac sections demonstrated infiltrative growth of hypercellular tumors surrounding the heart and protruding into the cardiac lumen. Staining revealed cell derivatives of all 3 embryonic germ layers (endoderm, left; mesoderm, middle; and ectoderm, right), indicating teratomas.
Figure 7D:
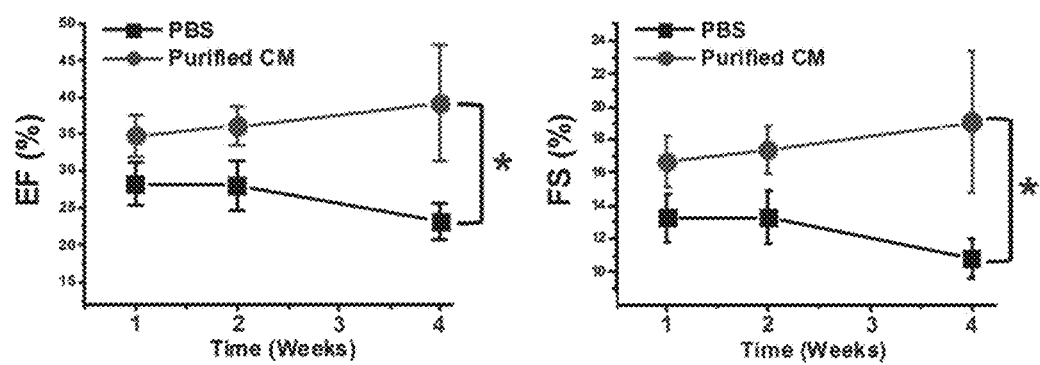
FIG. 7D shows improvement in cardiac function of mice transplanted with molecular beacon-purified cardiomyocytes derived from mESCs. Ejection fraction (EF; left) and fractional shortening (FS; right) were significantly higher in the purified-cardiomyocyte-treated group than in the PBS-treated group, as measured by echocardiography. Repeated-measures ANOVA was used for statistical analyses. CM indicates cardiomyocytes. *P<0.05; n=5 to 10 per group.

Engraftment and Improvement of Cardiac Function after Implantation of Purified Cardiomyocytes To determine the behavior and effects of MB-based purified cardiomyocytes in ischemic myocardium, purified or unpurified cardiomyocytes derived from mESCs or the same volume of PBS was injected into the myocardium after induction of MI in mice. Echocardiography was performed weekly to measure cardiac remodeling and function. One week later, however, in the mice that received unpurified cardiomyocytes, a distinct mass was observed in the left ventricular lumen of the hearts, which grew over 4 weeks (FIGS. 7A and 7B). Postmortem examination at 3 to 4 weeks revealed tumor masses in 11 of 12 mice. By careful gross examination, tumors invaded internally into myocardium and externally into the pericardium (FIGS. 7B and 7C). Cardiac tissues were fixed and stained with hematoxylin and eosin. Microscopic examination revealed that all tumors consisted of structures derived from all 3 embryonic germ layers, which indicates teratomas (FIG. 7C); however, tumors in any of the mice that received MB-based purified cardiomyocytes or PBS over the same follow-up period were not detected by echocardiographic or histological examination. Tumor formation in unpurified cardiomyocyte-injected mice did not allow appropriate functional comparison between mice that received unpurified and purified cardiomyocytes; however, purified cardiomyocyte-injected mice showed a higher ejection fraction than PBS-injected mice (FIG. 7D), which indicates improved cardiac function. Immunohistochemistry for cardiac tissues injected was conducted with purified cardiomyocytes. Confocal microscopic examination demonstrated that injected cardiomyocytes (DiI-positive) were engrafted as clusters, survived robustly for 4 weeks, and expressed representative cardiomyocyte proteins. Taken together, these results suggest that injected MB-purified cardiomyocytes are integrated into ischemic myocardium and are functional in vivo.

Non-Genetic Purification of Ventricular Cardiomyocytes from Differentiating Embryonic Stem Cells Through Molecular Beacons Targeting a Ventricle-Specific Transcription Factor Each type of cardiac chamber-specific CM has unique functional, structural, and electrophysiological characteristics. Thus, transplantation of cardiomyogenically differentiated cells which include heterogeneous CMs and other lineage cells into injured myocardium might induce dysrhythmia, asynchronous cardiac contraction, or aberrant tissue generation. It would therefore be ideal to generate a pure population of ventricular CMs from PSCs to be used for cardiac cell-based therapy.

Prior studies used genetic modifications for isolating ventricular CMs by inserting a fluorescent reporter gene driven by the ventricular myosin light chain 2 (MYL2 or MLC-2v) promoter into mouse ESCs and embryonic carcinoma cell lines. Such genetic modifications preclude clinical use of the cells due to concerns of tumorigenicity or adverse reactions. These ventricular CMs would not be appropriate for drug development or disease modeling either, due to the random and permanent changes in the genome by genetic modifications or the use of viruses. Accordingly, a transient biochemical method for selecting ventricular CMs is needed.

Although not surface markers, there are several genes specifically expressed in ventricular hearts or CMs. As a ventricular-specific transcription factor, Iroquois homeobox protein 4 (IRX4) is expressed in the ventricular myocardium while absent from both atria and the outflow tract. In addition, IRX4 positively regulates ventricular chamber-specific gene expression by activating ventricular myosin heavy chain-1 (VMHC1) while suppressing atrial myosin heavy chain-1 (AMHC1) expression. As a structural protein, MYL2 (or MLC-2v), one of the essential MLC-2 isoforms that is important for the contractile function of ventricular CMs, is expressed in ventricular CMs. MYL2 expression is mostly restricted to the ventricular segment of the heart with minimal expression in the outflow track during cardiogenesis.

Figure 8:
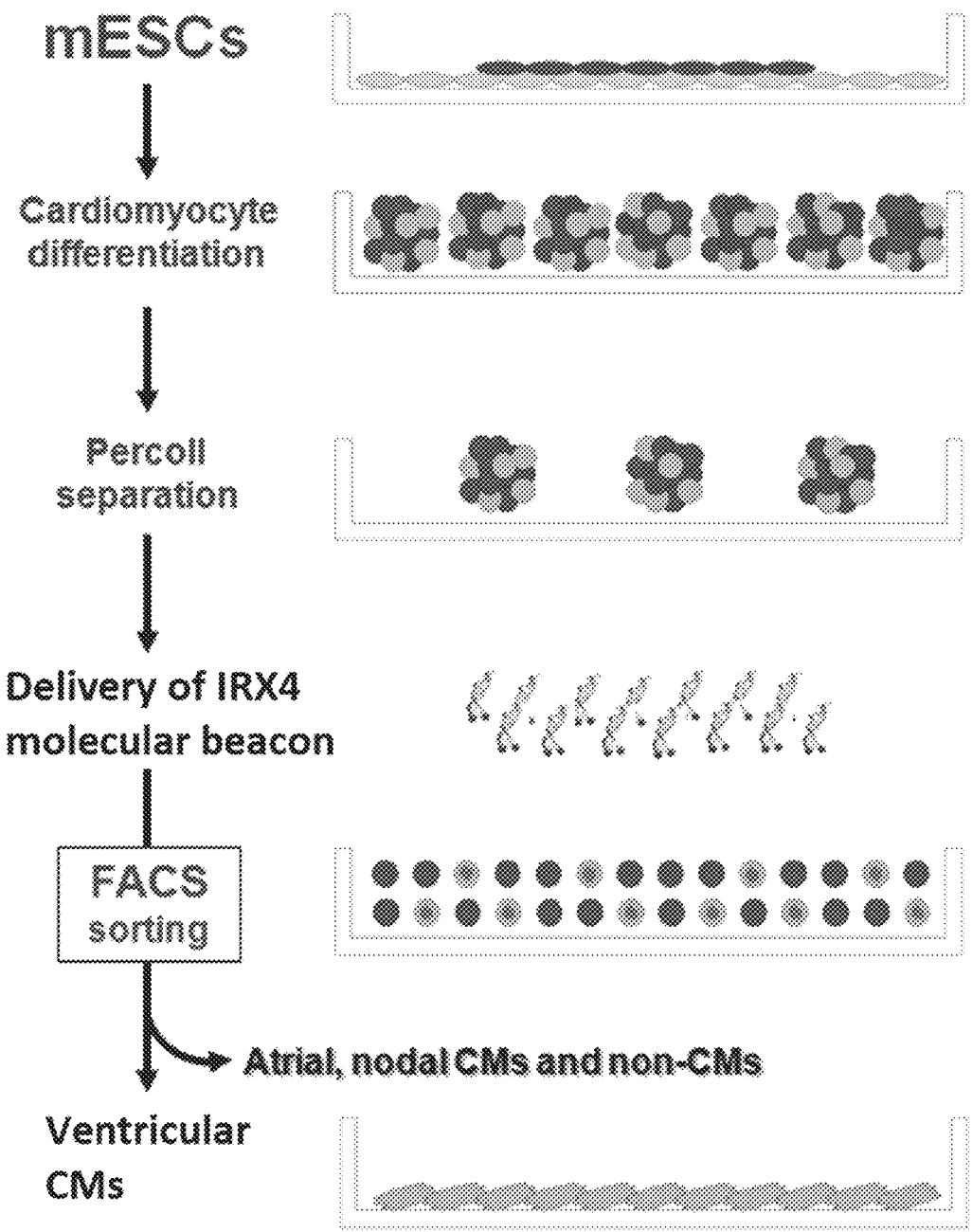
FIG. 8 illustrates an overall strategy to enrich mESC-derived ventricular cardiomyocytes using IRX4 MBs targeting IRX4 mRNA.

MB-mediated targeting of α/β myosin heavy chain (MYH6/7) mRNA followed by FACS sorting can allow purification of general CMs from mouse and human PSCs MBs; however, targeting transcription factor mRNAs which, due to their low copy numbers compared to structural protein mRNAs, are more challenging. By targeting Irx4 mRNA with specific MBs, one is able to enrich functional ventricular CMs derived from differentiating mouse ESCs (FIG. 8). This is the first demonstration that transcription factors can be targeted for MB-based cell sorting.

Ventricular cardiomyocytes (CMs) are a desirable cell type for cardiac repair. However, without specific surface markers, isolation from differentiating pluripotent stem cells (PSCs) has been challenging. Purified ventricular CMs were generated from differentiating mouse embryonic stem cells (mESCs). Different MBs (IRX4-1, -2, -3) were designed to target specific regions of mRNA of iroquois homeobox protein 4 (Irx4), a specific transcription factor for ventricular CMs.

One of these, IRX4-2 MB, showed the highest sensitivity and specificity and was selected to purify mESC-derived ventricular CMs. IRX4-2 MB was applied to cardiomyogenically-differentiating mESC cultures and FACS-sorted IRX4-2 MB-positive cells. Flow cytometry demonstrated that 92 to 97% of IRX4-2 MB-positive cells expressed cardiac troponin 2 (Tnnt2) and myosin light chain 2 ventricular isoform (Myl2). Importantly, about 98% of IRX4-2 MB-positive cells displayed ventricular CM-like action potentials during electrophysiological analyses. These IRX4-2 MB-based purified ventricular CMs continuously maintained their CM characteristics verified by spontaneous beating, Ca2+ transient, and expression of ventricular CM-specific proteins.

Despite the importance of ventricular CMs for cell-based therapy and drug development, no studies reported isolation of ventricular CMs from genetically unmodified stem cells. Homogeneous ventricular type CMs were generated from mESCs, without altering genomes, via MB based sorting for Irx4, a ventricular CM-specific transcription factor. This method yielded functional ventricular CMs with high specificity and efficiency. NUCLEOFECTION® of a selected MB targeting mRNA of Irx4 followed by FACS sorting enabled enrichment of ventricular type CMs to 92% from differentiating mESCs. These purified CMs demonstrated ventricular CM-like action potentials at 98% and Ca' oscillations in electrophysiological studies, suggesting functionally intact ventricular CMs. These cells showed coordinated contraction and survived more than 2 weeks in culture while maintaining their phenotype.

Reported CM differentiation protocols generate heterogeneous CMs mixed with other cell populations. Several recent studies reported non-genetic methods for isolating general CMs. However, these protocols still generate heterogeneous CMs, not chamber-specific CMs. Given the major role of ventricular CMs for cardiac contractile function, there is a need to develop a non-genetic method to isolate ventricular CMs from differentiating PSCs, which will be of value to many preclinical and clinical applications.

Studies reported isolation of ventricular CMs derived from transgenic mESCs or embryonic carcinoma cell lines. For example, ventricular CMs were isolated from genetically modified mESCs in which a fluorescence reporter gene was driven by a promoter of Myl2. While useful for basic research, these genetic methods cannot be used for clinical applications or disease modeling due to genetic modifications. Cell sorting with specific surface markers is a preferred method for isolating target cells from PSC cultures. However, no unique surface markers are known for ventricular CMs, and to identify and validate such markers and develop antibodies would require considerable resources.

Directly targeting intracellular mRNAs of ventricular CM-specific genes is a solution. This approach avoids genetic modifications and the need to identify specific surface markers. Irx4, which is a more specific identifier of ventricular CMs than Myl2. Irx4 plays a role in regulating chamber-specific gene expression in the developing heart and is involved in determining ventricular cell specification. Its expression is restricted to the ventricles throughout the developmental as well as postnatal periods.

As mRNAs of structural proteins are present in abundant copies, the likelihood of successful isolation was relatively high. In fact, another transcription factor, NKX2.5, was initially tried as a target but were not able to sufficiently label general CMs. In this study, the improved design technology enabled us to isolate ventricular CMs by targeting a transcription factor. To prove the specificity in this study, extensive assays were carried out to ensure that the MB signal was a precise indicator of ventricular CMs based on the hybridization of the probe to IRX4. MBs were tested in solution with synthetic target oligonucleotides that varied from the ideal sequences by 6 bp, the closest that a BLAST search through the mouse transcriptome allowed. However, a major challenge was whether the designed MBs could be hybridized to a sufficient quantity of target mRNA sequences to allow sorting of ventricular CMs. Among three designed MBs, one of them, IRX4-2 MB, was bound sufficiently to allow cell sorting.

Another difficulty was to find a delivery method to deliver enough MBs to sufficiently label target mRNAs. Seven transfection methods were tested to deliver MBs into living cells, Streptolysin O, LIPOFECTAMINE® 2000, LULLABY®, electroporation, microinjection and NUCLEOFECTION®, and found that NUCLEOFECTION® in a specific buffer induced maximal target detectability with minimal cell toxicity. Cytotoxic effects of MB themselves within the cells were reported negligible. MBs degrade within a few hours in the cells so that their effects on cell viability or cell identity are low. Even with repetitive transfections of MBs, we did not observe phenotypic or functional changes, as evidenced by unaffected spontaneous contraction and immunocytochemistry assays.

This production of homogeneous and functional PSC-derived ventricular CMs using non-transgenic approach will yield new avenues for clinical and research applications. First, a pure population of ventricular CMs generated by this method offers a safer and effective option for cell therapy and tissue engineering. The mixed populations of PSC derived CMs are more likely to cause abnormal electrical activity or less efficient contractile function. From a research perspective, the MB-purified ventricular CMs represent a powerful in vitro tool for disease investigation and drug discovery. They could be used for better defined in vitro cardiac disease models for genetic or idiopathic cardiac diseases such as long QT syndrome. They can also serve as an in vitro model to test chamber specific effects of cardiac drugs. These purified CMs will yield more accurate genetic and epigenetic information through high throughput sequencing techniques. This MB-mediated cell sorting method can be applied for isolating other cardiac cells such as nodal cells or atrial CMs.

Ventricular Cardiomyocyte-Specific Gene Selection Generation of IRX4 MBs

Irx4 was selected as a target gene for generating ventricular CM-specific MBs. First, mRNA expression levels of Irx4 was measured via quantitative RTPCR (qRT-PCR) analysis in CMs isolated from either ventricles or atria of mouse adult hearts. Myl2, a ventricular CM-specific gene, was measured as a positive control. The results showed that Irx4 is robustly expressed in ventricular CMs but not atrial CMs. The expression levels of both Irx4 and Myl2 mRNAs were substantially higher in mouse ventricular CMs compared to atrial CMs, indicating that Irx4 is a viable target for MB selection.

IRX4 MBs were designed targeting distinct sites on the mouse Irx4 mRNA. In addition, mFold and the RNA Composer Webserver were used to model our IRX4 MBs and to predict binding site availability in the target mRNAs. These IRX4 MBs were synthesized with a Cy3 fluorophore on the 5' end and a BLACK HOLE QUENCHER® 2 on the 3' end as specified in Table 2.

TABLE 2

The list of IRX-4 MBs.

| Beacon Name | Beacon Sequence | Target Sequence | Dye | Quencher |
|---|---|---|---|---|
| IRX4-1 | CACCTAGTTTTGTT ATATTAGCCTCCCT AGGTG (SEQ ID NO. 18) | AGGGAGGCTAA TATAACAAAAC (SEQ ID NO. 21) | Cy3 | BHQ2 |
| IRX4-2 | CCCTGACGTAAACT TTATGCTTCAGGG (SEQ ID NO. 1) | CCCTGAAGCATA AAGTTTACGTC (SEQ ID NO. 22) | Cy3 | BHQ2 |
| IRX4-3 | CAGGCAGAGAGTAG AAAGCAGATGCCTG (SEQ ID NO. 19) | AGGCATCTGCTT TCTACTCTCTG (SEQ ID NO. 23) | Cy3 | BHQ2 |
| IRX4-4 | CAGGCAGAGAGTAG AAAGCAGATGCCTG (SEQ ID NO. 19) | AGGCATCTGCTT TCTACTCTCTG (SEQ ID NO. 23) | Alexa 488 | BHQ1 |
| Control MB | ACGACGCGACAAGC GCACCGATACGTCGT (SEQ ID NO. 20) | GTATCGGTGC GCTTGTCGCG (SEQ ID NO. 24) | Cy3 | BHQ2 |

MB fluorescence signals were quantified when hybridized to perfectly complementary or mismatched synthetic targets by incubating 500 nM MB solution with targets of increasing concentrations (60-500 nM). IRX4 MB signals were recorded using a microplate reader and normalized to the signals in wells with beacon only. IRX4 MBs displayed a linear response to increasing concentrations of complementary targets and a low response to mismatched targets.

Delivery of MBs into the Cells Selection of Optimal IRX4 MB for Identifying Ventricular-Like Cardiomyocytes After attempting several different delivery methods for transfection of MBs, we found that NUCLEOFECTION® with NUCLEOFECTION® Solution V and program A033 (Lonza) was an efficient method to deliver MBs to a variety of cell types. To further refine this system, we also designed two distinct MBs to act as controls. A non-specific interaction indicator MB (RQ) contains a random 20 by loop sequence which is not similar to any known RNA in mouse cells, so any fluorescence would indicate an undesirable mechanism. A confirmation of delivery control MB (UQ) used the same random sequence but does not contain a quencher so that it fluoresces at all times. Both MBs were delivered to cells to ensure that transfection was efficient and that MB signal was specific to the targeted sequence.

Figure 9A:
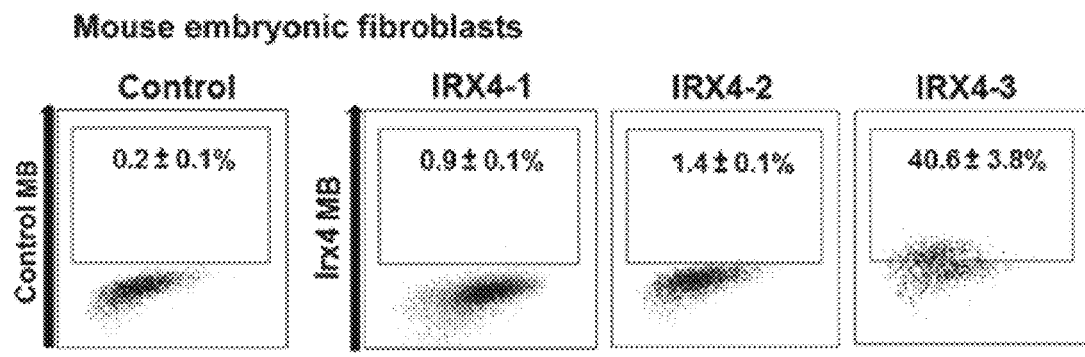
FIG. 9A shows data on the selection of optimal ventricular cardiomyocyte-specific IRX4 molecular beacons. Flow cytometry results after delivering three different IRX4 MBs designed to identify Irx4 mRNAs into mouse embryonic fibroblasts. N=3.
Figure 9B:
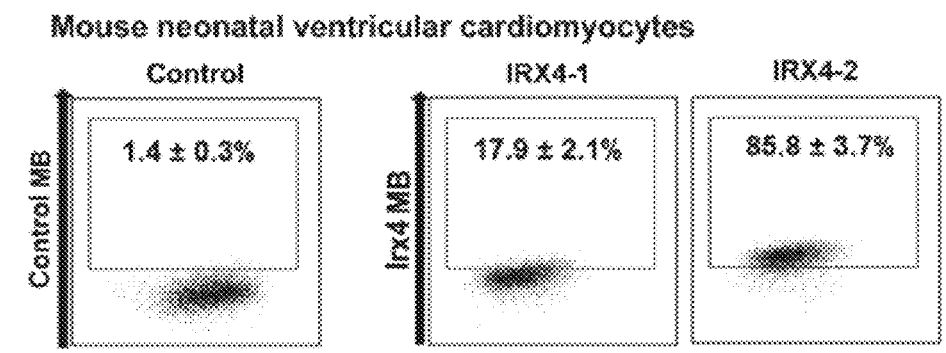
FIG. 9B shows flow cytometric analysis of neonatal mouse ventricular CMs treated with control MB versus two IRX4 MBs targeting Irx4 mRNAs. N=3.

The specificity, sensitivity and reliability of each IRX4 MB was examined in separate systems. To determine the specificity of MBs, each of the IRX4 MBs were delivered into mouse embryonic fibroblasts (mEFs), which do not express IRX4, by NUCLEOFECTION®. The cells were analyzed for false-positive signals using flow cytometry. Among the three MBs (IRX4-1, -2, and -3) examined, the MBs designated as IRX4-1 and IRX4-2 yielded significantly lower rates of MB-positive cells on mEFs (IRX4-1: 0.9±0.1%, and IRX4-2: 1.4±0.1%). In contrast, IRX4-3 displayed a high percentage of false-positive signals (IRX4-3: 40.6±3.8%) in mEFs. Hence both IRX4-1 and IRX4-2 were selected for further experiments. Next, to evaluate the sensitivity of the two candidate MBs (IRX4-1, and -2), each of the candidate IRX4 MBs was delivered into mouse neonatal ventricular CMs and analyzed with flow cytometry. IRX4-2 MB identified a substantially higher percentage of ventricular CMs (85.8±3.7%) compared to IRX4-1 MB (17.9±2.1%). Based on these results, IRX4-2 MB was used as a final candidate for enriching the mESC-derived ventricular CMs (FIG. 9B).

Figure 9C:
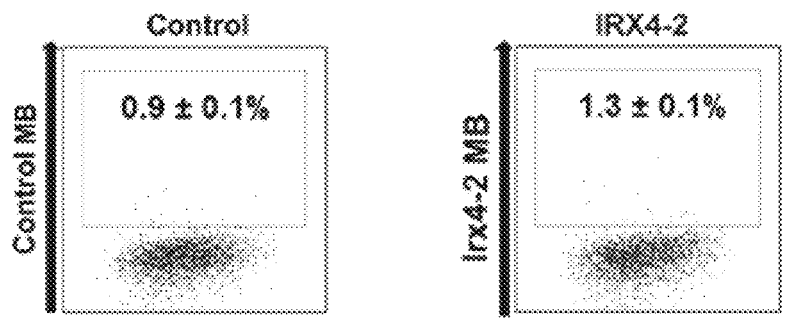
FIG. 9C shows flow cytometric analysis of HL-1 CMs treated with control MB versus IRX4-2-MB. N=3. The numbers in each panel represent the percentages of fluorescent cells.

IRX4-2 MB was examined with HL-1 CMs, an immortalized mouse atrial CM cell line known to retain atrial CM characteristics. The results from flow cytometry analysis demonstrated that less than 2% of HL-1 CMs displayed positive signals for IRX4-2 MBs, further supporting their specificity for ventricular CMs (FIG. 9C). IRX4-2 MBs were tested the against mouse smooth muscle cells (SMCs), mouse aortic endothelial cells (mECs), mouse cardiac fibroblasts (mCFs) and mESCs, which are the most likely contaminating cell types in cardiomyogenically differentiated PSC cultures. Flow cytometry analysis showed that fewer than 3% of those cells displayed detectable fluorescence signals. These results indicate that IRX4-2 MB is specific for identifying ventricular CMs.

Generation of Ventricular CMs from Mouse Embryonic Stem Cells

Figure 10A:
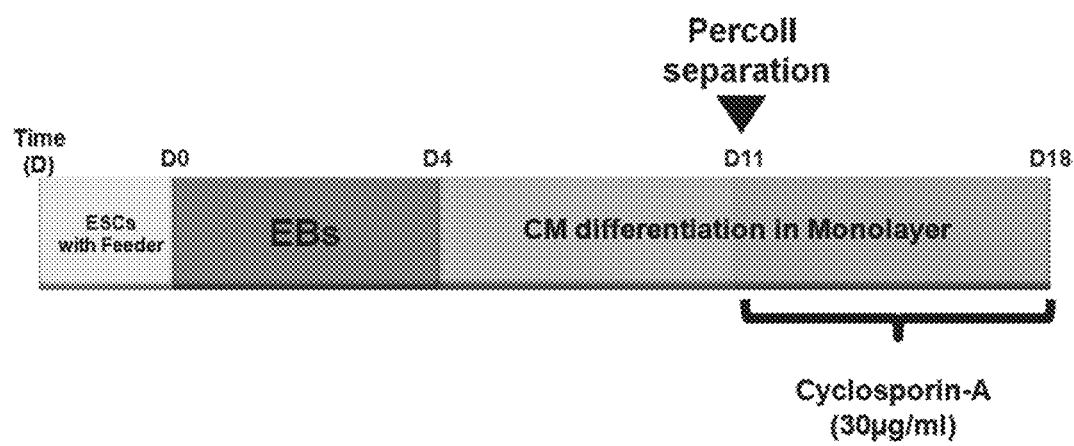
FIG. 10A shows data on the characterization of general and ventricular cardiomyocytes differentiated from mESCs. A schematic of the protocol to differentiate mESCs to the cardiac lineage. ESCs indicate mouse embryonic stem cells; and EB, embryoid body.
Figure 10B:
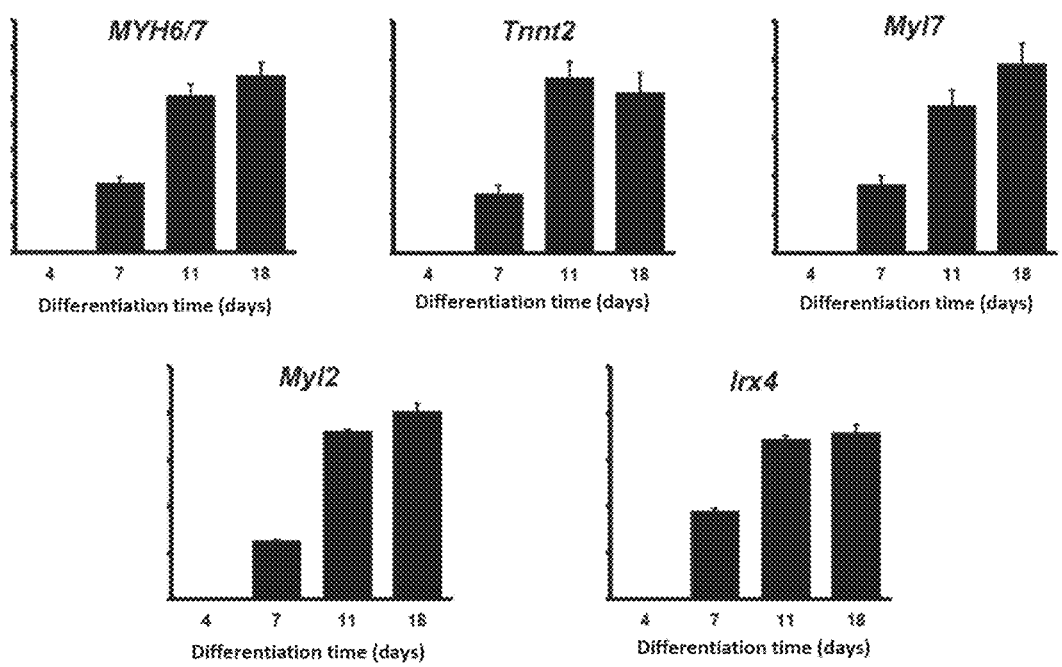
FIG. 10B shows expression profiles of the CM-specific genes (Tnnt2 and Myh6/7) and chamber-specific CM genes (Myl7, Myl2 and Irx4) during cardiomyocyte differentiation from mESCs. Y axis represents relative mRNA expression of target genes to GAPDH. N=3.

To ensure stable production of mESC-derived ventricular CMs, an embryoid body (EB)-mediated CM differentiation system was established (FIG. 10A). Undifferentiated mouse ESCs (J1) maintained on STO feeder cells were enzymatically detached to form EBs. Since EB-induced differentiation alone is not sufficient for producing a high percentage of CMs, day-4 EBs were plated into a fibronectin-coated dish and added ascorbic acid (50 μg/ml) to enhance CM differentiation. Spontaneously beating clumps began to appear 3-4 days after plating. After 7 days of CM differentiation on monolayer cultures, the cells were enzymatically dissociated. They were applied to a discontinuous Percoll gradient (40.5% to 58.5%) to enrich mESC-derived CMs. Percoll mediated-separation typically produces three layers of cells and the bottom layer includes a higher percentage of CMs. Thus, the cells in the bottom layer were collected and cultured for another 7 days in the presence of cyclosporine A (30 μg/ml) to further induce CM differentiation. IRX4 MBs were applied to these 18-day cultured mESC-derived CMs.

qRT-PCR analyses revealed dynamic changes in the expression of CM-specific genes in this differentiation system indicative of efficient CM differentiation. Expression of cardiac contractile genes (Tnnt2 and Myh7), and genes for atrial (Mlc2a), and ventricular CMs (Myl2 and Irx4) began to appear 7 days after culture. Expression of Myl2 and Irx4 continuously increased until day 18 (FIG. 10B).

Immunocytochemistry and flow cytometry were carried out to further characterize the cell population at day 18. Immunocytochemistry demonstrated that day 18 cells significantly expressed CM-specific proteins including ACTN2 (α-sarcomeric actinin), TNNT2 (cardiac troponin T), and MYH6/7 (α and β myosin heavy chain) confirming their CM nature. A substantial number of cells which were positive for ACTN2, TNNT2 and MYH6/7 concomitantly expressed MYL2 (or MLC2V) which is a specific protein for ventricular CMs. Flow cytometry analyses showed that the percentage of TNNT2 and MYL2 positive cells were 67.9±4.5% and 39.2±3.8%, respectively (FIG. 4D). These results indicate efficient generation of CMs with a significant percentage of ventricular CMs through our CM differentiation system.

Purification of mESC-Derived Ventricular-Like CMs Through IRX4-2 MBs

Figure 11A:
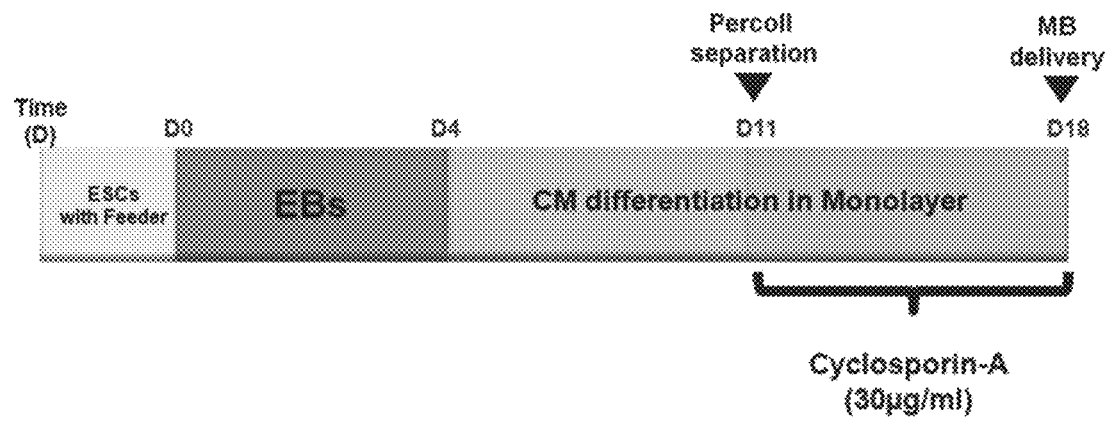
FIG. 11A illustrates and shows data on the purification of ventricular cardiomyocytes from differentiating mESCs through IRX4-2 MBs. A schematic illustrating the time point of delivering IRX4-2 MBs at day 18 in differentiating mESC cultures.
Figure 11B:
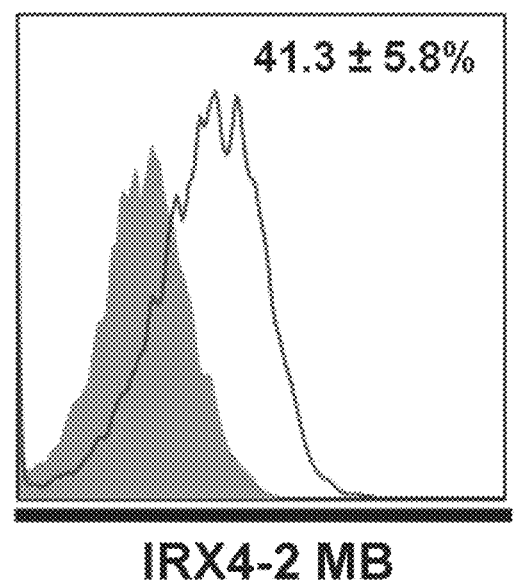
FIG. 11B shows flow cytometry results of IRX4-2 MB-positive cells in mESC differentiation culture at day 18. N=6.
Figure 11C:
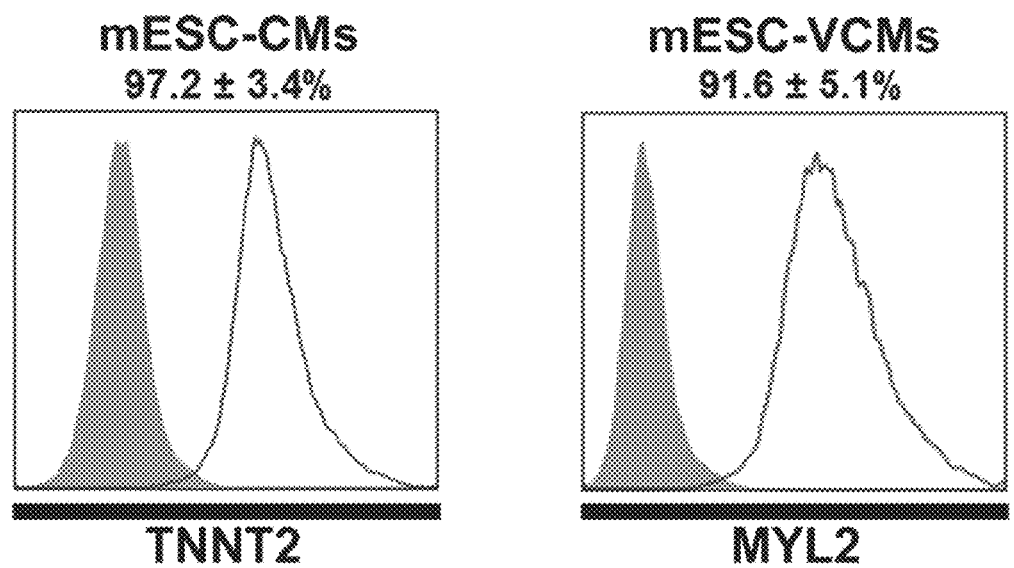
FIG. 11C shows flow cytometry results showing Tnnt2 and Myl2 expression in mESC-derived ventricular cardiomyocytes which were FACS-sorted after delivering IRX4-2 MBs at day 18. N=3.

After establishing the CM differentiation system, IRX4-2 MB was delivered to the 18-day differentiated cells to isolate ventricular-like CMs (FIG. 11). A pre-validated NUCLEOFECTION® protocol was used to deliver the MB and FACS-sort the cells (FIG. 11A). Flow cytometry results showed that 41.3±5.8% of cells were positive for IRX4-2 MB fluorescence signal (FIG. 11B). This number is similar to the detection rate of ventricular CMs using antibody based (39.2% of Myl2-positive cells) methods. FACS-sorting for IRX4-2 MB was conducted and the MB-positive CMs were seeded onto fibronectin coated plates for further experiments. The IRX4-2 MB-positive CMs began to beat spontaneously within 48 hrs and continued to beat vigorously for up to two weeks. Only a small number of cells beat in the IRX4-2 MB-negative plate. 1-3 days after FACS sorting, flow cytometry analyses was conducted using TNNT2 and MYL2 antibodies to quantify the percentage of CMs and ventricular-like CMs in IRX4-2-MB positive cells. Almost all sorted IRX4-2 MB-positive cells expressed TNNT2 and MYL2 (TNNT2: 97.2%±3.4% and MYL2: 91.6±5.1%) indicating efficient enrichment of mESC-derived ventricular CMs by IRX4-2-MB sorting (FIG. 11C).

Electrophysiological Characteristics of Ventricular-Like CMs Through IRX4 MB

Figure 12A:
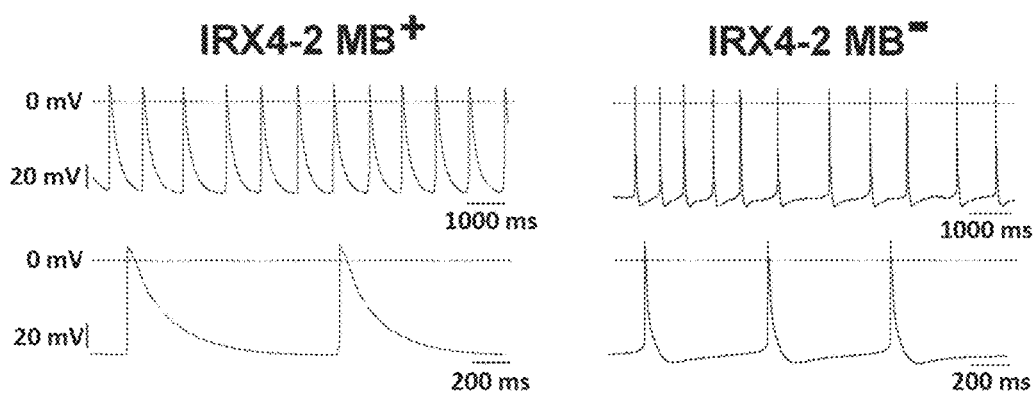
FIG. 12A shows electrophysiological characteristics of IRX4-2 MB-purified ventricular cardiomyocytes Action potentials of the IRX4-2 MB-positive and -negative cells. Shown are representative configurations of the action potentials from IRX4-2 MB-positive (left) and negative cells (right).
Figure 12B:
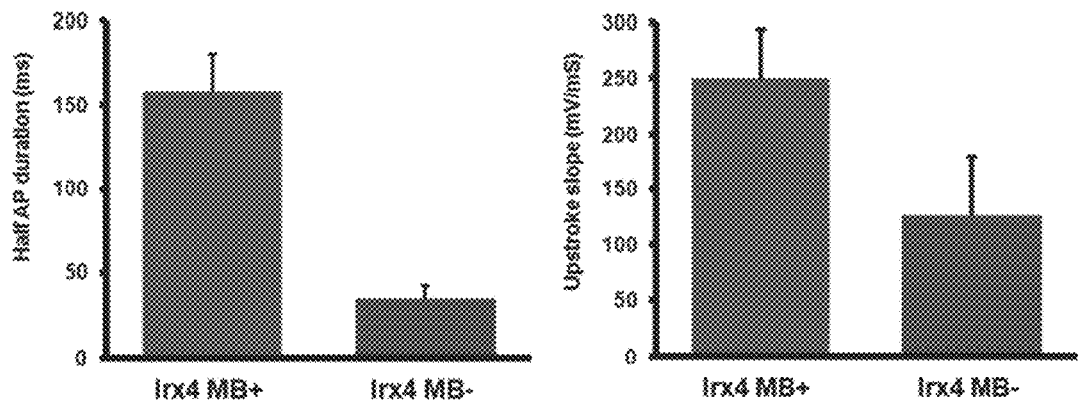
FIG. 12B shows half action potential duration (APD50) and upstroke slope of IRX4-2 MB-positive and negative cells. Action potentials were measured from 50 cells from either IRX4-2 MB-positive or negative cells.
Figure 12C:
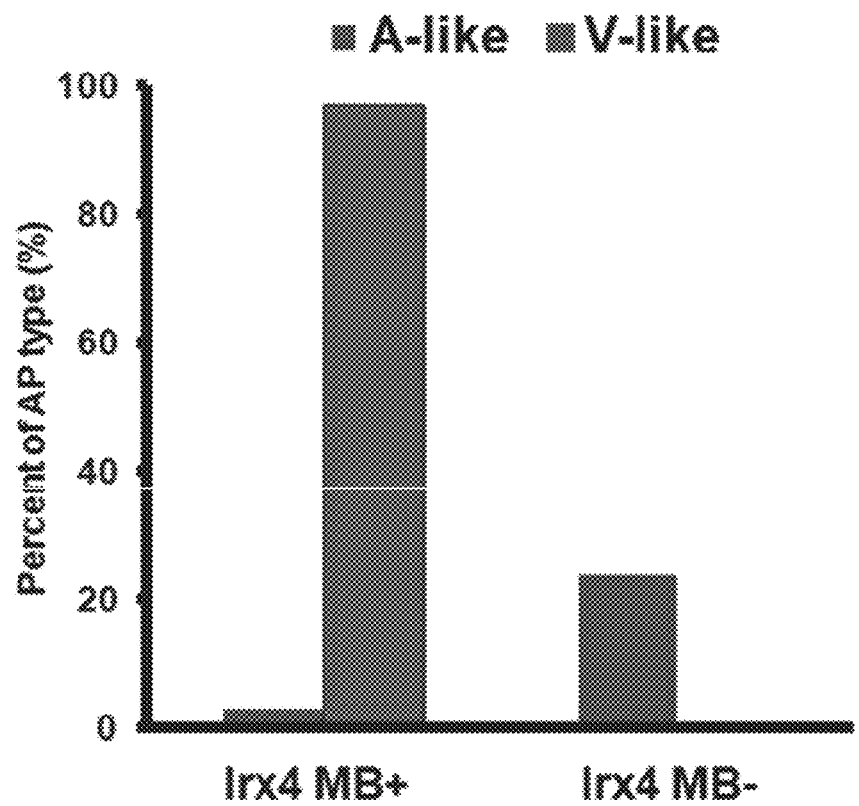
FIG. 12C shows the percentages of the action potential types recorded from IRX4-2 MB positive and -negative cells. A-like: atrial-like AP, V-like: ventricular-like AP.

To investigate the electrophysiological characteristics of IRX4-2 MB-purified ventricular CMs, whole-cell patch clamp analyses was performed (FIG. 12A). It is known that electrophysiological characteristics of ventricular or atrial CMs are distinct. In primary adult CMs, average action potential duration (APD) of ventricular CMs is significantly longer than APDs of atrial CMs. The primary CMs in fetal stage showed similar patterns of APD at 90% of repolarization (APD90; ventricular CMs: 140±7 ms vs. atrial CMs: 95±7 ms). In addition, CMs derived from mESCs displayed similar differences in electrophysiological characteristics between ventricular CM (APD50: 99.3±15.9 ms, APD90: 151.4±22.1 ms) and atrial (APD50: 20.7±7.2 ms, APD90: 60.6±17 ms)38. The APD50 of IRX4-2-MB positive and negative CMs were 159±21.7 ms and 35±7.8 ms, respectively (P<0.01). Furthermore, the average upstroke slope of IRX4-2-MB positive and negative CMs were 251±43.7 and 126.7±51.9 mV/ms, respectively (P<0.01) (FIG. 12B). Based on these results, 98% of IRX4-2 MB-positive cells possessed ventricular-type APs (49 out of 50 cells) whereas atrial or nodal-type APs were not observed. Approximately 24% of IRX4-2 MB-negative cells exhibited an atrial-like AP (12 out of 50 cells) (FIG. 12C).

Figure 12D:
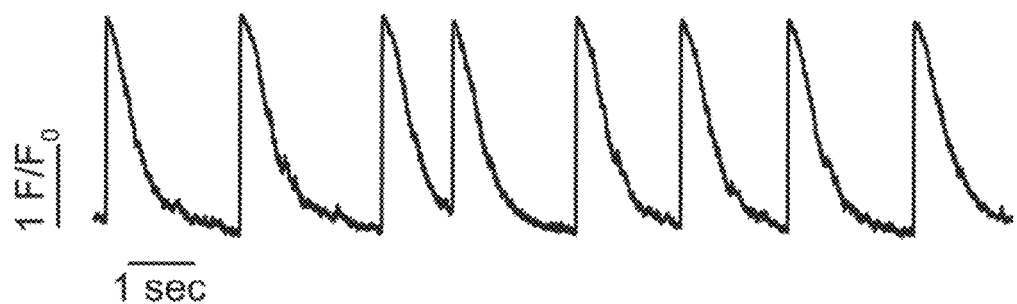
FIG. 12D shows calcium transients in IRX4-2 MB-positive ventricular CMs sorted from mESCs. Upper panel is a line scans of spontaneous calcium transients recorded across a beating cell, purple to yellow color gradient indicates increasing calcium. Lower panel demonstrates average calcium transient measured from line scan where fluorescence is normalized to baseline at time 0.

To determine the contractile properties of IRX4-2 MB-based sorted CMs, we performed real-time intracellular calcium imaging analysis. FIG. 12D shows a two-dimensional scan of an enriched ventricular CM loaded with Fluo. Spontaneous calcium transients were recorded in the upper panel, where increasing calcium is indicated by the change in color from dark blue to light blue, and fluorescence intensity is normalized to the baseline measured at time 0 (Fo). Average calcium intensity along each point of the line is shown in the lower panel indicating a cyclic calcium transient. Collectively, these results indicate that the majority of the enriched IRX4-2 MB positive cells were functionally intact ventricular CMs.

Cellular Characterization of FACS-Sorted Ventricular CMs

Figure 13:
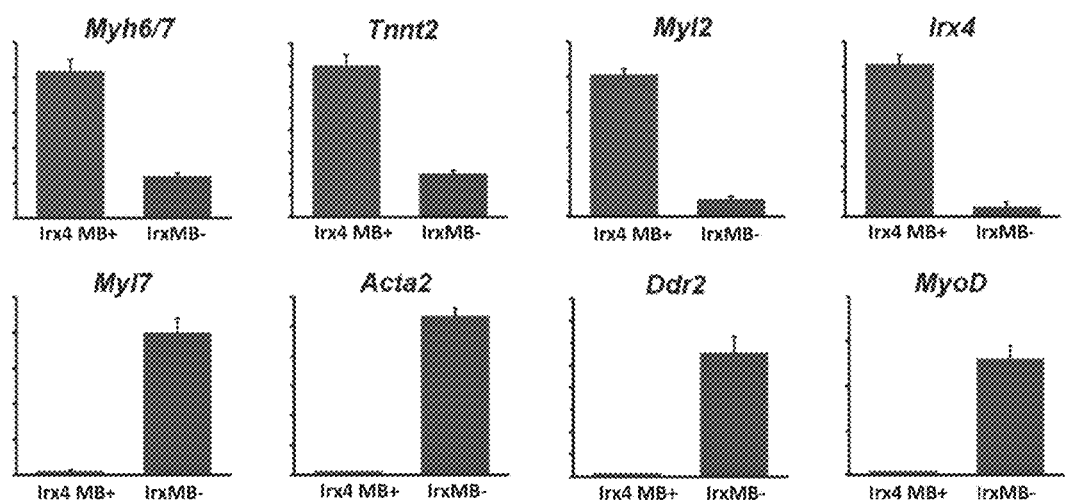
FIG. 13 shows data on characterization of purified ventricular CMs through IRX4-2 MBs mRNA expression of cardiac and non-cardiac genes in IRX4-2 MB-positive and negative cells measured by qRT-PCR. Y axis represents relative mRNA expression of target genes to GAPDH. *P<0.05 compared to pre-sorted group. N=3.

To examine the cardiac identity and homogeneity of the ventricular CMs purified with IRX4-2 MB, immunocytochemistry was conducted with antibodies against various CM specific markers (ACTN2, TNNT2 and MYH6/7 and MYL2) and ventricular CM marker (MYL2) 2-3 days after FACS sorting and cultures. Immunocytochemistry demonstrated that almost all IRX4-2-based enriched ventricular CMs exhibited ACTN2, TNNT2, and MYH6/7. Furthermore, a positive immunoreactivity for MYL2 was found in all of the IRX4-2 MB-positive ventricular CMs. Importantly, these IRX4-2 MB-positive ventricular CMs abundantly expressed GJA1 (known as connexin 43), an important connexin isoform in the formation of gap junctions between ventricular CMs, indicating that these enriched ventricular CMs possess the functional capability of forming cardiac junctions. qRT-PCR analyses further demonstrated that expression of ventricular CM genes Irx4 and Myl2 as well as general CM genes were substantially enriched in IRX4 MB-positive cells compared to the IRX4 MB-negative cell population (FIG. 13). Furthermore, these IRX4 MB-positive cells showed a significant increase in expression of general CM-specific genes (Tnnt2, and Myh6/7) compared to the IRX4 MB-negative cells (FIG. 13). Genes representing atrial specific CMs (Myl7) or other cell types were either expressed at negligible levels (Acta2, Ddr2, and MyoD) or were non-detectable (Pecam1, and Neuro D) in the IRX4 MB-positive cells (FIG. 13). Taken together, the data indicates that IRX4-2 MBs that target ventricular CM-specific mRNA in live cells allow isolation of functional ventricular CMs from differentiating mESCs with high specificity and efficiency.

Isolation of any Cell from Differentiating Human Mixtures Using Molecular Beacons Cardiomyocytes (CMs) derived from pluripotent stem cells (PSCs), including embryonic stem cells (ESCs) and induced pluripotent stem cells (iPSCs), are a source for regenerating damaged cardiac tissues. In addition, the PSC-derived CMs are useful for modeling genetic diseases such as long QT syndrome 1 (LQT1) and drug testing for various cardiac diseases. PSC-derived CMs possess a clear cardiac phenotype displaying spontaneous contractile activity, cardiac-type mechanisms of excitation-contraction coupling, and expression of expected sarcomeric proteins, ion channels, and transcription factors. Transplantation of PSC derived CMs into rodent models induced cardiac repair through enhancement of cardiac function.

Although the following protocol is focused on the isolation of CMs from differentiating human PSCs, it can be applied to the isolation of CMs from mouse PSCs with minimal alterations. There are five elements of the MB isolation protocol to consider for isolation of specific cells types from differentiating PSCs: (1) identification of specific mRNAs that are highly and uniquely expressed in the specific cells types; (2) design and validation of MBs targeting cell-specific mRNAs with high signal-to-background ratio; (3) delivery of MBs into a mixed population of cells from differentiating PSCs with high efficiency and throughput; (4) high-throughput isolation of the target cells with FACS based on MB signal; (5) validation of specific cell type characteristics using electrophysiology and immunocytochemistry. Although the experimental design described here is focused on the isolation of CMs, the MB-based method is quite general and can be readily modified for the isolation and enrichment of other cell types by designing MBs to target the specific gene(s) highly expressed in the particular cell type.

In order to use MBs to isolate specific cells from a mixed cell population, target mRNAs that are highly and uniquely expressed in the cell type of interest should be identified. These mRNAs should to have a relatively high abundance so that, when MBs are hybridized to their mRNA target in the specific cells (such as CMs), the resulting fluorescence signal is at least 5-fold higher than that in other cell types. Genes encoding structural proteins involved in the contractile process are the most logical choice for CMs. However, for isolating other cell types it typically requires that the gene expression profiles are quantified using qRT-PCR (or DNA microarray) to identify specific mRNAs that have high levels (>10 fold) compared with that in other cell types in the mixed cell population in the PSC differentiation culture. It is important to choose multiple target genes highly expressed in the cell type of interest so that at least one mRNA would be specific enough and result in high MB signal.

Once CM-specific genes are identified, MBs can be designed by targeting regions of the corresponding mRNA where excellent probe accessibility and signal specificity can be achieved. The target sequences of a specific mRNA may not be accessible due to secondary structure of the mRNA or RNA-binding proteins. To enhance target accessibility, an RNA secondary structure prediction program (e.g., mFOLD) can be used to identify potential single-stranded regions of the mRNA. It is also important to select target sequences with a sufficient (35%-65%) GC content so that MBs so designed would have a good affinity to their targets. Finally, NCBI BLAST search is typically performed to identify unique sequences of the mRNA for MBs to target (target sequences), and to minimize the number of sequences that differ from a target sequence by only a few (<5) bases. Since it is impossible to accurately predict target accessibility in living cells, multiple (3 three to five-5) candidate MBs are usually designed and tested for against a specific mRNA.

An important issue with the MB-based approach is signal specificity. Ideally, MBs delivered into a mixed cell population exhibit a high level of signal only in CMs but not in other cell types due to the high expression of the target gene in CM cells. However, in certain cases, a high level of non-specific signal from MBs may occur due to delivery, MB degradation, or MB-protein interactions in cells. To determine MB signal specificity, a negative-control random MB was designed whose probe sequence does not match with any mRNA sequence in the mouse or human genome. Any signal from the random MBs after delivery into HL-1 cells (a cell-line derived from mouse atrial CMs) would be non-specific background signal. The ratio of MB signal from CM-specific mRNA and background signal from random MB gives the signal-to-background ratio, S/N. To have high signal specificity, a well-designed the MB should have a S/N>5 in CMs.

There are several MB delivery methods, including the use of microinjection, cell penetration peptides (CCPs), streptolysin O (SLO), and electroporation. Microinjection is low-throughput, and often interferes with normal cell function. Although the CCP- or SLO-based delivery of MBs could have high efficiency and throughput, the delivery efficiency is typically cell-type dependent, so it may not work for the mixed cell population resulting from PSC differentiation. Further, when using CCPs or SLO for MB delivery, MBs might be trapped in endosomes and degraded there, causing a high level of background signal. Electroporation has been used to deliver oligonucleotides to living cells, but conventional methods may result in low cell viability. Recent advances in electroporation technology (such as NUCLEOFECTION®) have led to a reduction in the harmful events, including heat generation, metal ion dissolution, pH variation, and oxide formation. The advanced electroporation methods could lead to cellular internalization of oligonucleotide probes with high transfection efficiency (>90%) and high cell viability (>80%). Using NUCLEOFECTION®, it is possible to uniformly deliver MBs into millions of cells within 20 min.

Figure 14A:
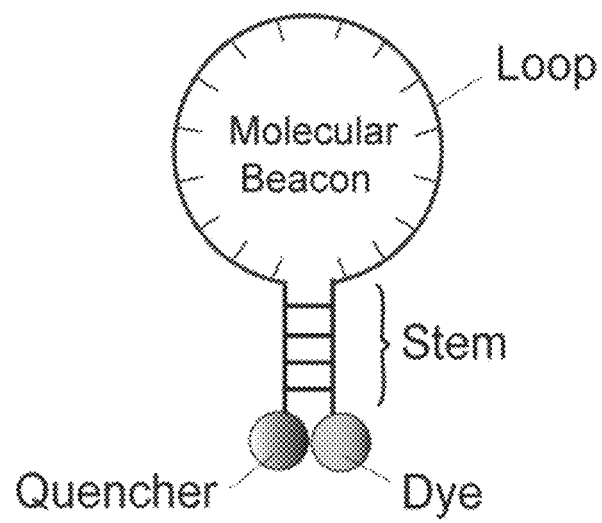
FIG. 14A illustrates molecular beacon structure and control molecular beacons. A schematic of a molecular beacon in a stem-loop hairpin conformation. The stem brings the 5' dye and 3' quencher together to quench the fluorescence signal. The loop region with 15-30 base pairs is complementary to the target sequence of specific mRNA thus providing specificity.
Figure 14B:
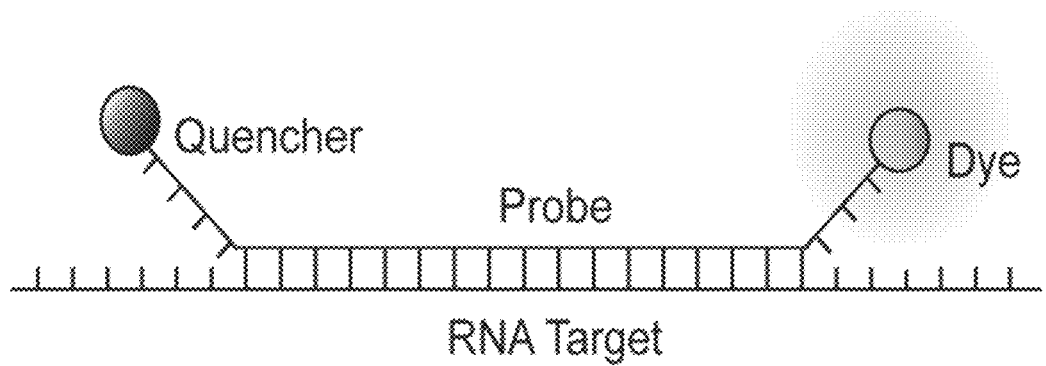
FIG. 14B shows a schematic depicting a molecular beacon in an open conformation after hybridizing to its complementary target mRNA sequence. Hybridization induces a conformational change that separates the fluorophore from the quencher, resulting in a >10-fold increase in fluorescence signal.
Figure 14C:
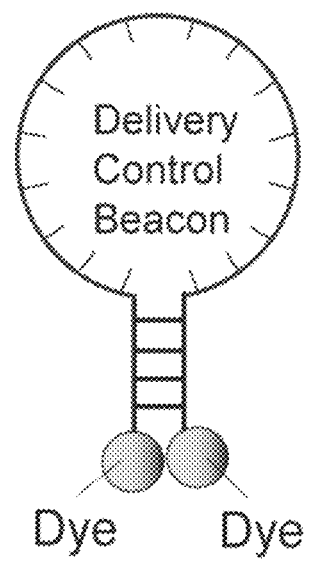
FIG. 14C shows a schematic of a positive control molecular beacon with a fluorescent dye attached to both the 5' and 3' ends, thus is constitutively fluorescent. This probe is used to determine if MBs can be delivered into different cell types efficiently and uniformly.

One particular issue is to make sure that the difference in MB signal in the mixed cell population, especially that between CMs and other cell types is not an artifact due to delivery preferential uptake of MBs by a specific cell type. It is therefore important to ensure that cells in the mixed population take up beacons MBs uniformly. To this end, the random-sequence MB is modified to have two identical fluorophores instead of a dye-quencher pair (FIG. 14C) and used as a positive-control probe for delivery studies. After probe delivery into differentiating cells, fluorescence signals are quantified and a relatively uniform signal distribution is expected. This experiment is designed to confirm that the MB signal specificity is due to MB hybridization to target mRNAs rather than MBs preferentially entering one cell type.

To ensure that a high purity CM population is isolated from differentiating PSCs, MB-positive cells should be tested to ascertain that (i) they highly express CM-specific genes and (ii) they have low (or zero) expression levels of genes associated with other cell lineages. CM specific markers such as TNNT2, TNNI3, MYH6/7, and MYL2 can be analyzed in the MB-positive population using both RT-PCR and immunocytochemistry to yield both population-based results and quantitative information on the number of cells expressing specific markers. It is also important to demonstrate that the MB-positive cells do not express genes that are markers of other cell types, including skeletal muscle, neural progenitor cells, fibroblasts and endothelial cells. To ensure that the MB-positive cells represent a high purity population of CMs, a high percentage of cells expressing CM specific markers and a low percentage of cells expressing markers indicating other cell lineages are required.

It should be noted that MBs are suitable for the detection of abundantly expressed mRNAs and should be delivered to cells and analyzed very rapidly. While MBs do increase their fluorescent intensity by an order of magnitude upon binding their complementary target, cells take up between 2,000 and 20,000 MB per transfection. In order to yield a 2 to 1 increase in fluorescent intensity, the number of transcripts are typically therefore approximately 10% of the number of MB delivered, e.g. at least 200 copies per cell. In addition, MB should be delivered to cells quickly because of the inherently short functional lifespan of exogenous nucleic acid sequences in a cellular environment. We have therefore used NUCLEOFECTION® to deliver MB to the cytoplasm of large numbers of cells and MB signals are detected or measured in less than 4 hours to avoid potential artifact. This makes MB ideal for secreted or structural proteins.

Protocol for Preparing of High-Purity Cells (Cardiomyocytes) from Differentiating Pluripotent Stem Cells Using Molecular Beacons Steps 1-7: CM specific-MB Design Considerations Timing—10 Days Step 1: Identify CM-specific genes. Identify genes highly expressed in CMs such as cardiac troponin T (cTNnT) and a/13 myosin heavy chain (MYH6/7) based on literature search. Check if these genes are also highly expressed in other cell types in the mixed cell population during PSC differentiation.

Step 2: Confirm high gene expression levels using qRT-PCR. Using at least 100,000 cells from the specific cell population and prepare total RNA with the RNEASY® mini plus kit according to the manufacturer's instructions. Convert the RNA into cDNA using the iScript cDNA synthesis kit from BioRad. Perform either TAQMAN® or SYBR® Green real-time PCR using a 7500 Fast Real-Time PCR system. Run all annealing steps at 60° C. Normalize all target genes to GAPDH in multiplexed reactions performed in triplicate. Calculate differences in CT values ($\Delta$CT=CT gene of interest-CT GAPDH in experimental samples) for each target mRNA by subtracting the mean value of GAPDH (relative expression=2-$\Delta$CT).

Step 3: Predict the secondary structure of the target mRNA. Enter the sequence into a secondary structure prediction program (e.g., mFOLD) to generate best guesses for single stranded regions so that MBs would have good accessibility to the target sequence.

Step 4: Design the MB loop region. Identify a sequence of 15-30 bases of the target mRNA predicted to be single stranded. Select a region with 35%-65% GC content, and design a complementary sequence with a predicted melting temperature (Tm) of 60° C. in 150 mM NaCl when hybridizes to the target mRNA. This sequence (the reverse complement of the target sequence) will form the loop of the MB.

Step 5: Add the stems onto the MB loop. Add a stem to the loop sequence by appending complementary arms of 5 bases long to the 3' and 5' end of the loop sequence respectively. MBs with a total length of more than 40 bases may form a secondary structure therefore should be avoided. It may be desirable to add only one arm with a 5-base sequence complementary to the loop sequence on the opposing end in order to create a shorter MB (shared-stem MB). A 5-base stem with a GC content of ~60% should be strong enough to generate a stem-loop hairpin structure with a Tm of ~50° C. Do not use Guanine for the first 3 bases at the 5' end due to its tendency to quench fluorophores.

Figure 14D:
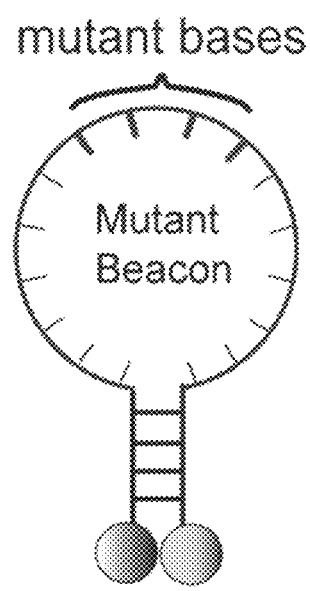
FIG. 14D shows a schematic depicting a specific negative control beacon. The four mutated bases should prohibit hybridization of the probe to the target region of specific mRNA. When delivered into HL-1 as positive control cells, this control beacon should yield very low background signal, confirming the MB specificity.

Step 6: Use in silico analysis to avoid foreseeable errors in MB design. Use the NCBI BLAST search tool to identify other mRNAs that the MB may hybridize to in the cell type of interest. Use the MB sequence as input. The closest match should be the targeted mRNA sequence from Step 4, and the second closest match should have at least 4 base pairs mismatch compared with the mRNA target sequence. For the validation step, test both the MB formed using the mRNA target sequence and the control MB (mutant MB, see FIG. 14D) formed using the second closest sequence (mismatched sequence) from the Blast search.

Step 7: Select the fluorophore-quencher pair and order the MB and oligonucleotide targets. Steps 1-6 identify three oligonucleotide sequences, a MB with its loop and stem sequences, the target sequence, and a mismatch (mutant) sequence. To form the MB, select a dye-quencher pair and conjugate the dye and quencher to the 5' and 3' ends of the MB sequence respectively. The most affordable options are the Fam fluorophore with BLACK HOLE QUENCHER® 1 or the Cy3 fluorophore with BLACK HOLE QUENCHER® 2. Use the Cy3 dye for experiments where another molecule is taking up the FITC/GFP wavelengths. Attach the quencher to 3' end to ensure that all MBs will have a quencher even if the fluorophore is not conjugated to the MB due to a synthesis error. For labs without an oligonucleotide synthesizer facility, it is recommended to order MBs from one of the many high quality oligonucleotide providers such as MWG Operon or IDT, where HPLC purification of the MBs to eliminate the free dye is performed. To determine MB performance, the synthetic target oligonucleotide (usually single strand DNA) with the same sequence as target mRNA, and mutant (mismatched) oligonucleotide should also be ordered for MB characterization in solution. MBs with DNA backbones are sufficient for CM isolation. It may be important to design and test several CM-specific MBs which can be ordered simultaneously to reduce wait times. Resuspend all oligonucleotides in nuclease-free, 0.1× TE, pH 7.0 buffer at 100 µM to make stock solutions. Avoid freeze-thaw cycles to preserve stability and function of MBs. Pause point: MB can be stored at −20° C. or −80° C. for up to 6 months after synthesis.

Steps 8-10 MB Validation in Solution

Timing—2 Hours

Step 8: Design and test several CM-specific MBs hybridizing to different sequences of the target mRNA. Use Optimem or a similar buffer to make a 500 µL aliquot of 1 µM CM-specific MB. In separate tubes use the same buffer to dilute the target oligonucleotide and mismatched oligonucleotide to 1.5 µM. Make serial dilutions of the target oligonucleotide and the mismatched oligonucleotide to establish dose dependence.

Step 9: Mix solutions in a 384 well black-bottomed plate. Add 25 µL of MB solution to each well of a 384-well black-bottomed plate, then add 25 µL of each concentration of the solutions containing target oligonucleotide or mismatched oligonucleotide to their designated wells. Include one blank well and one well with DNAse 1 as negative and positive controls, respectively.

Step 10: Analyze the fluorescence intensity of MBs using a microplate reader. Establish a dose dependence curve using the serial dilutions of the target oligonucleotide. The MB signal at the highest target oligonucleotide concentration is generally between 5 and 30 times higher than the background signal quantified in the negative control experiment in which the signal level of MBs without any target is measured. The MB signal in the well with the highest concentration of mismatched oligonucleotide should be no more than 1.5 times the background signal. Candidate MBs that do not meet these conditions should be disregard due to lack of specificity and low S/N. MBs that satisfy these conditions are selected for further testing.

If no MB meets these conditions, MBs should be redesigned. If the MBs highly fluoresce in the presence of a mismatched oligonucleotide, increasing the stem length by adding a basepair may solve the problem. If the MBs do not fluoresce at all in the presence of the target oligonucleotide, weaken the stem by removing a basepair from the stem or changing a C-G pair to an A-T pair in the stem.

Steps 11-12: MB delivery testing with mouse embryonic fibroblasts (MEF) NUCLEOFECTION® is an electroporation method for transferring nucleic acids such as DNA and RNA molecules into cells. Under typical NUCLEOFECTION® conditions, MBs are delivered into both the cell cytoplasm and the cell nucleus. Since the target mRNAs are only in the cell cytoplasm, MBs delivered into the cell nucleus should result in a very low background signal. To check the efficiency of MB delivery via NUCLEOFECTION® and select optimal delivery conditions, a delivery control MB (FIG. 14C) is designed which has a non-specific, 'random' sequence with two FAM dyes conjugated to both 5' and 3' ends, allowing the probe to fluoresce without any target when delivered into MEF cells using NUCLEOFECTION®.

Timing—1 Day

Step 11: Deliver positive control MBs into a control cell line using NUCLEOFECTION®. Plate MEF cells at 50-60% confluency in DMEM medium containing 10% vol/vol FBS and culture them overnight at 37° C. Add the delivery control MB (FIG. 14C) to the NUCLEOFECTION® solution to reach 500 nM MB concentration. Detach one million cells per condition, wash with PBS, and resuspend in the NUCLEOFECTION® solution containing delivery control MBs. Use a gentle centrifugation of 90 g for 10 minutes to avoid damaging the cells. Perform NUCLEOFECTION® using a variety of programs to identify the optimal program with the highest uniform delivery efficiency. Immediately after NUCLEOFECTION®, gently pipette cells from the cuvette into cell culture medium and keep them there for at least 10 minutes. Ensure that all PBS is removed from the solution to avoid diluting the electroporation solution.

Step 12: Analyze cells using flow cytometry. After MB delivery, gently centrifuge the cells at 90 g's for 10 minutes, then aspirate the media. Resuspend the cells in PBS and analyze the cells using any standard flow cytometer. For flow cytometry assays, first run an untransfected sample. Use this non-fluorescent sample to set the lower limits of gates which can be used to detect MB positive cells.

A high percentage of cells should display high fluorescence signal from the delivery control MBs after MB delivery. If fewer than 80% of the cells are positive for MB signal (MB-positive), continue to test other electroporation parameters to increase the transfection rate, repeating steps 10 and 11 until a satisfactory percentage (e.g., >80%) of MB-positive cells is achieved.

Steps 13-15 MB specificity testing in HL-1 CMs and non-CM cells as positive and negative controls, respectively
Timing—1 Day Step 13: Deliver MBs into HL-1 CM cells using NUCLEOFECTION®. Use the optimized NUCLEOFECTION® parameters and the procedure described in Step 11 to deliver the CM-specific MBs designed and tested in Steps 8-10 into HL-1 cells, which should result in a strong fluorescent signal. Then deliver the random sequence, negative control MB (FIG. 14C) into a separate aliquot of HL-1 cells to ensure that the false positive signal resulting from non-specific opening of the random MB is low.

Step 14: Deliver CM-specific MBs into non-CM cells using NUCLEOFECTION®. Deliver the CM-specific MBs into non-CM cells (such as smooth muscle cells, aortic endothelial cells and cardiac fibroblasts) typically present in the differentiating PSCs. Use the optimized NUCLEOFECTION® parameters and the procedure described in Step 11; the MB signals in these cells should be low.

Step 15: Analyze all cells after MB delivery using flow cytometry. After MB delivery, incubate cells for 10 min at 37° C., gently centrifuge the cells at 90 g's for 10 minutes, then aspirate the media. Resuspend the cells in PBS and analyze the cells using any standard flow cytometer. Use negative control cells to set the gates as in Step 12.

The flow cytometry analysis should be performed within 2 hours of MB delivery into the cells. Several groups have shown that non-specific MB signal may increase quickly ~2 hours after MB delivery due to MB degradation, resulting in a high level of false positives in flow cytometry analysis.

If any of the CM-specific MBs generates low fluorescent signal from HL-1 CMs or produces a high level of false positive signal from non-CM cells, Steps 1-10 should to be repeated to identify a better CM-specific MB. In addition, double check that the non-CM cell types do not express the target gene(s) using qRT-PCR. If the target gene is not expressed in non-CM cells but CM-specific MBs fluoresce in these cells, more specific MBs should to be designed and tested to avoid the non-specific signals.

Step 16: Select the final CM-specific MBs. Repeat steps 13-15 to select the final MB designs which result in high fluoresce signal in positive control cells (such as HL-1) AND and very low background fluoresce signal in negative control cells (such as non-CM cells). These MBs will be used for further study for the isolation of hPSC-derived CMs. In most of the cases, one CM-specific MB that has satisfactory performance (high positive signal and low background signal) would be sufficient.

Step 17-20 Stem Cell Differentiation
Timing—~2-3 Weeks

Step 17: Culturing undifferentiated hPSCs. Culture hPSCs on mitotically inactivated MEF (STO) cells in DMEM/F12 supplemented with 20% serum replacement, 1% L-glutamine, 1% nonessential amino acids, 100 mM β-mercaptoethanol, and 4 ng/ml basic fibroblast growth factor. Change the medium every day and transfer hPSCs to new feeder cells every 5 to 7 days. Culture cells for at least 1 passage after thaw before beginning differentiation.

Step 18: Begin 2D hPSC differentiation. Dissociate undifferentiated hPSCs to small clusters (10-20 cells) by treatment with Dispase (1 mg/ml) and directly transfer them onto growth factor reduced Matrigel-coated plates as a two dimensional culture. Culture the cells for 24-48 hrs in MTESR® media (STEMCELL Technologies) for their expansion.

Step 19: Induce mesodermal differentiation. Incubate cells in media with a combination of BMP4 (10 ng/ml), Activin A (3 ng/ml) and FGF2 (5 ng/ml) for 2 days. Remove the cytokine media and add END-2 conditioned media produced by mouse endodermal cell line END-2 for 4 days.

Step 20: Supplementation with Isoproterereol to produce mature CMs. Remove conditioned media and incubate cells with the media containing isoproterenol (10 μM), a β-adrenergic receptor agonist, for at least 4 days to generate spontaneously beating CMs.

Alternatively, prepare CMs differentiated from hPSCs using any of the previously validated protocols, see below:

Laflamme et al., Cardiomyocytes derived from human embryonic stem cells in pro-survival factors enhance function of infarcted rat hearts. Nat Biotech 25, 1015-1024 (2007)

Yang et al., Human cardiovascular progenitor cells develop from a KDR+ embryonic-stem-cell-derived population. Nature 453, 524-528 (2008)

Lian et al., Robust cardiomyocyte differentiation from human pluripotent stem cells via temporal modulation of canonical Wnt signaling. Proceedings of the National Academy of Sciences, 2012, (10.1073/pnas.1200250109).

Boheler et al., Differentiation of Pluripotent Embryonic Stem Cells Into Cardiomyocytes. Circulation Research, 2002, 91, 189-201

Steps 21-25 Deliver MBs into differentiating hPSCs for the isolation of CMs
Timing—6 Hours Step 21: Deliver control MBs in the differentiated cells using NUCLEOFECTION®. Detach one million cells from differentiating hPSCs obtained from steps 17-20 using Accutase, wash with PBS, and resuspend in the NUCLEOFECTION® solution containing 500 nM of delivery control MBs. Use the optimal NUCLEOFECTION® program identified to deliver MBs into the mixed cell population. Use a gentle centrifugation of 90 g for 10 minutes to avoid damaging the cells. Immediately after NUCLEOFECTION®, gently pipette cells from the cuvette into the DMEM/F12 medium containing 10% vol/vol FBS and incubate cells for 30 minutes at 37° C.

Step 22: Analyze signal from delivery control MB in cells using a flow cytometer. Gently centrifuge the cells at 90 g's for 10 minutes, then aspirate the media. Resuspend the cells in PBS and analyze the cells using any standard flow cytometer. Cells in the mixed cell population should show uniform, high fluorescence signal. Use negative control cells to set the gates as in Step 12.

If the signal level is low or the fluorescence signal has a high variation in different cell types, repeat Steps 11-12 to identify the optimal NUCLEOFECTION® program.

Step 23: Deliver CM-specific MBs into differentiating hPSCs using NUCLEOFECTION®. Detach one million cells from differentiating hPSCs generated from steps 17-20 using Accutase, wash with PBS, and resuspend in the NUCLEOFECTION® solution containing 500 nM of CM-specific MBs. Use the optimal NUCLEOFECTION® program identified to deliver MBs into the mixed cell population. Use a gentle centrifugation of 90 g for 10 minutes to avoid damaging the cells. Immediately after NUCLEOFECTION®, gently pipette cells from the cuvette into at least 1 mL of DMEM/F12 medium containing 10% vol/vol FBS and incubate the cells for 10 minutes at 37° C.

Step 24: Analyze cells using a flow cytometer. Gently centrifuge the cells at 90 g's for 10 minutes, then aspirate the media. Resuspend the cells in PBS and analyze the cells using any standard flow cytometer. Use negative control cells to set the gates as in Step 12.

If none of the cell types (especially CMs) in the mixed cell population has a high level of MB signal, the target mRNA may be inaccessible or underexpressed. Check the expression level of the target gene in the mixed cell population with qRT-PCR. If the target gene is highly expressed in the cells from differentiating PSCs and MBs do not fluoresce, redesign MBs to target a different region of the target mRNA to improve MB accessibility.

Step 25: Sort cells using fluorescence activated cell sorter. Gently centrifuge the cells at 90 g's for 10 minutes, then aspirate the media. Resuspend in PBS and sort the MB-positive cells using a cell sorter such as the FACS ARIA II® or a JAZZ® system. Use slightly more stringent gating conditions than in the previous analysis (Step 24) to ensure high purity of isolated CM cells. Plate cells on appropriate dishes (MEA plates, 6 well dishes, etc) in the DMEM/F12 media containing 10% vol/vol FBS and incubate for 24-28 hours for subsequent CM characterization assays.

Steps 26-28 Characterize CMs Purified with CM-Specific MBs

Timing—2 Days

Step 26: RT-PCR of sorted CMs. Using at least 100,000 cells from Step 25, prepare total RNA with the RNEASY® mini plus kit according to the manufacturer's instructions. Convert the RNA into cDNA using the iScript cDNA synthesis kit from BioRad. Perform either TAQMAN® or SYBR® Green real-time PCR using a 7500 Fast Real-Time PCR system. Run all annealing steps at 60° C. Normalize all target genes to GAPDH in multiplexed reactions performed in triplicate. Calculate differences in CT values ($\Delta CT = CT$ gene of interest $-CT$ GAPDH in experimental samples) for each target mRNA by subtracting the mean value of GAPDH (relative expression=$2-\Delta CT$). It is recommended to test at least 3 genes from each potential lineage (CM, fibroblast, neural, etc.). The specific group of genes may vary depending on the MB target gene.

Step 27: Immunocytochemistry of sorted CMs. Rinse the MB-positive cells with PBS then fix them using 4% paraformaldehyde for 10 min at room temperature. Wash cells twice with PBS and permeabilize them with 0.1 or 0.5% Triton X-100 in PBS for 10 min. Block with 1% BSA in PBS for 60 min at room temperature and then incubate cells with either anti-ACTN2 (1:100), mouse anti-TNNT2 (1:100), or rabbit anti-cTnI (1:100) at 4° C. overnight. Wash the cells three times with 1% Tween 20 in PBS and incubate with anti-mouse IgG-Alexa Fluor 594 (1:1000) or anti-rabbit IgG-Alexa Fluor 488 (1:1000) in PBS for 1 h at room temperature. Counterstain the nuclei with DAPI. Visualize the samples using a fluorescent microscope or confocal laser scanning microscope. Alternatively, cells can be detached at the beginning of this procedure and analyzed using a flow cytometer.

Step 28: Characterization of sorted CMs by intracellular flow cytometry based on the expression of cTNT. Wash the MB-positive cells three times with PBS and centrifuge at 600 g for 5 min at RT. Fix the cells with 2% (wt/vol) PFA for 20 min at room temperature. Wash the cells two times with PBS and centrifuge at 600 g for 5 min at room temperature. Gently resuspend the cell pellets to the permeabilization buffer containing 5% (vol/vol) FBS and 0.5% (vol/vol) saponin, and incubate for 20 min for permeabilization. Prepare the primary antibodies, mouse anti-cTNT, in staining buffer with 0.2% saponin, and add them in the tube with a final antibody dilution of 1:100 for cTNT. Incubate overnight at 4° C. Wash the cells three times with staining buffer and centrifuge at 600 g for 5 min at room temperature. Resuspend the cell pellets in staining buffer with saponin with a 1:200 dilution of secondary antibody, Cy3 goat anti-mouse (Jackson). Incubate the suspensions for 1 hr min at room temperature. Wash the cells three times with staining buffer and centrifuge at 600 g for 5 min at room temperature. Resuspend the cells in 100 µl of PBS with 2% (vol/vol) FBS to quantify cTNT positive cells by flow cytometry.

Maintain the samples in the dark by covering them with aluminum foil after the addition of secondary antibody.

Steps 29-30: Measure Action Potential in Purified CMs

Step 29: Plate cells and prepare the cell culture on a microscope compatible slide. Transfer the MB-positive cells onto 0.1% fibronectin-coated glass bottom microwell dishes and culture them for 7 days. Mount the 35-mm dishes on an inverted microscope and heat the stage to 37° C. with a heating/cooling bath temperature controller. Perfuse the cells with Tyrode's solution.

Step 30: Characterize sorted CMs by action potential measurement. Record intracellular membrane potential using the EPC 7 amplifier in current clamp mode at 37±0.5° C. Impale individual cells with the sharp microelectrodes and record the action potential signals. Analyze action potentials using the Origin 6.0 software.

Cell Culture

HL-1 CMs, a cell line derived from adult mouse atria50, was received from Dr. William Claycomb (Louisiana State University, New Orleans, La., USA). The HL-1 CMs were plated in a dish coated with 12.5 µg/ml fibronectin (Sigma) and 0.02% gelatin (Sigma), and maintained in complete Claycomb medium (Sigma) supplemented with 100 µM norepinephrine (Sigma), 0.3 mM L-ascorbic acid (Sigma), 4 mM L-glutamine (Gibco) and 10% FBS (Sigma) in a 5% $CO_2$ atmosphere at 37° C.

Mouse ESC Culture and Differentiation

The mESCs (J1) were maintained in high glucose Dulbecco's Modified Eagle Medium (DMEM) supplemented with 10% FBS (Atlanta Biologicals), 1% non-essential amino acids solution, 1% L-glutamine, 0.1 mM β-mercaptoethanol, 1% penicillin/streptomycin and 2,000 U $mL^{-1}$ mouse LIF (Millipore) on feeder layers of mitotically inactivated STO cells (ATCC), a cell line of mouse embryonic fibroblasts. Prior to differentiation, mESCs were passaged twice on gelatin-coated dishes to remove the STO cells.

To differentiate mESCs into cardiac lineage, an embryoid body (EB) method was employed. EBs were formed by suspending the cells at 107 cells/mL in 10 mL of differentiation media; alpha-modified Eagle medium (αMEM; Invitrogen) supplemented with 15% FBS, 1% non-essential amino acids, 1% L-glutamine, 1% β-mercaptoethanol, L-ascorbic acid (50 µg/ml; Sigma), and 1% penicillin/streptomycin. By day 1, cells aggregated to form EBs. Differentiation medium was changed every day. 5 days after initiation of EB formation, floating EBs were enzymatically dissociated by treatment with Accutase (e-bioscience) and were transferred into fibronectin-coated plates. These EB-dissociated cells were cultured in non-serum culture medium: DMEM/F12 (Invitrogen) supplemented with norepinephrine (100 µM)) and L-ascorbic acid (50 µg/ml) for further differentiation into CMs. Typically, beating cells appeared on day 7.

Human PSC Culture and Differentiation

Undifferentiated hPSCs including both hESCs and hiPSCs were cultured on mitotically inactivated STO cells in DMEM/F12 supplemented with 20% serum replacement (Invitrogen), 1% L-glutamine, 1% nonessential amino acids, 100 mM β-mercaptoethanol, and 4 ng/ml basic fibroblast growth factor (bFGF; R & D systems). The medium was changed every day and the hPSCs were transferred to new feeder cells every 5 to 7 days. To direct the differentiation of hPSCs to the cardiac lineage, we designed a staged protocol that is divided into four distinct phases. In phase 1, undifferentiated hPSCs were dissociated to small clusters (10-20 cells) by treatment with Dispase (1 mg/ml; Invitrogen) and directly transferred onto growth factor reduced Matrigel (BD Biosciences)-coated plates as a two dimensional culture. These cells were cultured for 24-48 hrs in MTESR® media (Stem cell technology) for their expansion. Next, in phase 2, to induce the expanded hPSCs into mesodermal lineage, a combination of BMP4 (10 ng/ml), Activin A (3 ng/ml) and FGF2 (5 ng/ml) was added for 2 days. In phase 3, differentiating hPSCs were cultured in END-2 conditioned media for 4 days. To produce END-2 conditioned media, mouse endodermal cell line END-2 cells (gift from Dr Christine Mummery) were cultured in DMEM/F12 media supplemented with 1% Insulin-Transferrin-Selenium (ITS; Invitrogen), 1% penicillin-streptomycin, and 0.1 mM β-mercaptoethanol at a seeding density of 5.0×104 cells/cm2 in 0.1% gelatin coated T-75 flasks (Fisher Scientific). After 3 days of culture, the supernatant was collected, filter-sterilized through a 0.22-µm filter (Nalgene) and stored at −80° C. until further use. Finally, in phase 4, continuous treatment with ☐☐adrenergic receptor agonist isoproterenol (10 µM) for as short as 4 days efficiently generated spontaneously beating CMs.

Molecular Beacon Synthesis and Characterization

Five MBs were synthesized by MWG Operon using standard resin-based synthesis methods with HPLC purification to ensure purity. Beacons were re-suspended in nuclease free TE buffer, pH 8.0 to maximize beacon stability. Beacons were tested against synthetic 20-30 by complementary sequences in PBS solution to verify their activity. To demonstrate specificity, beacons were also tested against synthetic targets with 6 by mismatches. Any beacons showing an increase in signal to noise ratio of more than 50% after 2 hours at 37° C. with the mismatched beacons were not used for further testing, which excluded the MHC2 beacon.

NUCLEOFECTION®

NUCLEOFECTION® was employed for delivering MBs into various types of live cells. Target cells were dissociated by treatment with Accutase (e-bioscience) and filtered through a 40-µm cell strainer (BD science) immediately before NUCLEOFECTION®. The dissociated cells (0.5-1× 106) were carefully suspended in 100 µl of NUCLEOFECTOR® Solution V (Lonza) maintained at room temperature, and 0.5 µl of 500 nM MB was added for each reaction. NUCLEOFECTION® was performed using a NUCLEOFECTOR® II (Amaxa Biosystems) set to the A033 NUCLEOFECTOR® program. After termination of NUCLEOFECTION®, 500 µl of cold DMEM/F12 media was added to the reaction cuvette and the contents were gently transferred into a clean tube by a flexible pipette (Lonza). All procedures for NUCLEOFECTION® were performed inside a biological safety cabinet (Labconco) in the dark to prevent light induced non-specific reaction of MB. Subsequently, 1 ml of pre-warmed DMEM/F12 media was added into each tube and further incubated in a 5% CO2 atmosphere at 37° C. for 10 min for MB reaction.

Flow Cytometry

After NUCLEOFECTION®, cells were centrifuged at 2000 rpm for 2 min, re-suspended in DMEM/F12 basal media, and maintained on ice for 20 min to recover. Cells were then analyzed by C6 Flow Cytometer (BD Biosciences) or sorted using a BD FACS ARIA II® cell sorter (BD Biosciences). Beacon signal was recorded using a 561 nm laser with a 585/15 nm emission filter to optimally excite and detect Cy3. Data were analyzed using FlowJo software (Treestar).

RT-PCR

Total RNA was prepared with the RNEASY® mini plus kit (QIAGEN) according to the manufacturer's instructions. The extracted RNA (100 ng to 1 mg) was reverse transcribed into cDNA (reverse transcription) via TAQMAN® reverse transcription reagents including random hexamers, oligo (dT), and MultiScribe™ MuLV reverse transcriptase (Applied Biosystems). qPCR was performed on a 7500 Fast Real-Time PCR system (Applied Biosystems) using Fast SYBR Green master mix (Applied Biosystems). All annealing steps were carried out at 60° C. Relative mRNA expression of target genes was calculated with the comparative CT method. All target genes were normalized to GAPDH in multiplexed reactions performed in triplicate. Differences in CT values (ΔCT=CT gene of interest−CT GAPDH in experimental samples) were calculated for each target mRNA by subtracting the mean value of GAPDH (relative expression=2−ΔCT).

Immunocytochemistry

Cells were fixed with 4% PFA for 10 min at room temperature, washed twice with PBS, and permeabilized with 0.1% Triton X-100 in PBS for 10 min. Cells were then blocked with 1% BSA in PBS for 60 min at room temperature and incubated with anti-ACTN2 (Sigma; 1:100), mouse anti-TNNT2 (NeoMarkers; 1:100), or rabbit anti-cTnI (Abcam; 1:100) at 4° C. overnight. The cells were washed three times with 1% Tween 20 in PBS and incubated with anti-mouse IgG-Alexa Fluor 594 (Invitrogen; 1:1000) or anti-rabbit IgG-Alexa Fluor 488 (Invotrogen; 1:1000) in PBS for 1 h at room temperature. DAPI was used for nuclear staining. The samples were visualized under a fluorescent microscope (Nikon) and a Zeiss LSM 510 Meta confocal laser scanning microscope and LSM 510 Image software (CLSM, Carl Zeiss).

Intracellular $Ca^{+2}$ Measurement

MB purified cells were loaded with 5 µM Quest Fluo-4 (ABD Bioquest, Inc. Sunnyvale, Calif.) for 15 min in 5% CO2 atmosphere. Fluo-4 fluorescence was measured every 16 msec with a back-thinned electron multiplier CCD camera (IMAGEM®; Hamamatsu Photonics, Hamamatsu, Japan). Four consecutive images were averaged. Ratio (F1/F0) to an image at minimum fluorescence intensity (FO) was calculated after background subtraction. The measurements were carried out at room temperature.

Intracellular $Ca^{+2}$ Imaging

For calcium (Ca2+) imaging, MB-based purified cells were plated on 25 mm square glass coverslips (Corning) and incubated in 5% CO2 at 37° C. for 20 min in Tyrode's solution containing calcium dye, Fluo-4AM (7 µM, Molecular Probes, Eugene Oreg.). Cells on coverslips were mounted onto an FHD IonOptix (Ionoptix Scientific Instruments, Milton Mass.) chamber between two platinum electrodes placed 5 mm apart. Cells were perfused with Tyrodes solution at 37° C. for 30 min before imaging for deesterification of the dye. Cells were paced by field stimulation through the platinum electrodes with a 10 ms duration pulse at 0.5 Hz (HSE stimulator P, Hugo Sachs Electronik, F.R. Germany) Confocal imaging was performed using an Olympus FV-1000 system coupled to an Olympus IX-81 automated inverted microscope (Olympus) equipped with a 40× water immersion lens (NA=1.15). Line scan images were taken for determining calcium transients ([Ca2+]) and plotted as F/F0 where FO was the baseline fluorescence measured prior to field stimulation.

---

We claim:

1. A kit comprising a molecular beacon comprising a loop sequence having SEQ ID NO: 2 and a fluorophore.

2. The kit of claim 1 further comprising instructions for purifying cardiomyocytes.

3. The kit of claim 1 further comprising bone morphogenetic protein 4.

4. The kit of claim 1 further comprising activin A.

5. The kit of claim 1 further comprising basic fibroblast growth factor.

6. The kit of claim 1 further comprising isoproterenol.

7. The kit of claim 1, wherein the molecular beacon is enclosed in a container.

8. The kit of claim 7, wherein the container is a vial or ampoule.

9. A method for purifying cardiomyocytes comprising,
   a) introducing a molecular beacon comprising a loop sequence having SEQ ID NO: 2 into a mixture of cardiomyocytes and pluripotent stem cells under conditions such that the molecular beacon hybridizes to mRNA in the cardiomyocytes providing molecular beacon bound fluorescent cardiomyocytes; and
   b) purifying the molecular beacon bound fluorescent cardiomyocytes by fluorescence activated cell sorting to provide a purified composition of cardiomyocytes.

10. The method of claim 9, wherein the mixture of cardiomyocytes and pluripotent stem cells have been differentiated by a method comprising:
    a) culturing undifferentiated stem cells under conditions such that a monolayer of the undifferentiated stem cells is formed,
    b) applying bone morphogenetic protein 4 (BMP4), Activin A, and fibroblast growth factor 2 (FGF2) to the undifferentiated stem cells under conditions such that cardiac lineage cells are formed, and
    c) treating the cardiac lineage cells with isoproterenol to generate spontaneous beating cardiomyocytes.

11. The method of claim 9, wherein the pluripotent stem cells are mammalian pluripotent stem cells.

* * * * *